(12) United States Patent
Homuth et al.

(10) Patent No.: US 10,874,809 B2
(45) Date of Patent: *Dec. 29, 2020

(54) SYSTEMS AND METHODS FOR THERAPEUTIC INTRATHORACIC PRESSURE REGULATION

(71) Applicant: ZOLL Medical Corporation, Chelmsford, MA (US)

(72) Inventors: James Homuth, Corcoran, MN (US); Greg Voss, Lakeville, MN (US); Anja Metzger, Stillwater, MN (US); Keith Lurie, Minneapolis, MN (US)

(73) Assignee: ZOLL Medical Corporation, Chelmsford, MA (US)

( * ) Notice: Subject to any disclaimer, the term of this patent is extended or adjusted under 35 U.S.C. 154(b) by 256 days.

This patent is subject to a terminal disclaimer.

(21) Appl. No.: 16/022,922

(22) Filed: Jun. 29, 2018

(65) Prior Publication Data

US 2019/0030269 A1 Jan. 31, 2019

Related U.S. Application Data

(63) Continuation of application No. 14/978,412, filed on Dec. 22, 2015, now Pat. No. 10,034,991, which is a
(Continued)

(51) Int. Cl.
*A61M 16/00* (2006.01)
*A61M 16/08* (2006.01)
(Continued)

(52) U.S. Cl.
CPC .......... *A61M 16/00* (2013.01); *A61B 5/087* (2013.01); *A61B 5/4836* (2013.01);
(Continued)

(58) Field of Classification Search
CPC .... A61M 6/00; A61M 6/0003; A61M 6/0009; A61M 6/0012; A61M 6/0057;
(Continued)

(56) References Cited

U.S. PATENT DOCUMENTS

| 1,848,232 A | 3/1932 | Swope et al. |
| 2,325,049 A | 7/1943 | Frye et al. |

(Continued)

FOREIGN PATENT DOCUMENTS

| AU | 1487792 B | 10/1992 |
| AU | 60539 B | 11/1994 |

(Continued)

OTHER PUBLICATIONS

US 5,584,866 A, 12/1996, Kroll et al. (withdrawn)
(Continued)

*Primary Examiner* — Joseph D. Boecker
(74) *Attorney, Agent, or Firm* — The Webb Law Firm

(57) ABSTRACT

Embodiments of the present invention provide systems and methods for delivering respiratory treatment to a patient. For example, a treatment system may include a mechanism for delivering a positive pressure breath to a patient, and one or more limb flow control assemblies which modulate gas flow to and from the patient. Exemplary treatment techniques are embodied in anesthesia machines, mechanical ventilators, and manual ventilators.

24 Claims, 27 Drawing Sheets

Related U.S. Application Data continuation of application No. 13/720,858, filed on Dec. 19, 2012, now Pat. No. 9,238,115.

(60) Provisional application No. 61/577,565, filed on Dec. 19, 2011.

(51) Int. Cl.

| | | |
|---|---|---|
| *A61M 16/10* | (2006.01) | |
| *A61M 16/20* | (2006.01) | |
| *A61B 5/00* | (2006.01) | |
| *A61M 16/01* | (2006.01) | |
| *A61M 16/12* | (2006.01) | |
| *A61B 5/087* | (2006.01) | |
| *A61M 16/18* | (2006.01) | |
| *A61M 16/22* | (2006.01) | |

(52) U.S. Cl.
CPC .... *A61M 16/0009* (2014.02); *A61M 16/0063* (2014.02); *A61M 16/0066* (2013.01); *A61M 16/0069* (2014.02); *A61M 16/0078* (2013.01); *A61M 16/0081* (2014.02); *A61M 16/01* (2013.01); *A61M 16/024* (2017.08); *A61M 16/0816* (2013.01); *A61M 16/0875* (2013.01); *A61M 16/0891* (2014.02); *A61M 16/1065* (2014.02); *A61M 16/12* (2013.01); *A61M 16/204* (2014.02); *A61M 16/208* (2013.01); *A61M 16/209* (2014.02); *A61M 16/0012* (2014.02); *A61M 16/0072* (2013.01); *A61M 16/1015* (2014.02); *A61M 16/1055* (2013.01); *A61M 16/18* (2013.01); *A61M 16/22* (2013.01); *A61M 2016/0027* (2013.01); *A61M 2016/0036* (2013.01); *A61M 2016/0042* (2013.01); *A61M 2206/10* (2013.01); *A61M 2230/432* (2013.01)

(58) Field of Classification Search
CPC .............. A61M 6/0066; A61M 6/0069; A61M 6/0078; A61M 6/0081; A61M 6/0084; A61M 6/01; A61M 6/0875; A61M 6/0891; A61M 6/12; A61M 6/204; A61M 2016/0027; A61M 2016/0036; A61M 2016/0042; A61M 2205/3344; A61M 2206/10; A61M 2230/40; A61B 5/087; A61B 5/4836

See application file for complete search history.

(56) References Cited

U.S. PATENT DOCUMENTS

| | | | |
|---|---|---|---|
| 2,774,346 A | 12/1956 | Halliburton | |
| 2,854,982 A | 10/1958 | Pagano | |
| 2,904,898 A | 9/1959 | Marsden | |
| 2,972,345 A * | 2/1961 | Spigel | A61M 16/00 128/204.23 |
| 3,009,266 A | 11/1961 | Brook | |
| 3,049,811 A | 8/1962 | Ruben | |
| 3,068,590 A | 12/1962 | Padellford | |
| 3,077,884 A | 2/1963 | Batrow et al. | |
| 3,191,596 A | 6/1965 | Bird et al. | |
| 3,199,225 A | 8/1965 | Robertson et al. | |
| 3,209,469 A | 10/1965 | James | |
| 3,216,413 A | 11/1965 | Arecheta Mota | |
| 3,274,705 A | 9/1966 | Breakspear | |
| 3,276,147 A | 10/1966 | Padellford | |
| 3,307,541 A | 3/1967 | Hewson | |
| 3,357,426 A | 12/1967 | Cohen | |
| 3,420,232 A | 1/1969 | Bickford | |
| 3,459,216 A | 8/1969 | Bloom et al. | |
| 3,467,092 A | 9/1969 | Bird et al. | |
| 3,509,899 A | 5/1970 | Hewson | |
| 3,515,163 A | 6/1970 | Freeman | |
| 3,523,529 A | 8/1970 | Kissen | |
| 3,552,390 A | 1/1971 | Muller | |
| 3,562,924 A | 2/1971 | Baerman et al. | |
| 3,562,925 A | 2/1971 | Baermann et al. | |
| 3,568,333 A | 3/1971 | Clark | |
| 3,662,751 A | 5/1972 | Barkalow et al. | |
| 3,669,108 A | 6/1972 | Sundblom et al. | |
| 3,734,100 A | 5/1973 | Walker et al. | |
| 3,739,776 A | 6/1973 | Bird et al. | |
| 3,794,043 A | 2/1974 | McGinnis | |
| 3,815,606 A | 6/1974 | Mazal | |
| 3,834,383 A | 9/1974 | Weigl et al. | |
| 3,872,609 A | 3/1975 | Smrcka | |
| 3,874,093 A | 4/1975 | Garbe | |
| 3,875,626 A | 4/1975 | Tysk et al. | |
| 3,933,171 A | 1/1976 | Hay | |
| 3,949,388 A | 4/1976 | Fuller | |
| 3,973,564 A | 8/1976 | Carden | |
| 3,981,398 A | 9/1976 | Boshoff | |
| 3,993,059 A | 11/1976 | Sjostrand | |
| 4,037,595 A | 7/1977 | Elam | |
| 4,041,943 A | 8/1977 | Miller | |
| 4,054,134 A | 10/1977 | Kritzer | |
| 4,077,400 A | 3/1978 | Harrigan | |
| 4,077,404 A | 3/1978 | Elam | |
| 4,095,590 A | 6/1978 | Harrigan | |
| 4,166,458 A | 9/1979 | Harrigan | |
| 4,193,406 A | 3/1980 | Jinotti | |
| 4,198,963 A | 4/1980 | Barkalow et al. | |
| 4,226,233 A | 10/1980 | Kritzer | |
| 4,237,872 A | 12/1980 | Harrigan | |
| 4,240,419 A | 12/1980 | Furlong et al. | |
| 4,259,951 A | 4/1981 | Chernack et al. | |
| 4,262,667 A | 4/1981 | Grant | |
| 4,297,999 A | 11/1981 | Kitrell | |
| 4,298,023 A | 11/1981 | McGinnis | |
| 4,316,458 A | 2/1982 | Hammerton-Fraser | |
| 4,320,754 A | 3/1982 | Watson et al. | |
| 4,326,507 A | 4/1982 | Barkalow | |
| 4,331,426 A | 5/1982 | Sweeney | |
| 4,349,015 A | 9/1982 | Alferness | |
| 4,360,345 A | 11/1982 | Hon | |
| 4,397,306 A | 8/1983 | Weisfeldt et al. | |
| 4,424,806 A | 1/1984 | Newman et al. | |
| 4,446,864 A | 5/1984 | Watson et al. | |
| 4,448,192 A | 5/1984 | Stawitcke et al. | |
| 4,449,526 A | 5/1984 | Elam | |
| 4,481,938 A | 11/1984 | Lindley | |
| 4,501,582 A | 2/1985 | Schulz | |
| 4,513,737 A | 4/1985 | Mabuchi | |
| 4,519,388 A | 5/1985 | Schwanbom et al. | |
| 4,520,811 A | 6/1985 | White et al. | |
| 4,533,137 A | 8/1985 | Sonne | |
| 4,543,951 A | 10/1985 | Phuc | |
| 4,588,383 A | 5/1986 | Parker et al. | |
| 4,598,706 A | 7/1986 | Darowski et al. | |
| 4,601,465 A | 7/1986 | Roy | |
| 4,602,653 A | 7/1986 | Ruiz-Vela et al. | |
| 4,637,386 A | 1/1987 | Baum | |
| 4,738,249 A | 4/1988 | Linman et al. | |
| 4,750,493 A | 6/1988 | Brader | |
| 4,774,941 A | 10/1988 | Cook | |
| 4,797,104 A | 1/1989 | Laerdal et al. | |
| 4,807,638 A | 2/1989 | Sramek | |
| 4,809,683 A | 3/1989 | Hanson | |
| 4,827,935 A | 5/1989 | Geddes et al. | |
| 4,828,501 A | 5/1989 | Ingenito et al. | |
| 4,863,385 A | 9/1989 | Pierce | |
| 4,881,527 A | 11/1989 | Lerman | |
| 4,898,166 A | 2/1990 | Rose et al. | |
| 4,898,167 A | 2/1990 | Pierce et al. | |
| 4,928,674 A | 5/1990 | Halperin et al. | |
| 4,932,879 A | 6/1990 | Ingenito et al. | |
| 4,971,042 A | 11/1990 | Lerman | |
| 4,971,051 A | 11/1990 | Toffolon | |
| 4,984,987 A | 1/1991 | Brault et al. | |
| 5,014,698 A | 5/1991 | Cohen | |

(56) References Cited

U.S. PATENT DOCUMENTS

| | | |
|---|---|---|
| 5,016,627 A | 5/1991 | Dahrendorf et al. |
| 5,029,580 A | 7/1991 | Radford et al. |
| 5,042,500 A | 8/1991 | Norlien et al. |
| 5,050,593 A | 9/1991 | Poon |
| 5,056,505 A | 10/1991 | Warwick et al. |
| 5,083,559 A | 1/1992 | Brault et al. |
| 5,109,840 A | 5/1992 | Daleiden |
| 5,119,825 A | 6/1992 | Huhn |
| 5,150,291 A | 9/1992 | Cummings et al. |
| 5,163,424 A | 11/1992 | Kohnke |
| 5,183,038 A | 2/1993 | Hoffman et al. |
| 5,184,620 A | 2/1993 | Cudahy et al. |
| 5,188,098 A | 2/1993 | Hoffman et al. |
| 5,193,529 A | 3/1993 | Labaere |
| 5,193,544 A | 3/1993 | Jaffe |
| 5,195,896 A | 3/1993 | Sweeney et al. |
| 5,217,006 A | 6/1993 | McCulloch |
| 5,231,086 A | 7/1993 | Sollevi |
| 5,235,970 A | 8/1993 | Augustine |
| 5,238,409 A | 8/1993 | Brault et al. |
| 5,239,988 A | 8/1993 | Swanson et al. |
| 5,263,476 A | 11/1993 | Henson |
| 5,265,595 A | 11/1993 | Rudolph |
| 5,282,463 A | 2/1994 | Hammersley |
| 5,295,481 A | 3/1994 | Geeham |
| 5,301,667 A | 4/1994 | McGrail et al. |
| 5,305,743 A | 4/1994 | Brain |
| 5,306,293 A | 4/1994 | Zacouto |
| 5,312,259 A | 5/1994 | Flynn |
| 5,313,938 A | 5/1994 | Garfield et al. |
| 5,316,907 A | 5/1994 | Lurie et al. |
| 5,330,514 A | 7/1994 | Egelandsdal et al. |
| 5,335,654 A | 8/1994 | Rapoport |
| 5,353,788 A | 10/1994 | Miles |
| 5,355,879 A | 10/1994 | Brain |
| 5,359,998 A | 11/1994 | Lloyd |
| 5,366,231 A | 11/1994 | Hung |
| 5,377,671 A | 1/1995 | Biondi et al. |
| 5,383,786 A | 1/1995 | Kohnke |
| 5,388,575 A | 2/1995 | Taube |
| 5,392,774 A | 2/1995 | Sato |
| 5,395,399 A | 3/1995 | Rosenwald |
| 5,397,237 A | 3/1995 | Dhont et al. |
| 5,398,714 A | 3/1995 | Price |
| 5,413,110 A | 5/1995 | Cummings et al. |
| 5,423,685 A | 6/1995 | Adamson et al. |
| 5,423,772 A | 6/1995 | Lurie et al. |
| 5,425,742 A | 6/1995 | Joy |
| 5,437,272 A | 8/1995 | Fuhrman |
| 5,452,715 A | 9/1995 | Boussignac |
| 5,454,779 A | 10/1995 | Lurie et al. |
| 5,458,562 A | 10/1995 | Cooper |
| 5,468,151 A | 11/1995 | Egelandsdal et al. |
| 5,474,533 A | 12/1995 | Ward et al. |
| 5,477,860 A | 12/1995 | Essen-Moller |
| 5,490,820 A | 2/1996 | Schock et al. |
| 5,492,115 A | 2/1996 | Abramov et al. |
| 5,492,116 A | 2/1996 | Scarberry et al. |
| 5,496,257 A | 3/1996 | Kelly |
| 5,507,282 A * | 4/1996 | Younes ................. A61M 16/04 128/204.21 |
| 5,517,986 A | 5/1996 | Starr et al. |
| 5,544,648 A | 8/1996 | Fischer, Jr. |
| 5,549,106 A | 8/1996 | Gruenke et al. |
| 5,549,581 A | 8/1996 | Lurie et al. |
| 5,551,420 A | 9/1996 | Lurie et al. |
| 5,557,049 A | 9/1996 | Ratner |
| 5,580,255 A | 12/1996 | Flynn |
| 5,582,182 A | 12/1996 | Hillsman |
| 5,588,422 A | 12/1996 | Lurie et al. |
| 5,593,306 A | 1/1997 | Kohnke |
| 5,606,968 A | 3/1997 | Mang |
| 5,614,490 A | 3/1997 | Przybelski |
| 5,617,844 A | 4/1997 | King |
| 5,618,665 A | 4/1997 | Lurie et al. |
| 5,619,665 A | 4/1997 | Emma |
| 5,628,305 A | 5/1997 | Melker |
| 5,632,298 A | 5/1997 | Artinian |
| 5,643,231 A | 7/1997 | Lurie et al. |
| 5,645,522 A | 7/1997 | Lurie et al. |
| 5,657,751 A | 8/1997 | Karr, Jr. |
| 5,678,535 A | 10/1997 | DiMarco |
| 5,685,298 A | 11/1997 | Idris |
| 5,692,498 A | 12/1997 | Lurie et al. |
| 5,697,364 A | 12/1997 | Chua et al. |
| 5,701,883 A | 12/1997 | Hete et al. |
| 5,701,889 A | 12/1997 | Danon |
| 5,704,346 A | 1/1998 | Inoue |
| 5,720,282 A | 2/1998 | Wright |
| 5,722,963 A | 3/1998 | Lurie et al. |
| 5,730,122 A | 3/1998 | Lurie |
| 5,735,876 A | 4/1998 | Kroll et al. |
| 5,738,637 A | 4/1998 | Kelly et al. |
| 5,743,864 A | 4/1998 | Baldwin, II |
| 5,782,883 A | 7/1998 | Kroll et al. |
| 5,794,615 A | 8/1998 | Estes |
| 5,806,512 A | 9/1998 | Abramov et al. |
| 5,814,086 A | 9/1998 | Hirschberg et al. |
| 5,817,997 A | 10/1998 | Wernig |
| 5,823,185 A | 10/1998 | Chang |
| 5,823,787 A | 10/1998 | Gonzalez et al. |
| 5,827,893 A | 10/1998 | Lurie et al. |
| 5,832,920 A | 11/1998 | Field |
| 5,853,292 A | 12/1998 | Eggert et al. |
| 5,881,725 A | 3/1999 | Hoffman et al. |
| 5,885,084 A | 3/1999 | Pastrick et al. |
| 5,891,062 A | 4/1999 | Schock et al. |
| 5,896,857 A | 4/1999 | Hely et al. |
| 5,916,165 A | 6/1999 | Duchon et al. |
| 5,919,210 A | 7/1999 | Lurie et al. |
| 5,927,273 A | 7/1999 | Federowicz et al. |
| 5,937,853 A | 8/1999 | Strom |
| 5,941,710 A | 8/1999 | Lampotang et al. |
| 5,975,081 A | 11/1999 | Hood et al. |
| 5,977,091 A | 11/1999 | Nieman et al. |
| 5,984,909 A | 11/1999 | Lurie et al. |
| 5,988,166 A | 11/1999 | Hayek |
| 6,001,085 A | 12/1999 | Lurie et al. |
| 6,010,470 A | 1/2000 | Albery et al. |
| 6,029,667 A | 2/2000 | Lurie |
| 6,042,532 A | 3/2000 | Freed et al. |
| 6,062,219 A | 5/2000 | Lurie et al. |
| 6,078,834 A | 6/2000 | Lurie et al. |
| 6,086,582 A | 7/2000 | Altman et al. |
| 6,123,074 A | 9/2000 | Hete et al. |
| 6,131,571 A | 10/2000 | Lampotang et al. |
| 6,155,257 A | 12/2000 | Lurie et al. |
| 6,155,647 A | 12/2000 | Albecker, III |
| 6,165,105 A | 12/2000 | Boutellier et al. |
| 6,167,879 B1 | 1/2001 | Sievers et al. |
| 6,174,295 B1 | 1/2001 | Cantrell et al. |
| 6,176,237 B1 | 1/2001 | Wunderlich et al. |
| 6,193,519 B1 | 2/2001 | Eggert et al. |
| 6,209,540 B1 | 4/2001 | Sugiura et al. |
| 6,224,562 B1 | 5/2001 | Lurie et al. |
| 6,234,916 B1 | 5/2001 | Carusillo et al. |
| 6,234,985 B1 | 5/2001 | Lurie et al. |
| 6,277,107 B1 | 8/2001 | Lurie et al. |
| 6,296,490 B1 | 10/2001 | Bowden |
| 6,312,399 B1 | 11/2001 | Lurie et al. |
| 6,334,441 B1 | 1/2002 | Zowtiak et al. |
| 6,356,785 B1 | 3/2002 | Snyder et al. |
| 6,369,114 B1 | 4/2002 | Weil et al. |
| 6,374,827 B1 | 4/2002 | Bowden et al. |
| 6,390,996 B1 | 5/2002 | Halperin et al. |
| 6,425,393 B1 | 7/2002 | Lurie et al. |
| 6,439,228 B1 | 8/2002 | Hete et al. |
| 6,459,933 B1 | 10/2002 | Lurie et al. |
| 6,463,327 B1 | 10/2002 | Lurie et al. |
| 6,486,206 B1 | 11/2002 | Lurie |
| 6,526,970 B2 | 3/2003 | DeVries et al. |
| 6,526,973 B1 | 3/2003 | Lurie et al. |
| 6,536,432 B2 | 3/2003 | Truschel |
| 6,544,172 B2 | 4/2003 | Toeppen-Sprigg |

(56) References Cited

U.S. PATENT DOCUMENTS

| | | |
|---|---|---|
| 6,555,057 B1 | 4/2003 | Barbut et al. |
| 6,578,574 B1 | 6/2003 | Kohnke |
| 6,584,973 B1 | 7/2003 | Biondi et al. |
| 6,587,726 B2 | 7/2003 | Lurie et al. |
| 6,595,213 B2 | 7/2003 | Bennarsten |
| 6,604,523 B2 | 8/2003 | Lurie et al. |
| 6,622,274 B1 | 9/2003 | Lee et al. |
| 6,622,724 B1 | 9/2003 | Truitt et al. |
| 6,631,716 B1 | 10/2003 | Robinson et al. |
| 6,656,166 B2 | 12/2003 | Lurie et al. |
| 6,662,032 B1 | 12/2003 | Gavish et al. |
| 6,672,300 B1* | 1/2004 | Grant .............. A61M 16/00 128/204.26 |
| 6,676,613 B2 | 1/2004 | Cantrell et al. |
| 6,726,634 B2 | 4/2004 | Freeman |
| 6,729,334 B1 | 5/2004 | Baran |
| 6,758,217 B1 | 7/2004 | Younes |
| 6,776,156 B2 | 8/2004 | Lurie et al. |
| 6,780,017 B2 | 8/2004 | Pastrick et al. |
| 6,792,947 B1 | 9/2004 | Bowden |
| 6,863,656 B2 | 3/2005 | Lurie |
| 6,877,511 B2 | 4/2005 | DeVries et al. |
| 6,935,336 B2 | 8/2005 | Lurie et al. |
| 6,938,618 B2 | 9/2005 | Lurie et al. |
| 6,986,349 B2 | 1/2006 | Lurie |
| 6,988,499 B2 | 1/2006 | Holt et al. |
| 7,011,622 B2 | 3/2006 | Kuyava et al. |
| 7,032,596 B2 | 4/2006 | Thompson et al. |
| 7,044,128 B2 | 5/2006 | Lurie et al. |
| 7,066,173 B2 | 6/2006 | Banner et al. |
| 7,082,945 B2 | 8/2006 | Lurie |
| 7,096,866 B2 | 8/2006 | Be'eri et al. |
| 7,174,891 B2 | 2/2007 | Lurie et al. |
| 7,185,649 B2 | 3/2007 | Lurie |
| 7,188,622 B2 | 3/2007 | Martin et al. |
| 7,195,012 B2 | 3/2007 | Lurie |
| 7,195,013 B2 | 3/2007 | Lurie |
| 7,204,251 B2 | 4/2007 | Lurie |
| 7,210,480 B2 | 5/2007 | Lurie et al. |
| 7,220,235 B2 | 5/2007 | Geheb et al. |
| 7,226,427 B2 | 6/2007 | Steen |
| 7,275,542 B2 | 10/2007 | Lurie et al. |
| 7,311,668 B2 | 12/2007 | Lurie |
| 7,469,700 B2 | 12/2008 | Baran |
| 7,487,773 B2 | 2/2009 | Li |
| 7,500,481 B2 | 3/2009 | Delache et al. |
| 7,594,508 B2 | 9/2009 | Doyle |
| 7,650,181 B2 | 1/2010 | Freeman et al. |
| 7,682,312 B2 | 3/2010 | Lurie |
| 7,766,011 B2 | 8/2010 | Lurie |
| 7,793,659 B2 | 9/2010 | Breen |
| 7,824,436 B2 | 11/2010 | Barbut et al. |
| 7,836,881 B2 | 11/2010 | Lurie et al. |
| 7,899,526 B2 | 3/2011 | Benditt et al. |
| 8,011,367 B2 | 9/2011 | Lurie et al. |
| 8,108,204 B2 | 1/2012 | Gabrilovich et al. |
| 8,151,790 B2 | 4/2012 | Lurie et al. |
| 8,210,176 B2 | 7/2012 | Metzger et al. |
| 8,287,474 B1 | 10/2012 | Koenig et al. |
| 8,388,682 B2 | 3/2013 | Hendricksen et al. |
| 8,408,204 B2 | 4/2013 | Lurie |
| 8,702,633 B2 | 4/2014 | Voss et al. |
| 8,755,902 B2 | 6/2014 | Lurie et al. |
| 8,939,922 B2 | 1/2015 | Strand et al. |
| 9,238,115 B2* | 1/2016 | Homuth ............ A61M 16/0078 |
| 10,034,991 B2* | 7/2018 | Homuth ............. A61M 16/204 |
| 2001/0003984 A1 | 6/2001 | Bennarsten et al. |
| 2001/0029339 A1 | 10/2001 | Orr et al. |
| 2001/0047140 A1 | 11/2001 | Freeman |
| 2002/0007832 A1 | 1/2002 | Doherty |
| 2002/0069878 A1 | 6/2002 | Lurie et al. |
| 2002/0104544 A1 | 8/2002 | Ogushi et al. |
| 2002/0170562 A1 | 11/2002 | Lurie et al. |
| 2002/0179090 A1 | 12/2002 | Boussignac |
| 2003/0000526 A1 | 1/2003 | Gobel |
| 2003/0015200 A1* | 1/2003 | Hansen ............... A61M 16/026 128/204.18 |
| 2003/0037784 A1 | 2/2003 | Lurie |
| 2003/0051729 A1* | 3/2003 | Be'eri ............... A61M 16/0084 128/204.18 |
| 2003/0062040 A1 | 4/2003 | Lurie et al. |
| 2003/0062041 A1 | 4/2003 | Keith et al. |
| 2003/0192547 A1 | 10/2003 | Lurie et al. |
| 2004/0016428 A9 | 1/2004 | Lurie |
| 2004/0058305 A1 | 3/2004 | Lurie et al. |
| 2004/0200473 A1 | 10/2004 | Lurie et al. |
| 2004/0200474 A1 | 10/2004 | Lurie |
| 2004/0210281 A1 | 10/2004 | Dzeng et al. |
| 2004/0211415 A1 | 10/2004 | Lurie |
| 2004/0211416 A1 | 10/2004 | Lurie |
| 2004/0211417 A1 | 10/2004 | Lurie |
| 2004/0231664 A1 | 11/2004 | Lurie et al. |
| 2004/0267325 A1 | 12/2004 | Geheb et al. |
| 2005/0016534 A1 | 1/2005 | Ost |
| 2005/0075531 A1 | 4/2005 | Loeb et al. |
| 2005/0126567 A1 | 6/2005 | Lurie |
| 2005/0165334 A1 | 7/2005 | Lurie |
| 2005/0199237 A1 | 9/2005 | Lurie |
| 2005/0217677 A1 | 10/2005 | Lurie et al. |
| 2005/0267381 A1 | 12/2005 | Benditt et al. |
| 2006/0089574 A1 | 4/2006 | Paradis |
| 2006/0129191 A1 | 6/2006 | Sullivan et al. |
| 2006/0270952 A1 | 11/2006 | Freeman et al. |
| 2007/0017523 A1 | 1/2007 | Be-Eri et al. |
| 2007/0021683 A1 | 1/2007 | Benditt et al. |
| 2007/0060785 A1 | 3/2007 | Freeman et al. |
| 2007/0199566 A1* | 8/2007 | Be'eri ............... A61M 16/0051 128/204.23 |
| 2007/0221222 A1 | 9/2007 | Lurie |
| 2007/0277826 A1 | 12/2007 | Lurie |
| 2008/0039748 A1 | 2/2008 | Palmer et al. |
| 2008/0047555 A1 | 2/2008 | Lurie et al. |
| 2008/0092891 A1 | 4/2008 | Cewers |
| 2008/0097258 A1 | 4/2008 | Walker |
| 2008/0097385 A1 | 4/2008 | Vinten-Johansen et al. |
| 2008/0108905 A1 | 5/2008 | Lurie |
| 2008/0255482 A1 | 10/2008 | Lurie |
| 2008/0257344 A1 | 10/2008 | Lurie et al. |
| 2009/0020128 A1 | 1/2009 | Metzger et al. |
| 2009/0062701 A1 | 3/2009 | Yannopoulos et al. |
| 2009/0076573 A1 | 3/2009 | Burnett et al. |
| 2009/0164000 A1 | 6/2009 | Shirley |
| 2009/0277447 A1 | 11/2009 | Voss et al. |
| 2009/0299156 A1 | 12/2009 | Simpson et al. |
| 2010/0000535 A1 | 1/2010 | Wickham et al. |
| 2010/0147302 A1 | 6/2010 | Selvarajan et al. |
| 2010/0174278 A1 | 7/2010 | Barbut et al. |
| 2010/0179442 A1 | 7/2010 | Lurie |
| 2010/0247682 A1 | 9/2010 | Gladwin et al. |
| 2010/0319691 A1* | 12/2010 | Lurie ............... A61M 16/0012 128/203.12 |
| 2011/0056491 A1 | 3/2011 | Rumph et al. |
| 2011/0098612 A1 | 4/2011 | Lurie |
| 2011/0160782 A1 | 6/2011 | Lurie et al. |
| 2011/0201979 A1 | 8/2011 | Voss et al. |
| 2011/0297147 A1 | 12/2011 | Lick et al. |
| 2012/0016279 A1 | 1/2012 | Banville et al. |
| 2012/0203147 A1 | 8/2012 | Lurie et al. |
| 2012/0302908 A1 | 11/2012 | Hemnes et al. |
| 2012/0330199 A1 | 12/2012 | Lurie et al. |
| 2012/0330200 A1 | 12/2012 | Voss et al. |
| 2013/0118498 A1 | 5/2013 | Robitaille et al. |
| 2013/0172768 A1 | 7/2013 | Lehman |
| 2013/0231593 A1 | 9/2013 | Yannopoulos et al. |
| 2013/0269701 A1 | 10/2013 | Lurie |
| 2014/0005566 A1 | 1/2014 | Homuth et al. |
| 2014/0048061 A1 | 2/2014 | Yannopoulos et al. |
| 2016/0287834 A1 | 10/2016 | Bennett |

FOREIGN PATENT DOCUMENTS

| | | |
|---|---|---|
| AU | 687942 B | 5/1995 |
| CA | 668771 A | 8/1963 |

(56) References Cited

FOREIGN PATENT DOCUMENTS

| CA | 2077608 | A1 | 3/1993 |
|---|---|---|---|
| CA | 2214887 | A1 | 9/1996 |
| CN | 1183731 | A | 6/1998 |
| DE | 2453490 | A1 | 5/1975 |
| DE | 4308493 | A1 | 9/1994 |
| EP | 0029352 | A1 | 5/1981 |
| EP | 0139363 | A1 | 5/1985 |
| EP | 0245142 | A1 | 11/1987 |
| EP | 0367285 | A2 | 5/1990 |
| EP | 0411714 | A1 | 2/1991 |
| EP | 0509773 | A1 | 10/1992 |
| EP | 0560440 | A1 | 9/1993 |
| EP | 0623033 | A1 | 11/1994 |
| GB | 1344862 | A | 1/1974 |
| GB | 1465127 | A | 2/1977 |
| GB | 2117250 | A | 10/1983 |
| GB | 2139099 | A | 11/1984 |
| JP | 2005000675 | A | 1/2005 |
| JP | 2006524543 | A | 11/2006 |
| JP | 2007504859 | A | 3/2007 |
| WO | 9005518 | A1 | 5/1990 |
| WO | 9302439 | A1 | 2/1993 |
| WO | 9321982 | A1 | 11/1993 |
| WO | 9426229 | A1 | 11/1994 |
| WO | 9513108 | A1 | 5/1995 |
| WO | 9528193 | A1 | 10/1995 |
| WO | 9628215 | A1 | 9/1996 |
| WO | 9820938 | A1 | 5/1998 |
| WO | 9947197 | A1 | 9/1999 |
| WO | 9963926 | A2 | 12/1999 |
| WO | 0020061 | A1 | 4/2000 |
| WO | 0102049 | A2 | 1/2001 |
| WO | 0170092 | A2 | 9/2001 |
| WO | 0170332 | A2 | 9/2001 |
| WO | 02092169 | A1 | 11/2002 |
| WO | 2004096109 | A3 | 11/2004 |
| WO | 2006088373 | A1 | 8/2006 |
| WO | 2008147229 | A1 | 12/2008 |
| WO | 2010044034 | A1 | 4/2010 |
| WO | 2013064888 | A1 | 5/2013 |
| WO | 2013096495 | A1 | 6/2013 |
| WO | 2014026193 | A1 | 2/2014 |

OTHER PUBLICATIONS

Advanced Circulatory Systems, Inc. (Jan. 2014), Emerging Data: The Resuscitation Outcomes Consortium (ROC) PRIMED Study on the Efficacy of the ITD (#49-0864-000,06) [Brochure], Roseville, MN:Advanced Circulatory Systems, Inc. 2 pages.
Advanced Circulatory Systems, Inc. (Jan. 2013), Emerging Data: The Resuscitation Outcomes Consortium (ROC) PRIMED Study on the Efficacy of the ITD (#49-0864-000,05) [Brochure], Roseville, MN:Advanced Circulatory Systems, Inc. 2 pages.
Advanced Circulatory Systems, Inc. (Mar. 2012), Benefits of the ResQPOD Based Upon the ROC PRIMED Study (#49-0864-000,04) [Brochure], Roseville, MN:Advanced Circulatory Systems, Inc. 2 pages.
Advanced Circulatory Systems, Inc. (Jan. 2012), Benefits of the ResQPOD Based Upon the ROC PRIMED Study (#49-0864-000,03) [Brochure], Roseville, MN:Advanced Circulatory Systems, Inc. 2 pages.
Advanced Circulatory Systems, Inc. (Aug. 2011),Early Intervention is Life-Saving in Cardiac Arrest (#49-0864-000,01) [Brochure], Roseville, MN:Advanced Circulatory Systems, Inc. 2 pages.
Advanced Circulatory Systems, Inc. (Aug. 2011),Early Intervention is Life-Saving in Cardiac Arrest (#49-0864-000,02) [Brochure], Roseville, MN:Advanced Circulatory Systems, Inc. 2 pages.
Advanced Circulatory Systems, Inc. (2013), ResQPOD More than a Heartbeat (#49-0336-000,08) [Brochure], Roseville, MN:Advanced Circulatory Systems, Inc. 2 pages.
Advanced Circulatory Systems, Inc.(2011), ResQPOD ITD:Strengthening the Chain of Survival (#49-0336000,06) [Brochure], Roseville, MN:Advanced Circulatory Systems, Inc. 2 pages.
Advanced Circulatory Systems, Inc. (2010), ResQPOD Impedance Threshold Device:Strengthening the Chain of Survival (#49-0336000,05) [Brochure], Roseville, MN:Advanced Circulatory Systems, Inc. 2 pages.
Advanced Circulatory Systems, Inc. (2010), ResQPOD Impedance Threshold Device:Strengthening the Chain of Survival (#49-0336000,04) [Brochure], Roseville, MN:Advanced Circulatory Systems, Inc. 2 pages.
Advanced Circulatory Systems, Inc. (2010), ResQPOD Impedance Threshold Device 10.0: Strengthening the Chain of Survival (#49-0336000,03) [Brochure], Roseville, MN:Advanced Circulatory Systems, Inc. 2 pages.
Advanced Circulatory Systems, Inc. (2006). ResQPOD® Circulatory Enhancer: Strengthening the Chain of Survival (#49-0336-000, 02). [Brochure). Roseville.MN: Advanced Circulatory Systems,Inc., 2 pages.
Advanced Circulatory Systems, Inc. (2006). ResQPOD® Circulatory Enhancer: Strengthening the Chain of Survival (#49-0336-000, 01) [Brochure). Roseville, MN: Advanced Circulatory Systems, Inc. 2 pages.
Advanced Circulatory Systems, Inc. (2011). ResQPOD® Perfusion on Demand: ResQPOD Impedance Threshold Device (#49-0324-001, 05) [Brochure). Roseville, MN: Advanced Circulatory Systems, Inc., 2 pages.
Advanced Circulatory Systems, Inc. (2011). ResQPOD® Perfusion on Demand: ResQPOD Impedance Threshold Device (#49-0324-001, 04) [Brochure). Roseville, MN: Advanced Circulatory Systems, Inc. 2 pages.
Advanced Circulatory Systems,Inc. (2010). ResQPOD® Perfusion on Demand: ResQPOD Impedance Threshold Device (#49-0324-001, 03) [Brochure). Roseville, MN: Advanced Circulatory Systems, Inc., 2 pages.
Advanced Circulatory Systems,Inc. (2009). ResQPOD® Perfusion on Demand: ResQPOD Impedance Threshold Device (#49-0324-001, 02) [Brochure). Roseville, MN: Advanced Circulatory Systems, Inc., 2 pages.
Advanced Circulatory Systems,Inc. (2005). Introducing ResQPOD® (#49-0324-000, 01) [Brochure). Roseville, MN: Advanced Circulatory Systems, Inc., 2 pages.
Ambu InternationalNS Directions for use of Ambu® CardioPump™. Sep. 1992, 8 pages.
Aufderheide et al., "Standard cardiopulmonary resuscitation versus active compression-decompression cardiopulmonary resuscitation with augmentation of negative intrathoracic pressure for out-of-hospital cardiac arrest: A randomized trial, " 2011, Lancet, vol. 377, pp. 301-311.
Aufderheide et al., "Hyperventilation-Induced Hypotension During Cardiopulmonary Resuscitation," Circulation; 2004, vol. 109:16, pp. 1960-1965.
Azim et al, "Case Report The use of bispectral index during a cardiopulmonary arrest: a potential predictor of cerebral perfusion", Anesthesia, 2009, vol. 59, pp. 610-612.
Babbs, "CPR Techniques that Combine Chest and Abdominal Compression and Decompression: Hemodynamic Insights from a Spreadsheet Model," Circulation,1999, pp. 2146-2152.
Christenson et al., "Abdominal Compressions During CPR: Hemodynamic Effects of Altering Timing and Force", The Journal of Emergency Medicine, 1992,vol. 10, pp. 257-266.
Cohen et al., "Active compression-decompression resuscitation: A novel method of cardiopulmonary resuscitation," American Heart Journal vol. 124:5, pp. 1145-1150.
Cohen et al., "Active Compression-Decompression: A New Method of Cardiopulmonary Resuscitation," 1992, JAMA, vol. 267:29, pp. 2916-2923.
Dupuis, "Ventilators—Theory and Clinical Application," Jan. 1986, The C.V. Mosby Company, pp. 447-448, 481, 496.
Edelson et al. Effects of compression depth and pre-shock pauses predict defibrillation failure during cardiac arrest. Resuscitation 2006, vol. 71, pp. 137-145.
Geddes et al., "Inspiration Produced by Bilateral Electromagnetic, Cervical Phrenic Nerve Stimulation in Man," IEEE Transactions on Biomedical Engineering, 1991, vol. 38:9, pp. 1047-1048.

(56) References Cited

OTHER PUBLICATIONS

Geddes et al., "Optimum Stimulus Frequency for Contracting the Inspiratory Muscles with Chest-Surface Electrodes to Produce Artificial respiration," Annals of Biomedical Engineering, 1990, vol. 18, pp. 103-108.
Geddes et al., "Electrically Produced Artificial Ventilation," Medical Instrumentation, 1988, vol. 22:5; pp. 263-271.
Geddes, "Electroventilation—A Missed Opportunity?" Biomedical Instrumentation & Technology, 1998, pp. 401-414.
Glen et al., "Diaphragm Pacing by Electrical Stimulation of the Phrenic Nerve," Neurosurgery, 1985, vol. 17:6, pp. 974-984.
Glenn et al., "Twenty Years of Experience in Phrenic Nerve Stimulation to Pace the Diaphragm," Nov. /Dec. 1986, Part I, Pace 9, pp. 780-784.
Guidelines for Cardiopulmonary Resuscitation and Emergency Cardiac Care, JAMA, 1992, vol. 268; pp. 2172-2177.
Johnson et al., "Time to Throw Away Your Stethoscope? Capnography: Evidence-Based Patient Monitoring Technology", Journal of Radiology Nursing, 2011, vol. 30:1, pp. 25-34.
Jung et al., "Usefulness of the bispectral index during cardiopulmonary resuscitation—A case report-", Korean J Anesthesiol, 2013, vol. 64:1, pp. 69-72.
Kotze et al., "Diaphragm pacing in the treatment of ventilatory failure," SAMT, 1995, vol. 68, pp. 223-224.
Laghi et al., "Comparison of Magnetic and Electrical Phrenic Nerve Stimulation in assessment of Diaphragmantic Contractility," American Physiological Society, 1996, pp. 1731-1742.
Lindner et al., "Effects of Active Compression-Decompression Resuscitation on Myocardialand Cerebral Blood Flow in Pigs," Circulation, 1993, vol. 88:3, 1254-1263.
Lurie et al., "Comparison of a 10-Breaths-Per-Minute Versus a 2-Breaths-Per-Minute Strategy During Cardiopulmonary Resuscitation in a Porcine Model of Cardiac Arrest," Respiratory Care, 2008, vol. 53:7, pp. 862-870.
Lurie et al., "Regulated to Death: The Matter of Informed Consent for Human Experimentation in Emergency Resuscitation Research," PACE, 1995, vol. 8, pp. 1443-1447.
Michigan Instruments, Inc.Thumper 1007CC Continuous Compression Cardiopulmonary Resuscitation System, obtained online Jul. 15, 2006 at http://WwW.michiganinstruments.com/resus-thumper.htm, 1 page.
Mushin et al., "Automatic Ventilation of the Lungs—The Lewis-Leigh Inflating Valve," 1969, Blackwell Scientific, Oxford, GB, p. 838.
Sato et al. Adverse effects of interrupting precordial compression during cardiopulmonary resuscitation. Crit. Care Med. 1997, vol. 25, No. 5, pp. 733-736.
Schultz et al., "Sodium nitroprusside enhanced cardiopulmonary resuscitation (SNPeCPR) improves vital organ perfusion pressures and carotid blood flow in a porcine model of cardiac arrest," Resuscitation, 2012, vol. 83, pp. 374-377.
Segal et al., "Ischemic postconditioning at the initiation of cardiopulmonary resuscitation facilitates cardiac and cerebral recovery after prolonged untreated ventricular fibrillation," Resuscitation, 2012, pp. 1-7.
Shapiro et al., "Neurosurgical Anesthesia and Intracranial Hypertension," Anesthesia, 3rd Edition, 1990, Church Livingston, New York, Chapter 54.
Steen et al. The critical importance of minimal delay between chest compressions and subsequent defibrillation: a haemodynamic explanation. Resuscitation 2003, vol. 58, pp. 249-258.
Yannopoulos et al., "Controlled pauses at the initiation of sodium nitroprussdi e-enhanced cardiopulmonary resuscitation facilitate neurological and cardiac recovery after 15 minutes of untreated ventricular fibrillation," Critical Care Medicine , 2012, vol. 40:5, pp. 1-8.
Yannopoulos et al., "Intrathoracic Pressure Regulator During Continuous-Chest-Compression Advanced Cardiac Resuscitation Improves Vital Organ Perfusion Pressures in a Porcine Modelof Cardiac Arrest", Circulation, 2005, pp. 803-811.
Yannopoulos et al., "Intrathoracic Pressure Regulation Improves 24. Hour Survival in a Porcine Modelof Hypovolemic Shock," Anesthesia & Analgesia, ITPR and Survival in Hypovolemic Shock, 2007, vol. 104:1, pp. 157-162.
Yannopoulos et al.,"Intrathoracic pressure regulation improves vital organ perfusion pressures in normovolemic and hypovolemic pigs," Resuscitation, 2006, vol. 70, pp. 445-453.
Yannopoulos et al., "Sodium nitroprusside enhanced cardiopulmonary resuscitation improves survival with good neurological function in a porcine model of prolonged cardiac arrest," Critical Care Medicine, 2011, vol. 39:6 pp. 1-6.
Yu et al. Adverse outcomes of interrupted precordial compression during automated defibrillation. Circulation 2002, vol. 106, pp. 368-372.
Zhao et. al., "Inhibation of myocardial injury by ischemic postconditioning during reperfusion: comparison with ischemic preconditioning," AJP Heart Circ Physiol, 2003, vol. 285, pp. H579-H588.
Zoll Autopulse Non-Invasive Cardiac Support Pump, obtained online on 715106 at http://www.zoll.com/product.aspx?id=84,1 page.

\* cited by examiner

ANESTHESIA MACHINE WITH ACTIVE EXHALATION

SYSTEMS AND METHODS FOR THERAPEUTIC INTRATHORACIC PRESSURE REGULATION

CROSS-REFERENCES TO RELATED APPLICATIONS

This application is a continuation of co-pending U.S. patent application Ser. No. 14/978,412, filed Dec. 22, 2015, which is a continuation of U.S. patent application Ser. No. 13/720,858, filed Dec. 19, 2012, now U.S. Pat. No. 9,238,115, which is a nonprovisional of and claims the benefit of priority to U.S. Patent Application No. 61/577,565 filed Dec. 19, 2011, the contents of which are incorporated herein by reference. This application is also related to U.S. Pat. Nos. 6,938,618, 7,195,012, 7,275,542, 7,836,881, and to U.S. Patent Publication Nos. 2010/0319691 and 2011/0098612, the contents of which are incorporated herein by reference.

BACKGROUND OF THE INVENTION

Embodiments of the present invention relate generally to the field of respiratory and circulatory enhancement, and in particular to systems and methods for providing a patient with intrathoracic pressure regulator treatment, for example when the patient is spontaneously breathing, during an anesthesia regimen, or when providing positive pressure ventilation with other external sources such as a mechanical ventilator or a manual resuscitator bag.

Current treatment techniques may include the use an anesthesia machine, a ventilator, or a bag valve mask to deliver positive pressure breaths to a patient as part of a therapeutic protocol.

Although these and other proposed treatments may provide real benefits to patients in need thereof, still further advances would be desirable. Embodiments of the present invention provide novel and clinically important solutions that address the problems which may be associated with the techniques described above, and hence provide answers to at least some of these outstanding needs. In some cases, embodiments provide for the delivery of therapeutic intrathoracic pressure regulation when used with a mechanical ventilator or other forms of positive pressure ventilation.

BRIEF SUMMARY OF THE INVENTION

Intrathoracic pressure regulators can provide a patient with positive pressure ventilation and then generate negative intrathoracic pressure, which enhances blood flow back to the heart and lowers intracranial pressures. These physiological benefits result in greater circulation of oxygen-rich blood to the heart and brain. An intrathoracic pressure regulator can be coupled with or attached externally to an anesthesia machine in a variety of ways. The incorporation of an intrathoracic pressure regulator into an anesthesia machine or ventilation device in a manner that does not interrupt or minimally changes current practice allows an operator to administer beneficial respiratory and circulatory treatments to a patient in need thereof.

Embodiments of the present invention encompass flow control assemblies for anesthesia rebreathing systems, mechanical ventilators, self-refilling resuscitators such as bag valve masks (BVM), and spontaneous breathing without added mechanical ventilation devices. In some cases, a blower or pump operates to modulate flow in the expiratory limb, and a threshold valve operates to modulates flow in the inspiratory limb. In some cases, a single mechanism, such as a blower, pump, or turbine, may operate to modulate flow in both the inspiratory limb and the expiratory limb, as well as other locations along a rebreathing circuit.

In one aspect, embodiments of the present invention encompass systems and methods for providing anesthesia therapy to a patient. Exemplary systems may include a machine-side assembly having a rebreathing circuit, a carbon dioxide absorber mechanism providing an inlet in fluid communication with the rebreathing circuit and an outlet in fluid communication with the rebreathing circuit, an inhalation check valve providing an inlet and an outlet, where the inlet of the inhalation check valve in fluid communication with the outlet of the carbon dioxide absorber mechanism via the rebreathing circuit, an exhalation check valve providing an inlet and an outlet, where the outlet of the exhalation check valve in fluid communication with the inlet of the carbon dioxide absorber mechanism via the rebreathing circuit, and an anesthesia delivery mechanism in fluid communication with the rebreathing circuit. Exemplary systems may also include a patient-side assembly having an inspiratory limb mechanism fluidly coupleable with the outlet of the inhalation check valve, an expiratory limb mechanism fluidly coupleable with the inlet of the exhalation check valve, and a patient airway flow tube that provides a fluid connection between an airway of the patient and the inspiratory and expiratory limb mechanisms. Exemplary systems may further include an expiratory limb flow control assembly operable to modulate gas flow through the expiratory limb mechanism, and an inspiratory limb flow control assembly operable to modulate gas flow through the inspiratory limb mechanism. In some instances, the expiratory limb control assembly includes a reciprocating pump, a turbine, a centrifugal blower, a roots blower, a vacuum source, or the like. In some instances, the inspiratory limb control assembly comprises a valve mechanism. In some instances, the valve mechanism inhibits gas flow into the patient airway flow tube from the inspiratory limb mechanism when a pressure in the inspiratory limb mechanism is between about 0 cm $H_2O$ and about −15 cm $H_2O$. In some instances, the valve mechanism allows gas flow into the patient airway flow tube from the inspiratory limb mechanism when a pressure in the inspiratory limb mechanism is greater than about 0 cm $H_2O$ or equal to or less than a maximum negative pressure value. Optionally, the maximum negative pressure value may be between about 0 cm $H_2O$ and about −15 cm $H_2O$. According to some embodiments, the expiratory limb flow control assembly operates to remove gas from the flow circuit, from the expiratory limb mechanism, or from both. According to some embodiments, the expiratory limb flow control assembly operates to circulate gas within the rebreathing circuit, away from the exhalation check valve and toward the inhalation check valve. The expiratory limb flow control assembly may be coupled with the expiratory limb mechanism. The inspiratory limb flow control assembly may be coupled with the inspiratory limb mechanism. The expiratory limb flow control assembly may be coupled with the rebreathing circuit at a location between the carbon dioxide absorber mechanism and the exhalation check valve. The inspiratory limb flow control assembly may be coupled with the rebreathing circuit at a location between the carbon dioxide absorber mechanism and the inhalation check valve. In some instances, the expiratory limb flow control assembly includes a pump or a suction source located on the expiratory limb mechanism or on the rebreathing circuit, optionally at a location described in FIG. 3. In some instances, the expiratory limb flow control assembly is present in the rebreathing circuit and provides an enhancement of $CO_2$ absorption, a reduction of $CO_2$ absorber channeling, a resultant increased inspired humidity level, or a homogenization of an anesthetic gas mixture, or any combination thereof.

In some instances, a patient side assembly of a ventilator or anesthesia system may include a single limb circuitry mechanism having an inner passage (e.g. outer tube) and an outer passage (e.g. inner tube) arranged in a concentric or nested fashion, wherein the outer passage or tube provides an expiratory path and the inner passage or tube provides an inspiratory path, or wherein the inner passage or tube provides an expiratory path and the outer passage or tube provides an inspiratory path.

In another aspect, embodiments of the present invention encompass systems for providing therapy to a patient that include, for example, means for delivering a positive pressure breath to an airway of the patient during an inspiration phase, and means for delivering a negative pressure to the airway of the patient during the inspiration phase and during an expiration phase.

In another aspect, embodiments of the present invention encompass systems for providing therapy to a patient that include, for example, means for intermittently delivering a positive pressure breath to an airway of the patient, and means for continuously delivering a negative pressure to the airway of the patient.

In yet another aspect, embodiments of the present invention encompass mechanical ventilator systems and methods for providing ventilation therapy to a patient. Exemplary systems include a machine-side assembly having an inspiratory flow delivery system, an expiratory flow return system, an inhalation port providing an inlet and an outlet, where the inlet of the inhalation port is in fluid communication with inspiratory flow delivery system, and an exhalation port providing an inlet and an outlet, where the outlet of the exhalation port is in fluid communication with the expiratory flow return system. Exemplary systems may also include a patient-side assembly having an inspiratory limb mechanism fluidly coupleable with the outlet of the inhalation port, an expiratory limb mechanism fluidly coupleable with the inlet of the exhalation port, and a patient airway flow tube that provides a fluid connection between an airway of the patient and the inspiratory and expiratory limb mechanisms. Further, exemplary systems may include an expiratory limb flow control assembly operable to modulate gas flow through the expiratory limb mechanism, and an inspiratory limb flow control assembly operable to modulate gas flow through the inspiratory limb mechanism. In some cases, the expiratory limb flow control assembly includes a pump or suction source located in the expiratory limb mechanism, and the inspiratory limb flow control assembly is located in the inspiratory limb mechanism. In some cases, the expiratory limb flow control assembly is positioned at any location specified in FIG. 4, and the expiratory limb mechanism is positioned at any location specified in FIG. 4.

In another aspect, embodiments of the present invention encompass manual ventilator systems and methods for providing ventilation therapy to a patient. Exemplary systems may include a resuscitator valve assembly having an inspiration gas flow input, an expiration gas flow output, and a patient connection, a self-refilling resuscitator mechanism, an inspiratory limb mechanism that provides fluid communication between the self-refilling resuscitator mechanism and the inspiration gas flow input of the resuscitator valve assembly, an inspiratory limb flow control assembly operable to modulate gas flow through the inspiratory limb mechanism, an expiratory limb flow control assembly, and an expiratory limb mechanism that provides fluid communication between the expiratory limb flow control assembly and the expiration gas flow output of the resuscitator valve assembly. In some instances, the self-refilling resuscitator mechanism includes a self-refilling manual resuscitation bag, wherein the expiratory limb mechanism comprises a negative pressure turbine, optionally with an exhalation flow sensor, and wherein the negative pressure turbine is positioned along an exhalation path of a manual resuscitator valve to provide IPR therapy. In some cases, the resuscitation bag is attached to an external suction source. In some cases, the turbine includes an external vacuum source. In some cases, the manual ventilator system further includes a controller in operative association with the expiratory limb flow control assembly. In some cases, the device or turbine is connected between the patient and the breathing system. In some cases, the patient breathes room air or mixed gas, spontaneously through the device or turbine. In some cases, the controller is configured to provide instruction to an operator regarding proper timing and minimum and maximum inspiratory pressure, as measured by the patient circuit pressure sensor, of a manually delivered positive pressure breath, optionally in conjunction with the administration of cardiopulmonary resuscitation. In some cases, the inspiratory limb flow control assembly comprises a threshold valve that is electronically gated. In some cases, the inspiratory limb flow control assembly includes a threshold valve that is pneumatically or electronically controlled by a control means. In some cases, the control means includes a control systems located in a control box.

In still a further aspect, embodiments of the present invention encompass systems and methods for providing anesthesia and ventilation in conjunction with intrathoracic pressure regulation (IPR) to a patient to enhance circulation. Exemplary systems include a circle breathing system, a gas mover, and first and second valves. A circle breathing system may include a fresh gas inlet, an inhalation uni-directional check valve, an exhalation uni-directional check valve, an absorber, a driving assembly, and tubing for providing a connection with the patient. A gas mover may include a reciprocating pump, a turbine, a centrifugal blower, a roots blower, or a venture mechanism. The gas mover may operate to remove gas from the patient, or circulate gas through the circle breathing system, or both. A first valve can be located in the circle breathing system on an inspiratory side of the circle, between the absorber and a patient fitting, and may be configured to close when the pressure in the valve reaches a set gauge pressure within a range from about −5 cm $H_2O$ to about −30 cm $H_2O$, and may be configured to prevent breathing gas from flowing in the inspiratory side of the circuit during the administration of intrathoracic pressure therapy. The second valve may be located parallel to the first valve in the circle breathing system, and may regulates a negative pressure and an amount of intrathoracic pressure regulation from about 0 cm $H_2O$ to about −30 cm $H_2O$. According to some embodiments, the second valve operates to provide a safety limit on a maximum negative pressure in the patient's breathing system. In some cases, the gas mover operates to controls the duration and slope to and from a targeted negative pressure. In some cases, the first valve and the second valve are coupled with a common housing. In some cases, the first valve, the second valve, or both, are integral components of the breathing system. In some cases, the first valve, the second valve, or both, are add-on components which can be added to the breathing system or patient airway connection.

In another aspect, embodiments of the present invention encompass systems and methods for providing anesthesia and ventilation in conjunction with intrathoracic pressure regulation (IPR) to an individual to enhance circulation. Exemplary systems may include a circle breathing system, a gas mover, and a valve. The circle breathing system may include a fresh gas inlet, inlet and outlet uni-directional valves, an absorber, and tubing for connecting with a patient. The gas mover may operate to circulate breathing gas through the circle breathing system, or remove gas therefrom. The gas mover may be located on an expiratory side of the circle, between a patient connection to the circle and the absorber. The gas mover may be configured to regulate a negative pressure and an amount of intrathoracic pressure regulation between a range from about 0 cm $H_2O$ to about −30 cm $H_2O$. The gas mover may be configured to control a duration and slope to and from a targeted negative pressure and controls an IPR pressure. The valve may be located in the circle breathing system on an inspiratory side of the circle between the absorber and a patient fitting. The valve may be configured to close when the pressure in the valve reaches a set gauge pressure that is between a range from about −5 cm $H_2O$ to about 30 cm $H_2O$. The valve may be configured to prevent breathing gas from flowing in the inspiratory side of the circuit during IPR therapy. In some cases, the valve is an integral components of the breathing system. In some cases, the valve is add-on components which can be added to the breathing system.

In another aspect, embodiments of the present invention encompass systems and methods for providing anesthesia and ventilation in conjunction with intrathoracic pressure regulation (IPR) to an individual to enhance circulation. Exemplary systems may include an open breathing system, a gas mover, and first and second valves. The open breathing system may include an inspiratory limb, an expiratory limb, a patient wye connection, an inlet valve, and an outlet valve. The gas mover may include a reciprocating pump, a turbine, a venturi, a centrifugal blower, and a roots blower. The gas mover may be configured to pull breathing gas through the expiratory limb of the open breathing system. The first valve may be located in the open breathing system on the inspiratory limb, and may be configured to close when the pressure in the first valve reaches a set gauge pressure that is within a range from about −5 cm $H_2O$ to about 30 cm $H_2O$. The first valve may be configured to prevent breathing gas from flowing in the inspiratory limb during IPR therapy. The second valve may be located parallel to the first valve in the open breathing system and may regulate a negative pressure and an amount of intrathoracic pressure regulation within a range from about 0 cm $H_2O$ to about −30 cm $H_2O$. In some instances, the second valve provides a safety limit on a maximum negative pressure in the patient's breathing system. In some instances, the gas mover operates to control a duration and a slope to and from the targeted negative pressure. In some instances, the first valve and the second valve are coupled with a common housing. In some instances, the first valve, the second valve, or both, are integral components of the breathing system. In some instances, the first valve, the second valve, or both, are add-on components which can be added to the breathing system. In some instances, the rate at which the IPR therapy is applied is controlled by the speed of the gas mover. In some instances, the gas mover is a variable speed gas mover, and the rate at which the IPR therapy is applied is controlled by varying the speed of the gas mover. In some instances, the rate at which the IPR therapy is applied corresponds to the rate at which a vacuum is generated during an expiratory phase.

In another aspect, embodiments of the present invention encompass systems and methods for providing anesthesia, mechanical ventilation, or spontaneous breathing in conjunction with intrathoracic pressure regulation (IPR) to an individual to enhance circulation, where the system returns patient expiratory gas to the ventilator or anesthesia machine. In some instances, the ventilation includes mechanical ventilation. In some instances, the ventilation includes manual ventilation. In some instances, the system may provide the capacity to create negative airway pressure during spontaneous breathing of room air or mixed gasses.

In another aspect, embodiments of the present invention encompass systems and methods for providing anesthesia or ventilation in conjunction with intrathoracic pressure regulation (IPR) to an individual to enhance circulation, where the system does not remove expiratory gas proximal to a patient wye fitting.

In another aspect, embodiments of the present invention encompass systems and methods for providing anesthesia and ventilation in conjunction with intrathoracic pressure regulation (IPR) to an individual to enhance circulation. Exemplary systems may include a circle breathing system, a spill over valve control means, a vacuum generator, and an interface mechanism. The circle breathing system may include a fresh gas inlet, inlet and outlet uni-directional valves, an absorber, and tubing to connect with a patient and with a positive pressure breath driving portion. The means for controlling a spill over valve may operate to allow the circle breathing system to be pulled sub-atmospheric up to about −30 cm $H_2O$ during an exhalation phase. The vacuum generator may operate to generate a negative pressure to set a reference pressure of the spill over valve to a sub-atmospheric pressure pneumatically. Optionally, systems may include a direct electronic controller for the spill over valve. The interface mechanism may be configured to provide an interface from the vacuum generator to a negative pressure relief assembly on a scavenger system as a reference to allow a slight negative pressure generation in the scavenger system during use. In some instances, systems may include a mechanical safety on the interface between the vacuum generator and the negative pressure relieve valve.

In another aspect, embodiments of the present invention encompass systems and methods for providing therapy to a patient. Exemplary systems may include means for intermittently delivering a positive pressure breath to an airway of the patient, and means for continuously delivering a negative pressure to the airway of the patient. Systems may also be provided as an accessory to an anesthesia system, a mechanical ventilator system, a spontaneous breathing system, or a manual ventilator system. In some cases, the means for continuously delivering a negative pressure to the airway of the patient includes a limb flow control assembly. In some cases, the limb flow assembly is present in the member as a discrete component. In some cases, the limb flow assembly is present in the member as multiple components working in concert throughout the member. In some cases, physical locations of the multiple components can be distributed throughout the member. In some cases, the means for continuously delivering a negative pressure to the airway of the patient includes a negative pressure pump, a gas mover, a turbine, a blower, a pump, a venturi, or a piston. Optionally, the member may be managed by a control box. In some cases, the control box includes a power supply and is configured to deliver controlling signals to the member. In some cases, the control box is connected with airway sensors to facilitate specific timing, including ramp up, ramp down, contour, flow targets, pressure targets, and monitoring. In some cases, the control box is configured to provide controlling signals in response to a measured parameter and a target assigned to the parameter to produce an error, which is then minimized by the control system. In some cases, the control box is configured to use an iterative process loop automatically control and adjust the IPR system to achieve targeted results. In some cases, the control box is configured to accept outside information to enable physiologic measurements or control the IPR based upon those inputs or measurements. In some cases, the control box is configured to communicate, via digital or analog signal. In some cases, the control box is configured to coordinate with external devices, physiologic monitors, and record keeping systems.

According to some embodiments, systems may further include an inspiratory limb flow control assembly that includes a threshold valve that may be passive or may be actively controlled. In some cases, the threshold valve is controlled by ON/OFF functions and by the regulation of negative pressure. In some cases, the threshold valve, in the OFF position, is bypassed and has no effect on a breathing circuit. In some cases, the threshold valve, in the OFF position, facilitates spontaneous breathing through the anesthesia breathing system. In some cases, the system is configured to operate in the beginning of an anesthesia case to pre-oxygenate the patient when the anesthesia breathing system is in bag mode. In some cases, the system is configured to allow a user to toggle the threshold valve ON or OFF and allows the user to manually adjust a desired negative pressure level setting. In some cases, the threshold valve integrates a bacterial/viral filter. In some cases, the threshold valve is created by a modified function of an already existing, controlled valve in the device. In some cases, the threshold valve is electronically or pneumatically controlled and functions of the threshold valve comprising ON/OFF, speed, timing, pressure, pressure slope, and flow rate, are controlled to facilitate regulation of negative pressure. According to some embodiments, systems may further include an inspiratory limb flow control assembly that includes a threshold valve that is controlled by a control box, where the control box provides signals, power, and coordination to the threshold valve. According to some embodiments, systems may further include a control box, where the control box is configured to operate as a user interface, a display, a connection point, a power source, a communication device, and an alarm source. According to some embodiments, systems may further include a control box, where the control box is configured to manage outside signals, data, or information to coordinate information such as patient monitoring information, lab values, settings of other devices, and output from clinical management systems, so as to automatically or interactively modify behavior or settings of the system.

According to some embodiments, systems may further include a control box, where the control box includes a processor configured to create derived information from its own measurements, calculations, control settings, and outside data or signals. According to some embodiments, systems may further include a control box, where the control box comprises a processor configured to determine a derived parameter comprising volumetric $CO_2$ or $VCO_2$ based on the patient's exhaled $CO_2$ concentration information received from an external $CO_2$ monitor and a volumetric flow information received from a turbine module. According to some embodiments, systems may further include a control box, where the control box is configured to guide a user or control or modify IPR settings of the system. According to some embodiments, systems may further include a control box configured to control IPR that is managed in multiple pressure steps in time. In some cases, IPR is controlled to provide several transitions of pressure which occur throughout a patient breath. In some cases, the multiple pressure levels in time create a sub-atmospheric airway pressure or a positive pressure in the airway during specified time intervals. In some cases, a transition from one pressure level to another is controlled to produce a controlled pressure change or slope as airway pressure is changed from one pressure level or lung volume level to another. In some cases, operation of the system provides a treatment to a patient, the treatment selected from the group consisting of increased circulation and lower intracranial pressure. In some cases, the patient is experiencing a state of low blood pressure or low circulation, such as shock, cardiac arrest, stroke, blood loss, or sepsis, which can be treated by the systems and methods disclosed herein. In some cases, the system uses feedback loops and physiological measures to alter gas flow in the system. In some cases, the physiological measure is tidal volume, inspiration pressure and volume, or end tidal carbon dioxide.

In some aspects, embodiments of the present invention encompass systems and methods for providing intrathoracic pressure regulation (IPR) to a spontaneously breathing individual. Exemplary systems may include a patient connection mechanism for coupling with an airway of the spontaneously breathing individual, and a blower mechanism configured to supply an amount of continuous negative pressure to the airway of the spontaneously breathing individual via the patient connection mechanism.

In some aspects, embodiments of the present invention encompass systems and methods for providing intrathoracic pressure regulation (IPR) to an individual. Exemplary systems include a patient connection mechanism for coupling with an airway of the individual, and a blower mechanism configured to supply an amount of continuous negative pressure to the airway of the individual via the patient connection mechanism. In certain instances, the blower mechanism is coupled with a manual bag valve mask mechanism, a mechanical ventilator machine, or an anesthesia machine. In some aspects, embodiments of the present invention encompass systems and methods for providing intrathoracic pressure regulation (IPR) to an individual. Exemplary systems may include a means for supplying an amount of continuous negative pressure to an airway of the individual. Exemplary methods may include supplying an amount of continuous negative pressure to an airway of the individual.

In another aspect, embodiments of the present invention encompass systems and methods for providing intrathoracic pressure regulation (IPR) to an individual, where systems may include a patient connection mechanism for coupling with an airway of the individual, and a blower mechanism configured to supply a negative pressure protocol to the airway of the individual via the patient connection mechanism. The blower mechanism can be coupled with a manual bag valve mask mechanism, a mechanical ventilator machine, or an anesthesia machine. In certain instances, the negative pressure protocol includes an intermittent application of negative pressure. Optionally, a manual bag valve mask mechanism, a mechanical ventilator machine, or an anesthesia machine can be configured to provide a positive pressure breath protocol to the airway of the patient. In some cases, a negative pressure protocol includes an intermittent application of individual negative pressure pulses to the airway of the individual, and a manual bag valve mask mechanism, a mechanical ventilator machine, or an anesthesia machine is configured to provide positive pressure breath pulses to the airway of the patient, such that alternating negative and positive pressure pulses are provided to the airway of the patient.

In still another aspect, embodiments of the present invention encompass systems and methods for providing intrathoracic pressure regulation (IPR) to an individual which involve a patient connection mechanism for coupling with an airway of the individual, and a negative pressure mechanism configured to supply a negative pressure protocol to the airway of the individual via the patient connection mechanism. The negative pressure mechanism may include a negative pressure pump, a gas mover, a turbine, a blower, a pump, or a piston. In some cases, the negative pressure mechanism is managed by a control box. In some instances, the negative pressure mechanism is coupled with a manual bag valve mask mechanism, a mechanical ventilator machine, or an anesthesia machine. In some instances, the control box may include a power supply and can be configured to deliver controlling signals to the negative pressure mechanism. In certain embodiments, the control box is connected with airway sensors to facilitate specific timing, pressure targets, and monitoring. In certain embodiments, the control box is configured to provide controlling signals in response to a measured parameter and a target assigned to the parameter to produce an error, which is then minimized by the control system. In certain embodiments, the control box is configured to use an iterative process loop automatically control and adjust the IPR system to achieve targeted results. In certain embodiments, the control box is configured to accept outside information to enable physiologic measurements or control the IPR based upon those inputs or measurements. In certain embodiments, the control box is configured to communicate, via digital or analog signal. In certain embodiments, the control box is configured to coordinate with external devices, physiologic monitors, and record keeping systems. According to some embodiments, the negative pressure mechanism includes a filter and a turbine. According to some embodiments, the negative pressure mechanism includes a disposable filter. According to some embodiments, the negative pressure mechanism includes a motor. According to some embodiments, the negative pressure mechanism includes a filter, a turbine, and a motor. According to some embodiments, the motor is disposed outside of an airway path provided by the negative pressure mechanism. According to some embodiments, the motor is not disposed along an airway path provided by the negative pressure mechanism.

A common feature of certain embodiments disclosed herein involves a means to provide therapeutic intrathoracic pressure regulation wherein a means is provided to fill the lungs with respiratory gases, either through spontaneous inspiration, the delivery of positive pressure ventilation, or use of a thoracic cuirass to expand the thoracic cavity followed by a means to actively extract respiratory gases from the lungs for a period of time during the expiratory phase. This generalized approach to therapeutic intrathoracic pressure regulation provides a unique means to enhance circulation to the heart and brain and other bodily organs.

In one aspect, embodiments of the present invention encompass systems and methods for providing intrathoracic pressure regulation (IPR) to an individual. Exemplary systems include a patient connection mechanism for coupling with an airway of the individual, and a flow control assembly that includes a housing having a vent, an impeller disposed within the housing, and a motor in operative association with the motor. Systems may also include an external pressure source such as a manual bag valve mask mechanism, a mechanical ventilator machine, or an anesthesia machine. The external pressure source can be in fluid communication with the housing vent of the flow control assembly. The impeller of the flow control assembly can be disposed between the patient connection mechanism and the external pressure source, along a fluid passage that extends between the patient connection mechanism and the external pressure source. The flow control assembly can be configured to allow retrograde airflow from the external pressure source to the patient connection mechanism while simultaneously compelling airflow from the patient connection mechanism to the housing vent. In some instances, the impeller of the flow control assembly is configured to produce a continuous pressure differential within a range from about 12 cm H2O to about 16 cm H2O. In some instances, the impeller of the flow control assembly is configured to produce a continuous pressure differential within a range from about 3 cm H2O to about 16 cm H2O. In some instances, the external pressure source is configured to provide a respiratory cycle duration of about 5 seconds. In some instances, operation of the flow control assembly continuously permits airflow between the patient connection mechanism and the external pressure source, without forming a physical barrier that prevents airflow therebetween. In some instances, the external pressure source is configured to maintain sub-atmospheric pressures within the thorax of a patient. In some instances, systems include a pressure sensor that monitors the patient's airway pressure between the flow control assembly and the patient. In some instances, systems include a controller device that receives information from the pressure sensor and controls operation of the flow control assembly motor based on the information.

In another aspect, embodiments of the present invention encompass systems and methods for promoting venous blood flow to the thorax of a patient. Exemplary systems include a patient connection mechanism for coupling with an airway of the individual, and a flow control assembly that includes a housing having a vent, an impeller disposed within the housing, and a motor in operative association with the motor. Systems may also include an external pressure source such as a manual bag valve mask mechanism, a mechanical ventilator machine, or an anesthesia machine. The external pressure source can be in fluid communication with the housing vent of the flow control assembly. The impeller of the flow control assembly can be disposed between the patient connection mechanism and the external pressure source, along a fluid passage that extends between the patient connection mechanism and the external pressure source. The flow control assembly can be configured to allow retrograde airflow from the external pressure source to the patient connection mechanism while simultaneously compelling airflow from the patient connection mechanism to the housing vent. In some instances, the impeller of the flow control assembly is configured to produce a continuous pressure differential within a range from about 12 cm $H_2O$ to about 16 cm $H_2O$. In some instances, the impeller of the flow control assembly is configured to produce a continuous pressure differential within a range from about 3 cm $H_2O$ to about 16 cm $H_2O$. In some instances, the external pressure source is configured to provide a respiratory cycle duration of about 5 seconds. In some instances, operation of the flow control assembly continuously permits airflow between the patient connection mechanism and the external pressure source, without forming a physical barrier that prevents airflow therebetween. In some instances, the external pressure source is configured to maintain sub-atmospheric pressures within the thorax of a patient. In some instances, systems include a pressure sensor that monitors the patient's airway pressure between the flow control assembly and the patient. In some instances, systems include a controller device that receives information from the pressure sensor and controls operation of the flow control assembly motor based on the information.

In yet another aspect, embodiments of the present invention encompass method for providing intrathoracic pressure regulation (IPR) to an individual, such methods including coupling an IPR system with an airway of the individual, and operating the system to provide therapy to the patient. For example, the IPR system hay include a housing with a vent, an impeller disposed within the housing, a motor in operative association with the motor, and an external pressure source in fluid communication with the housing vent. The impeller may be disposed between the airway and the external pressure source, along a fluid passage that extends between the airway and the external pressure source. Methods may include activating the impeller and the external pressure source, so as to allow retrograde airflow from the external pressure source to the patient while simultaneously compelling airflow from the airway to the housing vent. In some instances, methods include producing with the impeller a continuous pressure differential throughout a respiratory cycle of the individual within a range from about 12 cm $H_2O$ to about 16 cm $H_2O$. In some instances, methods include producing with the impeller a continuous pressure differential throughout a respiratory cycle of the individual within a range from about 3 cm $H_2O$ to about 16 cm $H_2O$. In some instances, methods include providing a respiratory cycle duration of about 5 seconds with the external pressure source. In some instances, methods include continuously permitting airflow between the patient connection mechanism and the external pressure source, without forming a physical barrier that prevents airflow therebetween. In some instances, methods include maintaining sub-atmospheric pressures within the thorax of a patient throughout a respiratory cycle. In some instances, methods include monitoring a patient's airway pressure between the impeller and the patient, and controlling operation of the impeller based on the monitored pressure.

In still a further aspect, embodiments of the present invention encompass methods for providing intrathoracic pressure regulation (IPR) to an individual that involve coupling an IPR system with an airway of the individual, where the IPR system includes a blower that enhances a negative pressure within the patient's lungs, and using the IPR system to manipulate respiratory gas exchange such that intrathoracic pressures during exhalation remain at or below atmospheric pressure, thereby enhancing venous blood flow back to the thorax into the heart and lungs. Methods also include periodically injecting air to the patient's lungs while simultaneously operating the blower. Further, methods may include using the IPR system to manipulate respiratory gas exchange such that intrathoracic pressures during at least a portion of an inhalation phase remain at or below atmospheric pressure.

For a fuller understanding of the nature and advantages of the present invention, reference should be had to the ensuing detailed description taken in conjunction with the accompanying drawings.

DETAILED DESCRIPTION OF THE INVENTION

Figure 1:
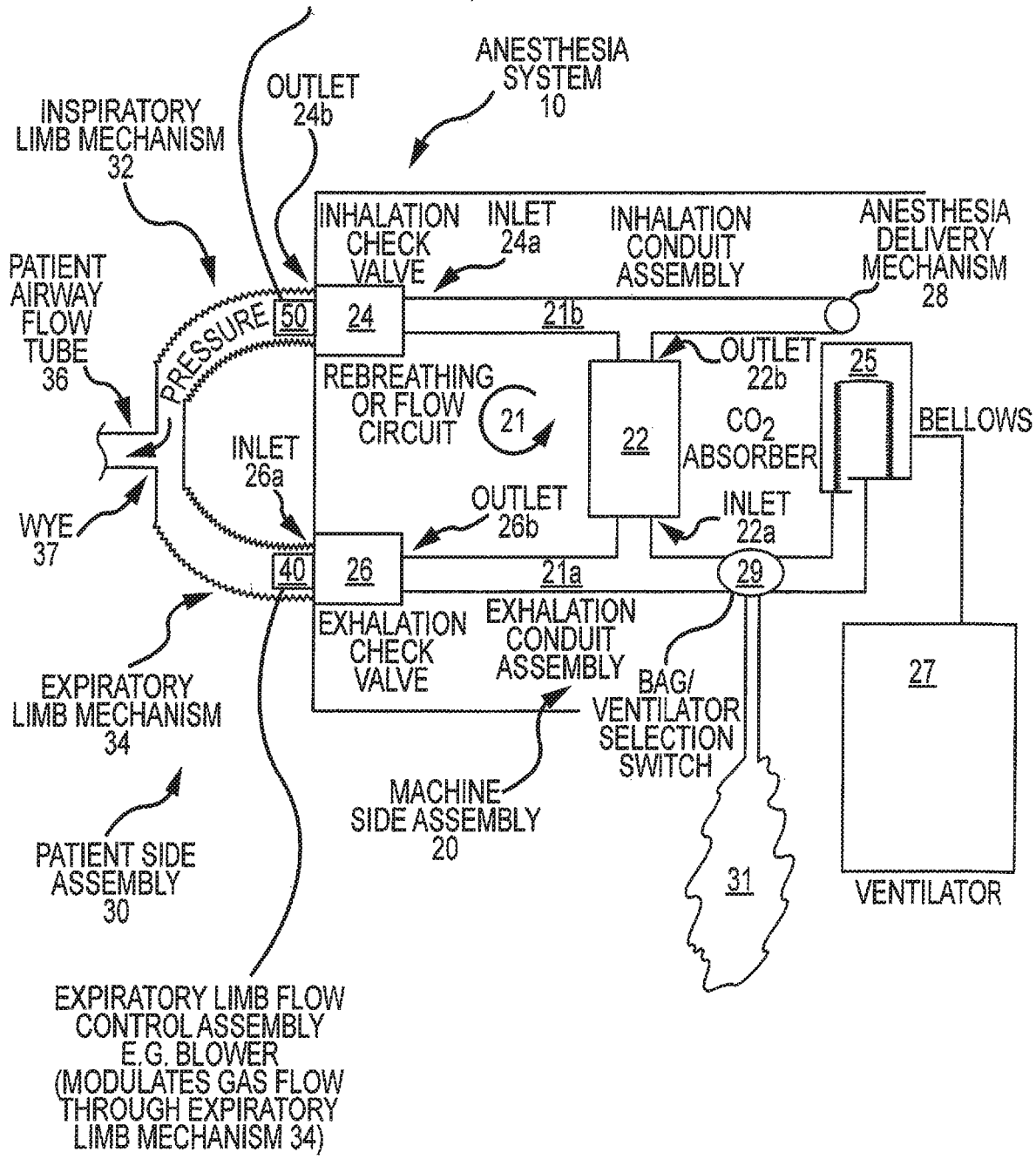
FIG. 1 illustrates aspects of an anesthesia system according to embodiments of the present invention.

Exemplary treatment techniques can provide a patient with intrathoracic pressure regulator treatment during an anesthesia regimen, spontaneous breathing, or other ventilation protocols. Optionally, such treatment techniques can provide all, or substantially all, of the respiratory gas supplied to a patient. Embodiments of the present invention encompass non-invasive approaches to regulating intrathoracic pressure and thereby increasing circulation of blood and blood pressure while simultaneously lowering intracranial pressure. In this way, circulation can be restored to a patient in a natural way. Embodiments are well suited for use in treating hypotensive (abnormally low blood pressure) patients with selected intrathoracic pressure regulation (IPR) protocols. In some cases, exemplary treatments may be administered to patients in cardiac arrest receiving cardiopulmonary resuscitation (CPR). In some cases, exemplary treatments may be administered to patients who are spontaneously breathing.

In one embodiment, a treatment system may include a negative pressure blower or constant pressure blower in combination with an intrathoracic pressure regulator, each of which are interfaced directly or indirectly with an airway of a patient, and a ventilation source. The blower may provide a continuous low-level vacuum to a breathing circuit, in conjunction with the administration of a positive pressure breath that is delivered by a ventilation source, for example an anesthesia machine, a mechanical ventilator, or a manual resuscitator. The applied negative pressure can operate to decrease the airway pressure and thus the intrathoracic pressure of the patient. When interposed between positive pressure ventilations, a decrease in intrathoracic pressure can increase vital organ perfusion and decrease intracranial pressure during states of shock, cardiac arrest, and other low blood flow states in animal studies. In some cases, the negative pressure therapy can increase blood circulation, which is useful for treating patients experiencing poor circulation, low blood pressure, or insufficient cardiac preload that may be reflected by low blood pressure.

According to some embodiments, the therapeutic techniques involve creating or modulating a negative airway pressure, while facilitating the flow of respiratory gas through a breathing circuit, without removing gas from the breathing circuit. Such approaches are particularly clinically valuable and can be implemented in an anesthesia machine (e.g. anesthesia circulator with a threshold valve), a mechanical ventilator or intensive care unit (ICU) ventilator, or in a resuscitator device such as a bag valve mask. Expiratory and inspiratory limb flow control assemblies may be provided as an auxiliary component which is configured for coupling with an existing device. Flow control assemblies may also be integrated into anesthesia systems, as well as mechanical and manual ventilation systems.

Exemplary embodiments may provide direct control of a spillover valve or bellows via an electronic solenoid valve. In some cases, the spillover valve is adjustable and can be opened or closed at any desired pressure. Related embodiments provide indirect control of a spillover valve or bellows via active control of a driving gas source during exhalation. Optionally, such control can be achieved or facilitated by operation of a vacuum source. An exemplary treatment system may include a ventilator mechanism, which may be driven by a gas assembly or a piston assembly, for example. According to some embodiments, active control of exhalation is implemented in an anesthesia machine. A gas driven ventilator or bellows can provide control of a spillover valve to allow subatmospheric pressure. In some cases, a gas driven ventilator or bellows can provide control of a driving gas to allow return of respiratory gas. Optionally, a gas driven ventilator or bellows can provide a means of controlling scavenger pressure or regulation of a vacuum level. A piston driven ventilator can provide control of a spillover valve, optionally via electronic control. In some cases, a piston driven ventilator can provide control of a piston or backstroke by means of a pressure control loop.

Turning now to the drawings, FIG. 1 illustrates an anesthesia system 10 according to embodiments of the present invention. In operation, anesthesia system 10 provides anesthesia therapy to a patient. System 10 includes a machine-side assembly 20 having a rebreathing or flow circuit 21, a carbon dioxide absorber mechanism 22, an inhalation check valve 24, an exhalation check valve 26, and an anesthesia delivery mechanism 28. As shown here, rebreathing circuit 21 includes an exhalation conduit assembly 21 a that provides or facilitates fluid communication between exhalation check valve 26 and carbon dioxide absorber mechanism 22, and an inhalation conduit assembly 21 b that provides or facilitates fluid communication between carbon dioxide absorber mechanism 22 and inhalation check valve 24. Carbon dioxide absorber mechanism 22 includes an inlet 22 a in fluid communication with exhalation conduit assembly 21 a of rebreathing circuit 21 and an outlet 22 b in fluid communication with inhalation conduit assembly 21 b of rebreathing circuit 22. Inhalation check valve 24 includes an inlet 24 a in fluid communication with outlet 22 b of carbon dioxide absorber mechanism 22 via rebreathing circuit 21. Inhalation check valve 24 also includes an outlet 24 b. Exhalation check valve 26 includes an outlet 26 b in fluid communication with inlet 22 a of carbon dioxide absorber mechanism 22 via rebreathing circuit 21. Exhalation check valve 26 also includes an inlet 26 a. Anesthesia delivery mechanism 28 is in fluid communication with rebreathing circuit 21 or anywhere in the inspiratory gas path between the patient and the anesthesia machine expiratory inlet or exhalation check valve inlet 26 a.

Anesthesia system 10 also includes a patient side assembly 30 having an inspiratory limb mechanism or inspiratory gas path 32 fluidly coupleable with outlet 24 b of inhalation check valve 24, an expiratory limb mechanism or expiratory gas path 34 fluidly coupleable with inlet 26 a of exhalation check valve 26, and a patient airway flow tube 36 or tracheal tube that provides a fluid connection between an airway or thorax of the patient and the inspiratory and expiratory limb mechanisms 32, 34. Anesthesia system 10 further includes an expiratory limb flow control assembly 40 operable to modulate gas flow through expiratory limb mechanism 34, and an inspiratory limb flow control assembly 50 operable to modulate gas flow through inspiratory limb mechanism 32. As shown in the embodiment depicted here, expiratory limb flow control assembly 40 can be disposed at or near the interface between expiratory limb mechanism 34 and exhalation check valve 26, and inspiratory limb flow control assembly 50 can be disposed at or near the interface between inspiratory limb mechanism 32 and inhalation check valve 24.

In some instances, patent side assembly 30 may include a single limb circuitry mechanism having an inner passage (e.g. outer tube) and an outer passage (e.g. inner tube) arranged in a concentric or nested fashion, wherein the outer passage or tube provides an expiratory path and the inner passage or tube provides an inspiratory path, or wherein the inner passage or tube provides an expiratory path and the outer passage or tube provides an inspiratory path. Exemplary single limb mechanisms are described in U.S. Ser. No. 12/819,959 filed Jun. 21, 2010, the content of which is incorporated herein by reference.

Expiratory limb control assembly 40 may include a reciprocating pump, a turbine, a centrifugal blower, a roots blower, a vacuum source, other means to move respiratory gases back into the anesthesia system 10, away from the patient airway tube 36, or the like. Inspiratory limb control assembly 50 can include a valve mechanism. In some instances, inspiratory limb control assembly 50 can operate to inhibit gas flow into patient airway flow tube 36 from inspiratory limb mechanism 32 when the pressure within inspiratory limb mechanism 32 is between about −5 cm $H_2O$ and about −30 cm $H_2O$. In some instances, inspiratory limb control assembly 50 can operate to allow gas flow into patient airway flow tube 36 from inspiratory limb mechanism 32 when the pressure within the inspiratory limb mechanism 32 is equal to or less than a maximum or threshold negative pressure value. According to some embodiments, the maximum negative pressure value can be between about 0 cm $H_2O$ and about −30 cm $H_2O$. Expiratory limb control assembly 40 can operate to remove gas from rebreathing circuit 21, from expiratory limb mechanism 34, or from both. In some instances, expiratory limb flow control assembly 40 operates to circulate gas within rebreathing circuit 21, away from exhalation check valve 26 and toward inhalation check valve 24. According to some embodiments, expiratory limb flow control assembly 40 can be coupled with or in operative association with expiratory limb mechanism 34. According to some embodiments, inspiratory limb flow control assembly 50 can be coupled with or in operative association with inspiratory limb mechanism 32.

Inspiratory limb flow control assembly 50 may include a valve mechanism configured to perform a series of pressure and flow regulation operations. For example, a valve mechanism can include or incorporate an impedance threshold device (ITD) such as a ResQPOD® device (Advanced Circulatory Systems Inc.). During operation of anesthesia system 10, inspiratory limb flow control assembly 50 can regulate or modulate pressure within or gas flow through inspiratory limb mechanism 32. As the patient's airway is typically in fluid communication with inspiratory limb mechanism 32 via patient airway flow tube 36, inspiratory limb flow control assembly 50 can regulate pressure or flow within the patient's thorax or airway, create or modulate a vacuum or negative pressure within the patient's chest, regulate the influx of respiratory gases into the chest, lower or modulate the intrathoracic pressure, and the like. Exemplary ITD device embodiments are described in Yannopoulos et al. "Intrathoracic Pressure Regulation Improves 24-Hour Survival in a Porcine Model of Hypovolemic Shock" Anesth. Analg. 104:157-62 (2007) and Yannopoulos et al. "Intrathoracic pressure regulation improves vital organ perfusion pressures in normovolemic and hypovolemic pigs" Resuscitation 70(3):445-53 (2006), which are incorporated herein by reference. Often, inspiratory limb flow control assembly 50 operates to modulate or regulate respiratory gas flow to the person's lungs, for example by remaining closed until a negative airway pressure within the trachea, patient airway flow tube 36, or inspiratory limb mechanism 32 achieved equals the opening or threshold pressure of the valve system. For example, in some cases the negative threshold pressure of the valve system is −12 cm $H_2O$, and hence the valve is closed so long as the airway pressure remains greater than −12 cm $H_2O$. When the airway pressure becomes equal to or more negative than −12 cm $H_2O$, the valve opens and allows flow to pass toward the patient.

To prevent or impede respiratory gases from flowing to the lungs, or to otherwise regulate flow through or pressure within the patient's airway, a variety of mechanisms such as impedance threshold devices or ITDs may be incorporated with anesthesia system 10, including those described in U.S. Pat. Nos. 5,551,420; 5,692,498; 5,730,122; 6,062,219; 6,155,257; 6,224,562; 6,234,916; 6,526,973; 6,604,523; 6,776,156; 6,986,349; 7,195,012; and 7,204,251; the complete disclosures of which are herein incorporated by reference. Hence, inspiratory limb flow control assembly 50 may also include or incorporate such ITDs or airflow regulation mechanisms. The valve systems may be configured to completely prevent or provide resistance or impedance to the inflow of respiratory gases into the patient while the patient inspires or during at least a portion of an inspiration phase or cycle. For devices or valve systems that completely prevent the flow of respiratory gases, such valves may be configured as pressure responsive valves that open after a threshold negative intrathoracic pressure has been reached.

In some embodiments, inspiratory limb flow control assembly 50 may include or be provided as a ResQPOD® impedance threshold device (Advanced Circulatory Systems, Inc., Roseville, Minn.). Exemplary inspiratory limb flow control devices can use the recoil of the chest to create a suction, and a threshold valve in the inspiratory limb flow control device 50 can be configured to open only when negative pressure threshold is exceeded (e.g. when the patient airway pressure is more negative than the negative threshold pressure of the valve). Such configurations can operate to regulate patient airway pressure, where the valve is closed until the threshold is reached.

According to embodiments of the present invention, a negative airway pressure is not created by patient chest recoil. Instead, expiratory limb flow control assembly 40 (e.g. blower or gas mover) operates to create a negative airway pressure in the patient. Relatedly, the inspiratory limb flow control assembly 40 may conduct only unidirectional flow (e.g. toward the patient), without conducting exhaled gas from the patient. Anesthesia system 10 can operate to delivery positive pressure breaths or inspiration flow to the patient, for example by pushing or delivering breathing gas through the inspiratory limb flow control assembly 50, which may involve opening a bypass valve in the inspiratory limb flow control assembly 50. In some instances, inspiratory limb flow control assembly 50 can operate to regulate the negative pressure in the inspiratory limb mechanism 32 and patient's lungs. The effect of suction produced by the expiratory limb flow control assembly 40 (e.g. blower), can also operate to pull gas through the inspiratory limb flow control device 50. Physiologically, expiratory limb flow control assembly 40 can operate to lower or regulate patient airway pressure. In some instances, the term "intra-thoracic pressure regulation" (ITPR or IPR) may refer to the physiological effect in the patient which results from operation of the expiratory limb flow control assembly 40 and inspiratory limb flow control assembly 50.

The techniques and methods disclosed herein can be applied intraoperatively, for example to treat patients that have a beating heart, but suffer from poor circulation because of blood loss or other causes. Relatedly, the techniques and methods may also be used for the resuscitation of a patient, who may arrest on the operating table or elsewhere.

Figure 1A:
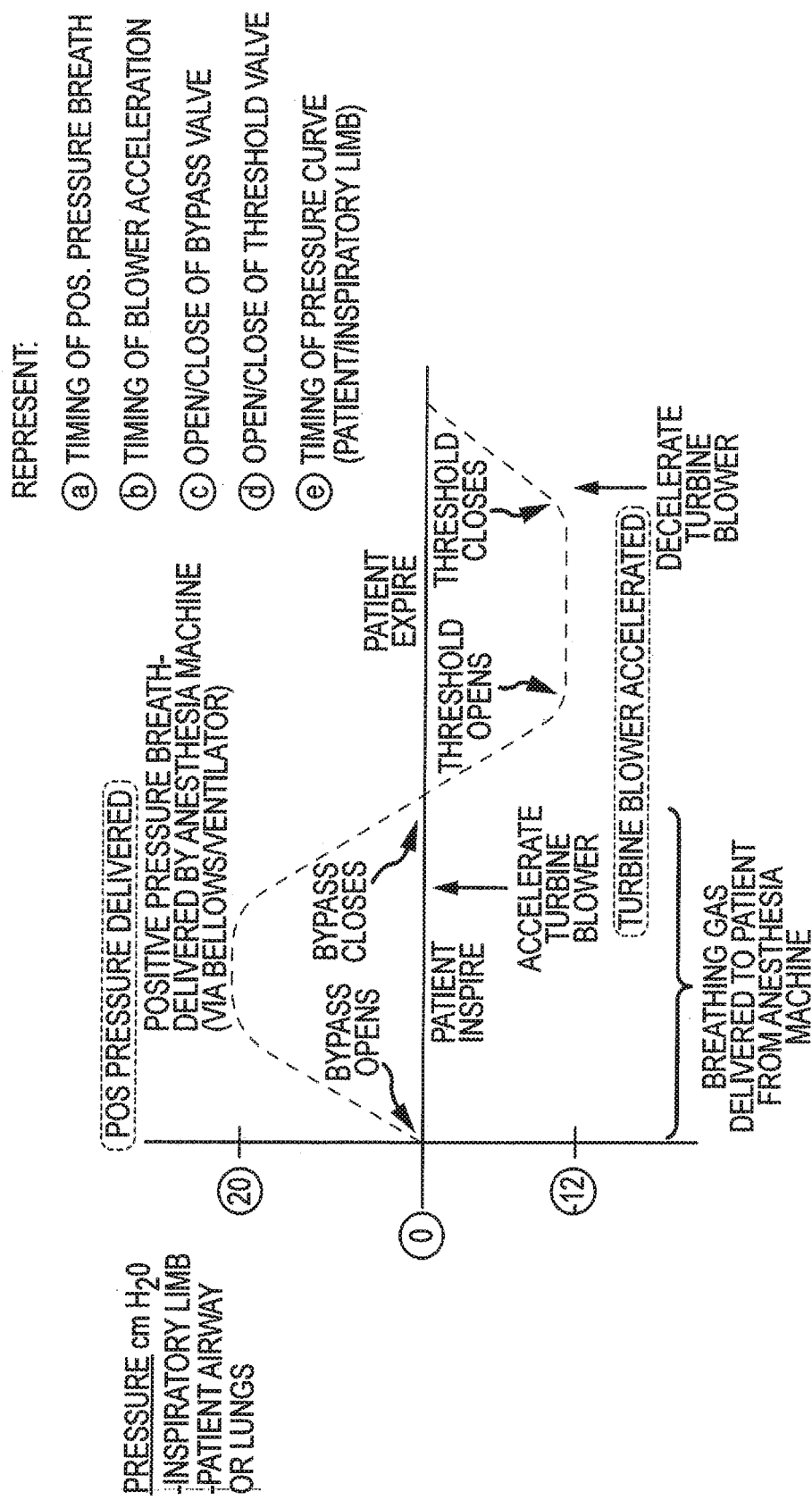
FIG. 1A illustrates aspects of patient intrathoracic or airway pressure regulation according to embodiments of the present invention.

FIG. 1A depicts a pressure curve which may be effected by operation of a treatment system according to embodiments of the present invention. As noted elsewhere herein, an inspiratory limb flow control assembly 50 may operate to perform both a bypass valve function and a threshold valve function. For example, an inspiratory limb flow control assembly may include a bypass valve subassembly and a threshold valve subassembly. This figure depicts synchronization of the two ITD valve functions (bypass, threshold), blower operation, positive pressure delivery, patient breathing, and pressure values (inspiratory limb, patient airway).

The bypass valve, located in the inspiratory limb flow control assembly 50 allows inspiratory gas to flow unimpeded toward the patient. As shown in FIG. 1A, the bypass remains open as long as pressure in the breathing circuit is zero or greater (higher). Hence, the bypass valve will bypass the threshold valve when inspiratory limb pressure is positive. This feature keeps the valve from causing interference, or creating resistance to positive pressure breaths. As soon as the breathing circuit pressure passes through zero or drops sufficiently, the bypass closes. When the bypass valve is closed, the threshold valve will regulate or limit the excursion of negative pressure in the breathing circuit. During expiratory phase, gas can flow to the patient through inspiratory limb flow control assembly 50, if the negative pressure threshold is exceeded. This occurs when the patient airway pressure becomes sufficiently negative, as depicted in FIG. 1A.

The threshold valve, located in the inspiratory limb flow control assembly 50 remains closed, thus preventing or inhibiting gas flow from anesthesia system 10 into the patient, so long as the pressure downstream (i.e. patient-side) of inspiratory limb flow control assembly 50 remains higher than the negative threshold pressure of the threshold valve. When a sufficiently negative pressure is achieved within the patient's trachea, or downstream of the inspiratory limb flow control assembly 50 for example, the threshold valve opens, thus allowing gas to flow into the patient to relieve or regulate negative pressure created by the expiratory gas mover. So long as the pressure, downstream of the inspiratory limb flow control assembly 50, is less than (i.e. more negative than) the negative pressure threshold of the threshold valve, gas may flow toward the patient. In this way, the inspiratory limb flow control assembly 50 can prevent excess negative pressure in the patient's airway and lungs.

As depicted in FIG. 1A, when the blower or turbine, which may be situated in the expiratory path or expiratory limb mechanism 34 depicted in FIG. 1, is accelerated (e.g. speeded up to create more suction in the patient circuit or patient airway flow tube 36), air pressure in the patient's lungs and in the inspiratory path or inspiratory limb mechanism 32 is pulled down (e.g. sucked out and blown into the expiratory inlet or inlet 26 a), causing the bypass valve of the inspiratory limb flow control assembly 50 to close. At this point, the threshold valve of the inspiratory limb flow control assembly 50 is in series with the inspiratory gas flow through inspiratory limb mechanism 32. As shown in FIG. 1, inspiratory limb flow control assembly 50 can be placed on outlet 24 b of machine side assembly 20 of the anesthesia system. Optionally, inspiratory limb flow control assembly 50 can be placed in any part of the inspiratory gas flow path or inspiratory limb mechanism 32, anywhere in the patient's breathing path, or anywhere in anesthesia system 10 (e.g. in machine side assembly 20) where it can operate to regulate flow through patient airway flow tube 36.

According to some embodiments, expiratory limb flow control assembly 40 (e.g. blower or turbine) operates at a constant speed, without acceleration and deceleration. In this way, expiratory limb flow control assembly 40 can provide a constant pressure source. Hence, as pressures in the circuit balance, new flow through the expiratory limb flow control assembly 40 may stop or approach zero, even though for example the blower or fan blade is still spinning The term "breathing circuit" can refer to the combined inspiratory limb mechanism 32 and expiratory limb mechanism 34 (e.g. inspiratory and expiratory gas conductors or tubes. The patient's tracheal tube or airway flow tube 36 can operate to conduct both inspiratory and expiratory gas. According to some embodiments, expiratory limb flow control assembly 40, inspiratory limb flow control assembly 50, or both, may be situated at the airway flow tube 36. For example, expiratory limb flow control assembly 40, inspiratory limb flow control assembly 50, or both, may be attached to, mounted on, connected near to, or operate within, a tracheal tube or patient airway flow tube 36.

As shown in FIG. 1, anesthesia breathing system 10 can encompass a patient side assembly 30 or patient circuit, and a machine side assembly 20 which may include a rebreathing or flow circuit 21, optionally referred to as a circle system or rebreathing system, an absorber 22, and a bellows apparatus 25. FIG. 1 also shows a wye assembly 37 of the patient circuit or patient side assembly 30. Wye 37 provides a connection between patient airway flow tube 36, inspiratory limb mechanism 32, and expiratory limb mechanism 34. In some embodiments, patient airway flow tube may be referred to as a patient breathing tube, a tracheal tube, or an endotracheal tube (ET Tube).

Anesthesia delivery mechanism 28 can provide a fresh gas connection, whereby anesthesia gas may be added to the rebreathing or flow circuit 21 or circle breathing system. A positive pressure breath can be delivered from anesthesia system 10 to the patient by pneumatically or mechanically pressing down on bellows apparatus 25. For example, positive pressure breaths can be generated by intermittently pressurizing a bellows canister of bellows apparatus 25. Typically, a ventilator mechanism 27 is provided in operative association with bellows 25. For example, a ventilator mechanism 27 can be connected with a canister outside of the bellows. When the ventilator-induced pressure on the bellows is released (e.g. during exhalation phase), the bellows rises to allow the patient to exhale. Hence, a positive pressure breath, as depicted in FIG. 1A, can be delivered to the patient based on operation of ventilator mechanism 27. Once the positive pressure bypass valve of inspiratory limb flow control assembly 50 is open, inspiratory limb flow control assembly 50 allows gas to flow from anesthesia system 10 to the patient unimpeded. According to some embodiments, as shown in FIG. 1, anesthesia system 10 may include or be in operative association with a manual ventilator bag 31. As part of a treatment, the operator can select whether to modulate flow through rebreathing circuit 21 by activating the manual ventilator bag 31 or the ventilator mechanism 27, for example by appropriately adjusting a bag/ventilator selection switch 29.

Hence, embodiments of the present invention encompass systems and methods that that reduce the amount of gas inside the patient's airway, for example by preventing or impeding gas from entering the airway, optionally in combination with removing gas from the airway, resulting in less and less air in the airway. Less air in the airway or thorax makes room for more and more blood to return to the heart. For example, this physiological concept is important during the chest recoil phase of CPR, when a reduction in intrathoracic pressure together with a reduction of air in the lungs provides a means to draw more blood back in to the thorax without resistance form the air in the thorax. The physiological concept is similarly important in states of hypovolemia, when lower intrathoracic pressures associated with a decrease in lung volumes actively draw more venous blood back to the right heart. The application of such techniques can contribute to a reduction in intrathoracic pressures, which can result in a simultaneous decrease in intracranial pressures. For example, application of these methods and devices during CPR can increase circulation to the coronary arteries during the chest wall decompression phase, and increases blood flow to the brain during the compression and decompression phases, thereby delivering more oxygen-rich blood to the brain.

Figure 2:
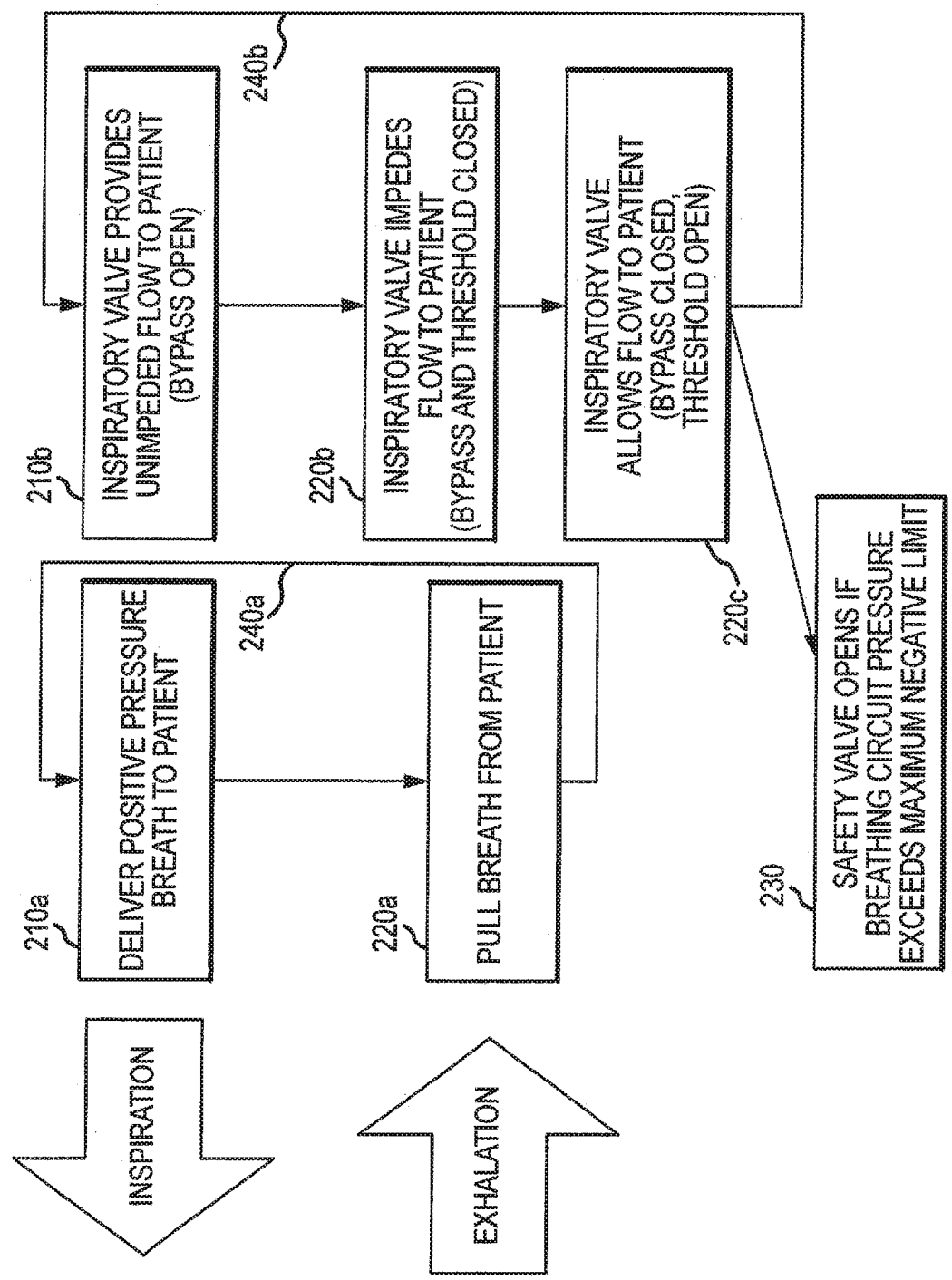
FIG. 2 illustrates aspects of a method of operation of an inspiratory limb flow control assembly or inspiratory valve mechanism such as an impedance threshold device (ITD) according to embodiments of the present invention.

FIG. 2 illustrates a method 200 of operation of an inspiratory limb flow control assembly or inspiratory valve mechanism such as an impedance threshold device (ITD) according to embodiments of the present invention. As shown in this logic flow diagram, the inspiration phase involves the step 210 *a* of delivering a positive pressure breath to the patient, which can be accomplished, for example, when the breathing circuit pressure is greater than zero. Relatedly, during the inspiration phase, or during at least a portion of the inspiration phase, the inspiratory limb flow control assembly or valve mechanism (e.g. ITD) can provide unimpeded flow to the patient as shown in step 210 *b*. For example, with reference to FIG. 1, the valve mechanism (e.g. bypass valve) may be open so as to allow gas to freely flow from machine-side assembly 20 to the patient via the inspiratory limb mechanism of patient side assembly 30. During the exhalation phase, the pressure in the breathing circuit typically drops to a value of zero or less. In response, the valve mechanism (e.g. bypass valve and threshold valve of ITD) closes as shown in step 220 *b*. Hence, during the exhalation phase, or during at least a portion of the exhalation phase, the inspiratory limb flow control assembly or valve mechanism prevents gas flow from machine-side assembly 20 to the patient via the inspiratory limb mechanism of patient side assembly 30. The exhalation phase involves the step 220 *a* of pulling a breath from the patient, for example by reducing or pulling the patient's breathing circuit pressure down to between 0 cm H2O and −12 cm H2O, Such reduction in pressure can be achieved by operation of the expiratory limb flow control assembly, which may include for example a recirculating pump mechanism, a reciprocating pump, a turbine, a centrifugal blower, a roots blower, a vacuum source, or the like. The expiratory limb flow control assembly can be configured to deliver or administer a targeted negative pressure to the breathing circuit. For example, the expiratory limb flow control assembly can be configured to deliver or administer a pressure within a range from between 0 cm H2O and −12 cm H2O. In some cases, the targeted negative pressure can be adjusted, for example based on the speed of the pump. In some cases, the expiratory limb control flow assembly can be adjusted to provide any desired pressure or range of pressures within the breathing circuit. When a negative threshold pressure is achieved with in the patient airway, the threshold valve of the inspiratory limb flow control assembly or inspiratory valve can open, as shown in step 220 *c*, thus allowing gas flow from machine-side assembly 20 to the patient via the inspiratory limb mechanism of patient side assembly 30.

In some embodiments, the inspiratory limb flow control assembly may provide a regulation mechanism whereby if negative pressure within the breathing circuit becomes too large as shown in step 230, the valve mechanism will open, thus allowing or resuming flow from machine-side assembly 20 to the patient via the inspiratory limb mechanism of patient side assembly 30. In some cases, steps 220 *c* and 230 are closely related or the same, such that the opening of the threshold valve operates to perform the safety relief function. For example, the inspiratory limb flow control assembly can be configured so that flow from machine-side assembly 20 to the patient via the inspiratory limb mechanism of patient side assembly 30 is restored or achieved when the negative pressure within the breathing circuit exceeds or becomes more negative than a threshold value. In some instances, the threshold value or design pressure can be about −12 cm H2O. This feature can provide a safety limit on the maximum negative pressure within the breathing circuit, for example by preventing the negative pressure from going too negative. Various safety valve configurations can be used to achieve this function.

Subsequently, when a new positive pressure breath is delivered by the anesthesia machine as shown by arrow 240 *a*, the bypass valve of the valve mechanism opens again as shown by arrow 240 *b*, because the inflow of the positive pressure breath pushes through the valve and circuit pressure is driven greater than zero (positive). In this way, the anesthesia system allows another free-flow inspiration. Hence, the inspiratory limb flow control assembly 50 can perform two distinct valve functions or provide two valve mechanisms, that is the bypass valve and the threshold valve, and these functions can be carried out in parallel.

Figure 3:
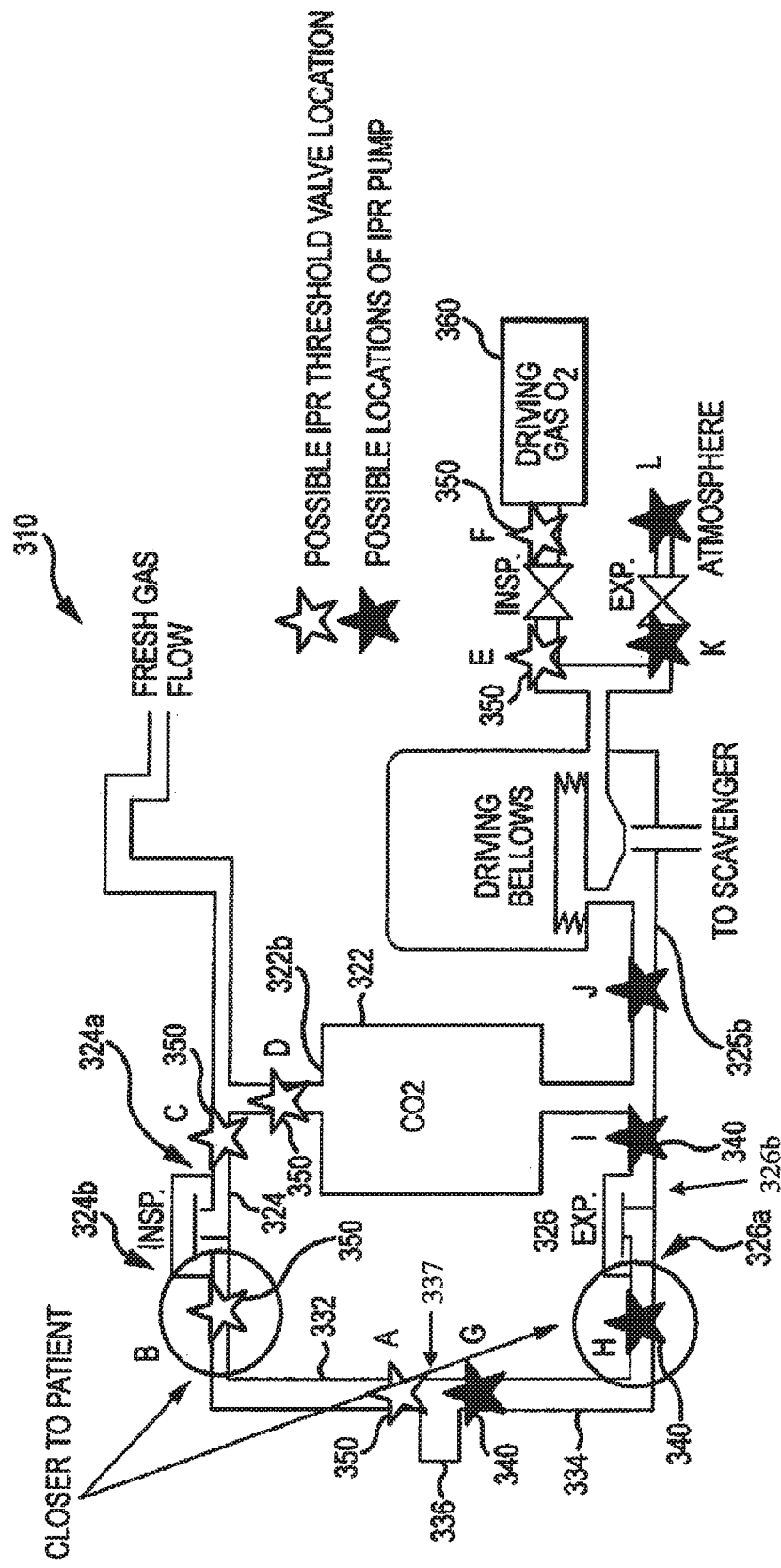
FIG. 3 illustrates aspects of an anesthesia machine according to embodiments of the present invention.

As depicted in FIG. 3, the inspiratory limb flow control assembly, the expiratory limb flow control assembly, or both, may be situated at various locations throughout an anesthesia machine breathing system. For example, an anesthesia system 310 may include an inspiratory limb flow control assembly 350 at location A (at or near patient wye 337), location B (at or near anesthesia system outlet 324 *b*), location C (at or near inhalation check valve inlet 324 *a*), location D (at or near absorber outlet 322 *b*), location E (at or near INSP between locations E and F), or location F (at or near the outlet of ventilator mechanism 360). Relatedly, anesthesia system 310 may include an expiratory limb flow control assembly 340 at location G (at or near patient wye 337), location H (at or near anesthesia system inlet 326 *a*), location I (at or near exhalation check valve outlet 326 *b*), location J (at or near driving bellows outlet 325 *b*), location K (at or near EXP between locations K and L), or location L (at or near Atmosphere, e.g. atmosphere outlet). INSP (between E and F) and INSP (between K and L) provide a valve system which allows the bellows to be pressurized and depressurized. In some instances, INSP and EXP provide intake and exhaust valves, respectively, for the bellows drive. According to some embodiments, the bellows drive gas is vented to the atmosphere. This is not the same as the patient breathing gas, which is on the other side of the bellows. The drive gas, from the ventilator, is used to squeeze the breathing gas into the patient's lungs. In this way, the ventilator can drive the circle breathing system.

Hence, a negative pressure blower or expiratory limb flow control assembly 340, can be positioned near a one-way exhalation valve 326 on an expiratory limb mechanism 334. For example, expiratory limb flow control assembly 340 may be coupled with inlet 326 a of the exhalation valve 326. Expiratory limb flow control assembly 340 operates to pull gas from the patient connection or airway flow tube 336, and can also operate to pull gas from the inspiratory limb mechanism 332, or the inspiratory side of the breathing circuit. Operation of the expiratory limb flow control assembly 340 combines those two gases, and runs them through the expiratory one-way valve 326. Thereafter, the combined gases are transmitted into the $CO_2$ container or absorber 322, and subsequently delivered out the inhalation check valve 324, and toward the patient. In this way, the expiratory limb flow control assembly 340 or negative pressure blower can push or force gas into or toward the expiratory inlet 326 a, and can also pull gas from the breathing circuit, while the inspiratory limb flow control assembly 350 performs a regulatory or threshold function for gas flowing through inspiratory outlet 324 b.

According to some embodiments, as the speed of the negative pressure blower turbine or expiratory limb flow control assembly 340 increases, the amount of suction within the patient side assembly increases, thus reducing the pressure therein, thereby causing a threshold valve of inspiratory limb flow control assembly 350 to close. In some cases, the inspiratory limb flow control assembly 350 can operate, in conjunction with the expiratory limb flow control assembly 340, to produce a threshold resistance within a range from about −10 cm $H_2O$ to about −12 cm $H_2O$. Hence, when the pressure within the patient side assembly is reduced enough to reach this threshold, the threshold valve opens, thus allowing gas flow from the anesthesia system 310 and into the patient. According to some embodiments, as the expiratory limb flow control assembly 340 operates (e.g. the turbine spins), it pushes gas into the expiratory inlet 326 a, and pulls gas from the patient, down to a −12 cm $H_2O$ pressure level, at which point the check valve opens up, thus allowing continuous circulation of gases in the $CO_2$ container or absorber 322. Hence, in some cases no gas is withdrawn from the breathing circuit by the anesthesia system 310, but rather the gas is recirculated. According to some embodiments, as the next breath from the ventilator 360 occurs, the bellows are pushed downward, thus squeezing the bag in the bellows box, thereby producing an overpressure in both the inspiratory and the expiratory sides of the circuit, which then forces air into patient's airway, based on the displacement of the driving bellows. As this ventilation operation occurs, the blower is running at a constant speed, thus allowing the recirculation of gases. In some instances, an expiratory limb flow control assembly 340 may include a pump, a blower, a piston, a gas move, or the like. In some instances, expiratory limb flow control assembly 340 may include an electrically operated turbine.

In some cases, anesthesia system 310 may not include an inspiratory limb flow control assembly 350. In such cases, expiratory limb flow control assembly 340 (e.g. a turbine) can operate to push or pull gas into the expiratory inlet 326 a, facilitating advancement of gas into and through the $CO_2$ container or absorber 322, and out through inhalation check valve 324 toward the patient, thus completing the circuit and providing a continuing circulation.

Placement of inspiratory limb flow control assembly 350 on inspiratory limb mechanism 332 near anesthesia system outlet 324 b can operate to restrict the flow going to the patient. Hence, expiratory limb flow control assembly 340 (e.g. blower) pulls gas from the patient's lungs, increasing the magnitude of patient airway negative pressure until that pressure reaches the opening threshold of the inspiratory limb flow control assembly 350, in which case the threshold valve of inspiratory limb flow control assembly 350 opens. As shown in FIG. 3, expiratory limb flow control assembly 340 and inspiratory limb flow control assembly 350 can be positioned at various locations throughout the anesthesia system 310, and hence can be integral to a machine side assembly, or to a patient side assembly. Optionally, expiratory limb flow control assembly 340, inspiratory limb flow control assembly 350, or both, may be provided as discrete components.

According to some embodiments, expiratory limb flow control assembly 340 (e.g. blower) is configured to operate at a low level or speed, or inspiratory limb flow control assembly 350 can be operated in such a way, so that operation of the expiratory limb flow control assembly 340 and inspiratory limb flow control assembly 350 does not produce a negative airway pressure. The anesthesia system can be configured to function in this capacity for any desired period of time. When the action of the expiratory limb flow control assembly 340 is increased (e.g. fan speed increased), and/or threshold resistance is introduced by inspiratory limb flow control assembly 350 (e.g. closing the valve), however, the anesthesia system can operate to generate or amplify negative airway pressure in the patient. For example, operation of assemblies 340 and 350 may produce not negative pressure, unless or until closure of a valve in assembly 350 operates to produce negative pressure at the patient connection. In some cases, assembly 340 can be controlled actively (e.g. turned on and off), instead of operating passively. Such active control can be used with assembly 340, regardless of where it may be positioned throughout the anesthesia system.

Operation of either or both of the expiratory limb flow control assembly 340 and inspiratory limb flow control assembly 350 can be controlled by automatic means. In some instances, operation of expiratory limb flow control assembly 340 and/or inspiratory limb flow control assembly 350 can be controlled based on pneumatic signals or electric signals. In some cases, assemblies 340 and 350 may each be provided as a single system. In other cases, assembly 340, assembly 350, or both, may each be provided as a collection of multiple subsystems, where each subsystem is positioned at a different location throughout the anesthesia system. For example, a flow control assembly may include a pressure sensor in one location, and a step motor control threshold resistor in another location.

Embodiments of the present invention also encompass treatment system having a physical threshold valve or means for providing equivalent functionality created by the function or interaction of breathing circuit controlling valve or valves, such as threshold valves shown in various positions in FIG. 3.

Figure 4:
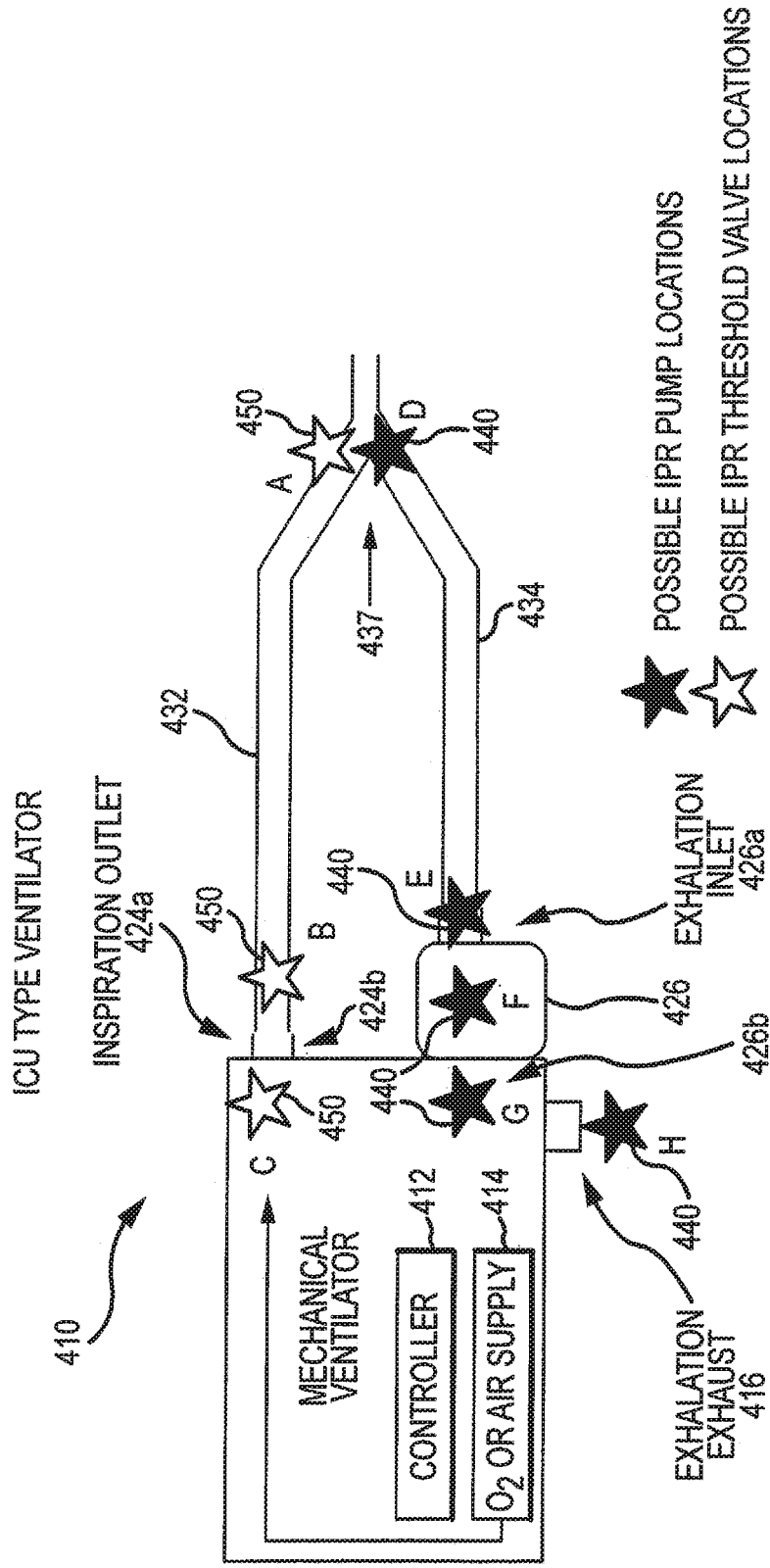
FIG. 4 illustrates aspects of a ventilator machine according to embodiments of the present invention.

As shown in FIG. 4, an inspiratory limb flow control assembly, an expiratory limb flow control assembly, or both, may be situated at various locations throughout a ventilator system 410, including in an anesthesia machine, such as an intensive care unit (ICU) ventilator or a transport type mechanical ventilator. For example, an anesthesia system 410 may include an inspiratory limb flow control assembly 450 at location A (at or near patient wye 437), location B (at or near ventilator system outlet 424 *b*), or location C (at or near inhalation check valve inlet 424 *a*). Relatedly, ventilator system 410 may include an expiratory limb flow control assembly 440 at location D (at or near patient wye 437), location E (at or near ventilator system inlet 426 *a*), location F (at or near exhalation check valve 426), location G (at or near exhalation check valve outlet 426 *b*), location H (at or near exhalation exhaust or atmosphere outlet 416). As shown here, ventilator system 410 may include a controller 412 and an oxygen or air supply mechanism 414.

In some instances, a patent side assembly of ventilator system 410 may include a single limb circuitry mechanism having an inner passage (e.g. outer tube) and an outer passage (e.g. inner tube) arranged in a concentric or nested fashion, wherein the outer passage or tube provides an expiratory path and the inner passage or tube provides an inspiratory path, or wherein the inner passage or tube provides an expiratory path and the outer passage or tube provides an inspiratory path. Exemplary single limb mechanisms are described in U.S. Ser. No. 12/819,959 filed Jun. 21, 2010, the content of which is incorporated herein by reference.

In operation, gas from $O_2$ or air supply mechanism 414 is delivered to the patient via inspiratory limb mechanism 432, and gas from the patient (optionally combined with gas from limb mechanism 432) is transmitted away from patient via expiratory limb mechanism 434. A ventilator system may also include pressure and volume monitoring devices, control systems, and alarm systems, and limb flow assemblies 440 and 450 can be configured to operate in conjunction with such monitoring, control, and alarm systems.

According to some embodiments, expiratory limb flow control assembly 440 can operate to lower the expiratory resistance of the ventilator. As shown in FIG. 4, limb flow control assemblies 440, 450 can be placed in various locations located either internal to or external to the ventilator device. In some instances, either or both of limb flow control assemblies 440, 450 can be placed where the ventilator body or casing connects with the patient circuit. In some instances, either or both of limb flow control assemblies 440, 450 can be placed between the patient circuit and the wye apparatus 437. Optionally, either or both of limb flow control assemblies 440, 450 can be placed between the patient and the wye. In some instances, inspiratory limb flow control assembly 450 includes a physical valve. In some cases, inspiratory limb flow control assembly 450 includes an electronic valve that at least partially controls flow to the patient.

Controller 412 can be programmed to, or contain instructions for, effecting any of a variety of treatment protocols. For example, controller 412 can be programmed to deliver instructions to the ventilator for delivering normal positive pressure breaths. In some instances, ventilator system 410 may include a bacterial filter (e.g. at or near exhalation check valve 426).

As shown in FIG. 4, inspiratory limb flow control assembly 450 (e.g. threshold valve) and expiratory limb flow control assembly 440 can be positioned in any of a variety of positions throughout system 400. Means for providing equivalent functionality to that of either or both of limb flow control assemblies 440, 450, optionally for generating IPR, can be created by existing valves or devices within the ventilator design, either as discreet devices or via the interaction of multiple valves and/or pumps.

Figure 5:
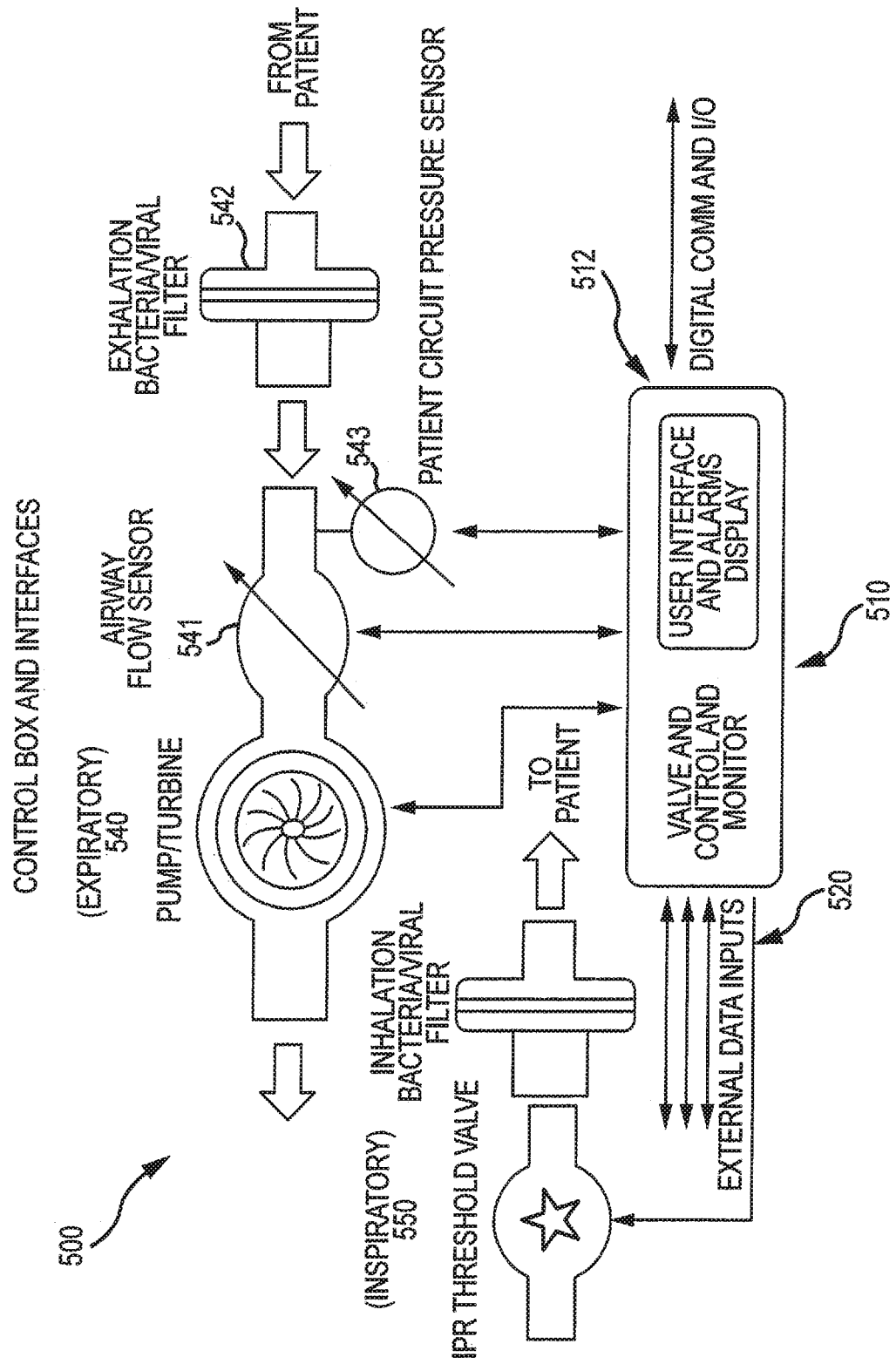
FIG. 5 illustrates aspects of an anesthesia system or ventilator system, which may include or be in operative association with a controller or control assembly, according to embodiments of the present invention.

FIG. 5 illustrates aspects of an anesthesia system or ventilator system 500, which may include or be in operative association with a controller or control assembly, according to embodiments of the present invention. As shown here, anesthesia or ventilator system 500 includes an expiratory limb flow control assembly 540 (e.g. pump or turbine) and an inspiratory limb flow control assembly 550 (e.g. ITD device). Anesthesia system or ventilator system 500 may be configured so that expiratory limb flow control assembly 540 is in fluid communication with an airway flow sensor 541. Anesthesia or ventilator system 500 may also include a bacterial and/or viral exhalation filter 542 which receives and filters gases from the patient airway flow tube (optionally in combination with gases from the inspiratory limb mechanism), and a patient circuit pressure sensor 543 that senses pressure within the expiratory limb mechanism. Information or data from flow sensor 541, pressure sensor 543, or both, can be used to regulate operation of expiratory limb flow control assembly 540.

According to some embodiments, when the pressure regulation activity of expiratory limb flow control assembly 540 operates to close a threshold valve of inspiratory limb flow control assembly 550, this can effectively operate to close the anesthesia or ventilator machine off from the patient. In some cases, patient airway pressure can be measured at this time. For example, operation of a turbine may reduce the airway pressure down to about −10 cm H2O, and patient circuit pressure sensor 543, which is in fluid communication with the patient side assembly, or otherwise on the patient side of the expiratory limb flow control assembly 540, can effectively operate to measure airway pressure in the patient circuit. Further, airway flow sensor 541, which is in fluid communication with the patient side assembly, or otherwise on the patient side of the expiratory limb flow control assembly 540, can effectively operate to measure airway flow in the patient circuit. As shown here, airway pressure sensor 543 can be disposed between the expiratory limb flow control assembly 540 (e.g. turbine) and the patient. In some instances, a blower mechanism may be operated continuously, and/or during a period in which an inspiratory valve is closed. Surprisingly, such techniques may consume less power than otherwise previously believed.

Anesthesia or ventilator system 500 includes a controller assembly 510 which can transmit instructions to and receive data from each of expiratory limb flow control assembly 540, airway flow sensor 541, and patient circuit pressure sensor 543. Anesthesia or ventilator system 500 may also include a power supply, or means for connecting with a power supply. For example, means for connecting with a power supply may include an electrical cord or a battery. In some cases, controller assembly 510 may include a user interface, an alarm, and a display. Optionally, controller assembly 510 may include an input/output mechanism 512 for transmitting and receiving digital communications. As shown here, controller assembly 510 can be in operational connectivity with inspiratory limb flow control assembly 550 by way of an external data input mechanism 520. According to some embodiments, controller assembly 510 can be configured to provide control instructions to expiratory limb flow control assembly 540. According to some embodiments, controller assembly 510 can be configured to receive data or information from airway flow sensor 541, patient circuit pressure sensor 543, or both. Controller assembly 510 may include a processor which determines instructions for expiratory limb flow control assembly 540, optionally based on input data received from airway flow sensor 541, patient circuit pressure sensor 543, or both. Controller assembly 510 may also be configured to display information regarding the status of anesthesia or ventilator system 500 to a user or operator. For example, controller assembly 510 can be configured to airway flow and patient circuit pressure information or data on a display screen for viewing by the operator.

Figure 6:
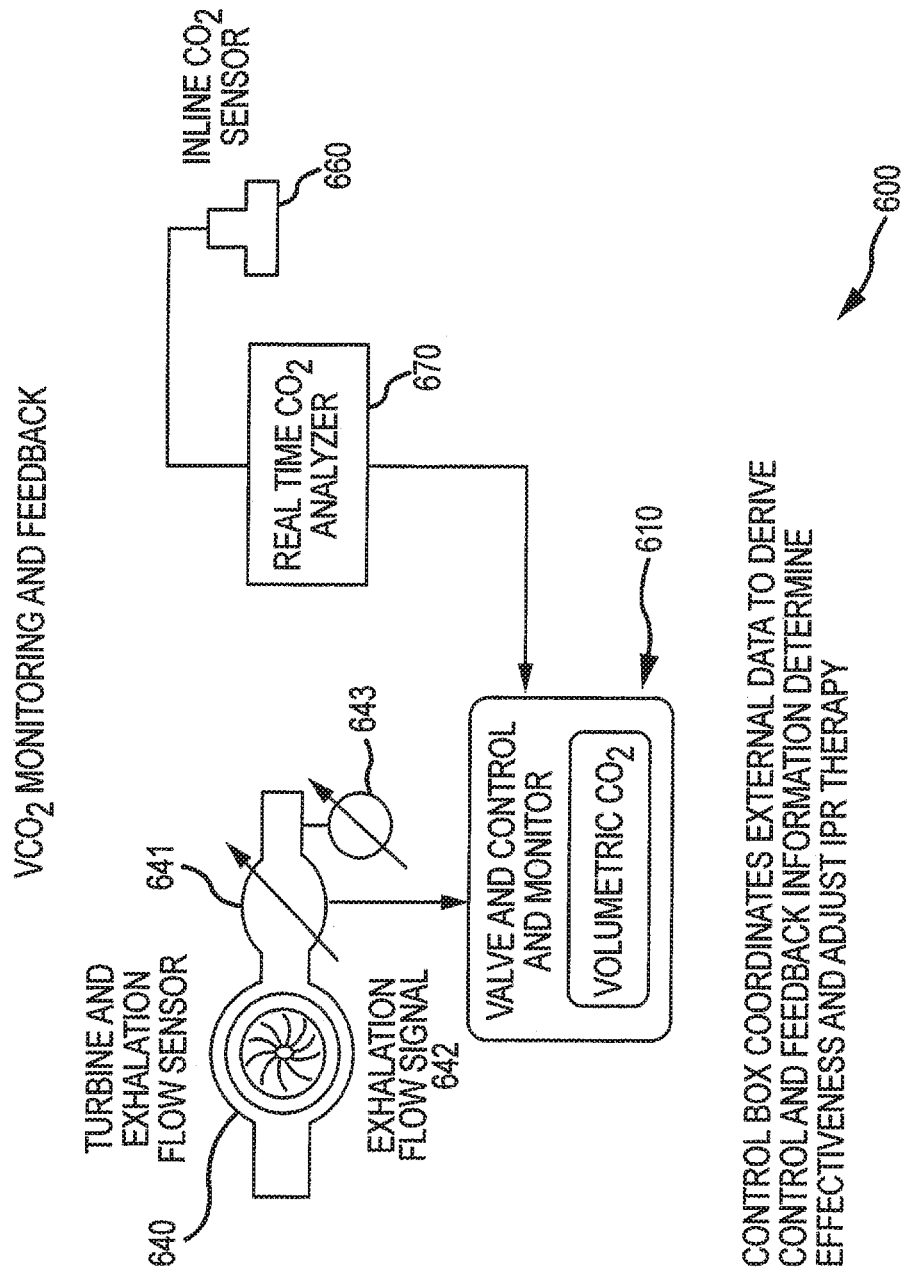
FIG. 6 illustrates aspects of an anesthesia system or ventilator system, which may include or be in operative association with a controller or control assembly, according to embodiments of the present invention.

FIG. 6 illustrates aspects of an anesthesia system or ventilator system 600, which may include or be in operative association with a controller or control assembly, according to embodiments of the present invention. As shown here, anesthesia or ventilator system 600 includes an expiratory limb flow control assembly 640 (e.g. pump or turbine) and an inspiratory limb flow control assembly (not shown). Anesthesia system or ventilator system 600 may be configured so that expiratory limb flow control assembly 640 is in fluid communication with an exhalation airway flow sensor 641. Anesthesia or ventilator system 600 may also include a patient circuit pressure sensor 643 that senses pressure within the expiratory limb mechanism. Information or data from flow sensor 641, for example an exhalation flow signal 642, can be transmitted to controller assembly 610. Anesthesia or ventilator system 600 may also include an in line carbon dioxide sensor 660, which may be in a patient's airway or in fluid communication therewith, coupled with a real-time carbon dioxide analyzer mechanism 670 that can transmit information to controller assembly 610. In use, the carbon dioxide sensor 660 can measure the concentration of carbon dioxide in the patient, and the exhalation flow sensor 641 can measure gas flow entering or flowing toward the expiratory limb flow control assembly 640. The controller assembly 610 can include a processor that determines volumetric carbon dioxide, for example based on the product of the carbon dioxide concentration and expiratory flow value. The controller assembly 610 can also display the value of the volumetric carbon dioxide measurement to the user or operator. In some cases, the volumetric carbon dioxide measurement can be used to adjust or control operation of the expiratory limb flow control assembly 640. In this way, anesthesia system or ventilator system 600 can operate to provide volumetric carbon dioxide monitoring and feedback functions.

Figure 7:
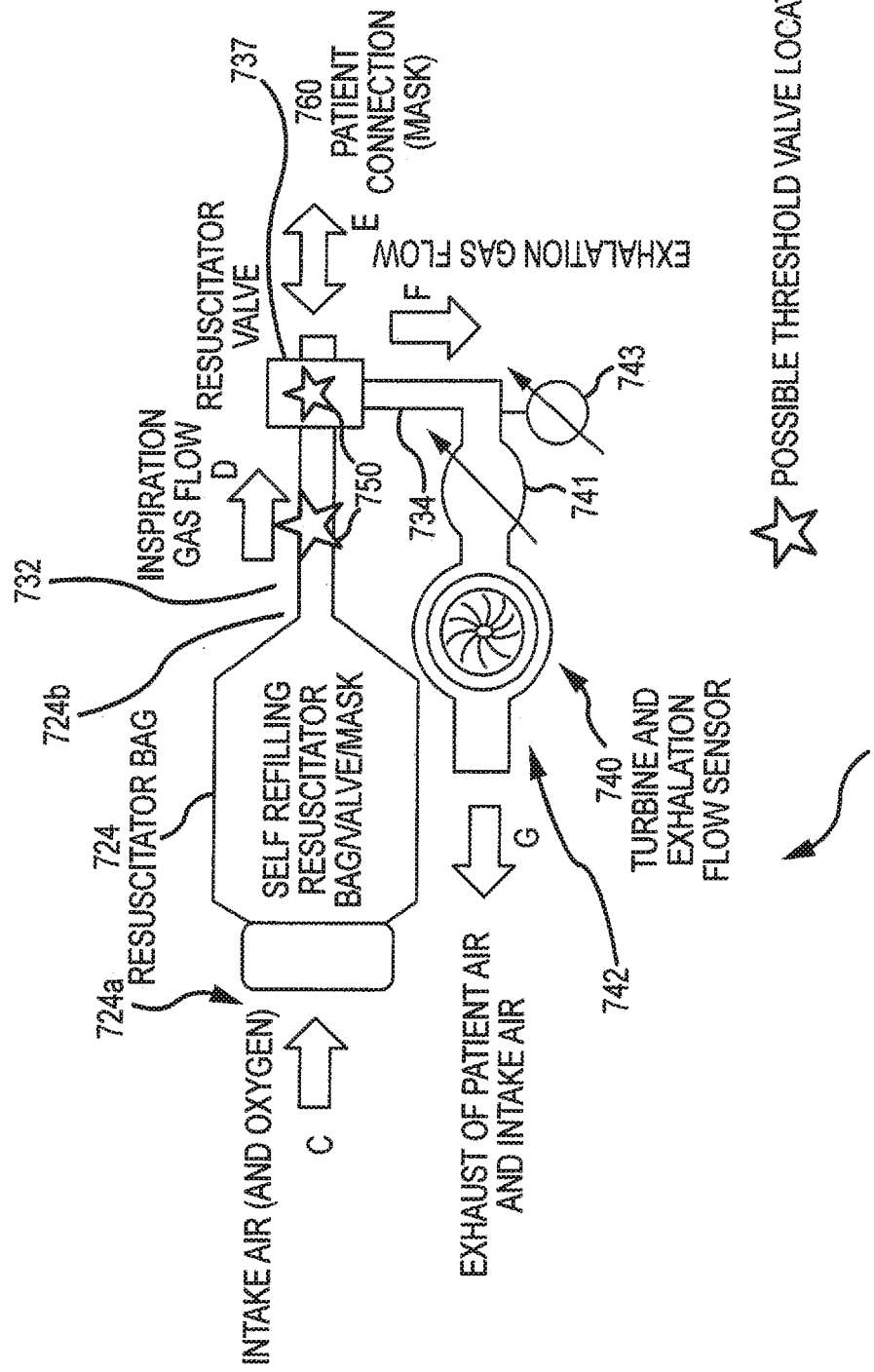
FIG. 7 illustrates aspects of a manual ventilator system according to embodiments of the present invention.

FIG. 7 illustrates aspects of a manual ventilator system 700 according to embodiments of the present invention. Manual ventilator system 700 can be configured as a bag valve mask device, and can be used to deliver intrathoracic pressure regulation treatment to a patient. For example, emergency medical personnel may carry a manual ventilator system 700 in an ambulance, and use the system on a patient who is in cardiac arrest, or on a patient in hemorrhagic shock from blood loss. As depicted here, manual ventilator system 700 includes a resuscitator bag 724 having an inlet 724 *a* which receives intake air, with ambient or supplemental oxygen, as indicated by arrow C, and an outlet 724 *b* that is in fluid communication with an inspiratory limb mechanism 732. Upon compression of bag 724, such air is delivered toward the patient through inspiratory limb mechanism 732, as indicated by arrow D (inspiration gas flow). Manual ventilator system 700 can be used as a bag valve mask for emergent care applications.

Manual ventilator system 700 also includes an expiratory limb flow control assembly 740 (e.g. pump or turbine) and an inspiratory limb flow control assembly 750 (e.g. ITD device). Expiratory limb flow control assembly 740 operates to withdraw gas from, or reduce pressure within, expiratory limb mechanism 734. As shown here, manual ventilator system 700 further includes a patient connection 760 such as a mask or flow tube. Inspiratory and expiratory gases can be exchanged between the patent and manual ventilator system, as indicated by arrow E. Wye 737 provides a connection between patient connection 760, inspiratory limb mechanism 732, and expiratory limb mechanism 734. In operation, expiratory limb flow control assembly 740 receives gases from the patient by way of the patient connection 760 or mask, optionally in combination with gases from the inspiratory limb mechanism 732. Accordingly, such gases are transmitted away from the patient through expiratory limb mechanism 734, as indicated by arrow F (exhalation gas flow). Such patient air and intake air can then be exhausted through an outlet 742 of expiratory limb flow control assembly 740, as indicated by arrow G.

Anesthesia system or ventilator system 700 may be configured so that expiratory limb flow control assembly 740 is in fluid communication with an airway flow sensor 741. Manual ventilator system 700 may also include a patient circuit pressure sensor 743 that senses pressure within the expiratory limb mechanism. Information or readings from flow sensor 741, pressure sensor 743, or both, can be used to regulate operation of expiratory limb flow control assembly 740. In some cases, inspiratory limb flow control assembly 750 can be positioned on manual ventilator system 700 at location A (at or near patient wye 737), or at location B (at or near resuscitator bag outlet 724 *b*.

By placing the expiratory limb flow control assembly 740 in fluid communication with the resuscitator bag 724, it is possible to provide a negative phase capability to the anesthesia system or ventilator system 700, and thus system 700 can be used to deliver a positive pressure ventilation to a patient, in combination with delivering a negative pressure therapy treatment to the patient.

In some instances, a patent side assembly of ventilator system 700 may include a single limb circuitry mechanism having an inner passage (e.g. outer tube) and an outer passage (e.g. inner tube) arranged in a concentric or nested fashion, wherein the outer passage or tube provides an expiratory path and the inner passage or tube provides an inspiratory path, or wherein the inner passage or tube provides an expiratory path and the outer passage or tube provides an inspiratory path. Exemplary single limb mechanisms are described in U.S. Ser. No. 12/819,959 filed Jun. 21, 2010, the content of which is incorporated herein by reference.

Figure 8:
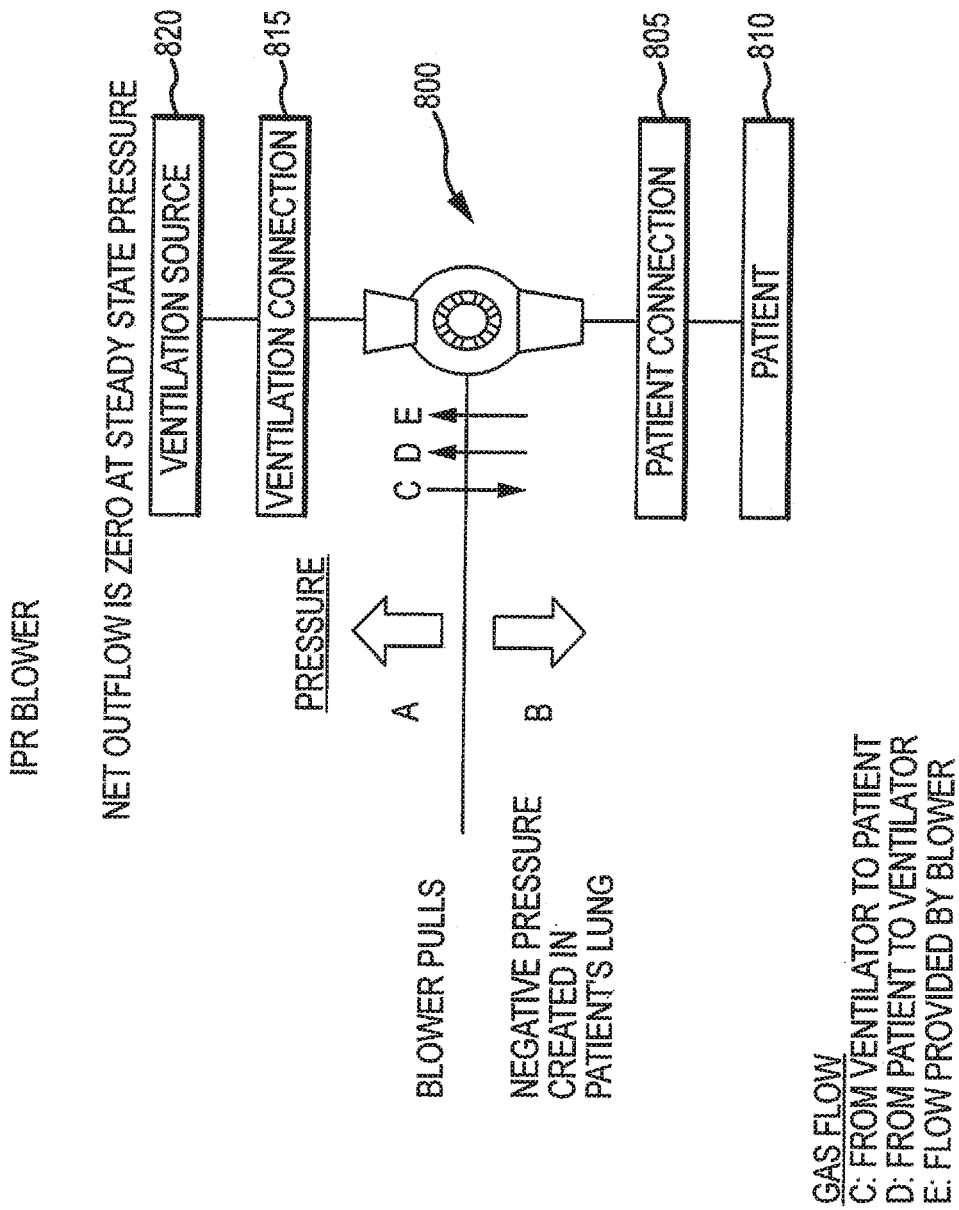
FIG. 8 depicts aspects of a blower mechanism according to embodiments of the present invention.

In some embodiments, a single mechanism or system can be used to modulate flow or regulate negative pressure within the patient airway, inspiratory limb mechanism, expiratory limb mechanism, and rebreathing circuit. FIG. 8 shows an example of an intrathoracic pressure regulation (IPR) blower mechanism 800 which can be used to perform such functions. In some cases, blower mechanism 800 is provided as a centrifugal blower. Blower mechanism 800 may operate as a pressure generator or modulator, and can be used to create a controlled pressure between the patient and the ventilation device (e.g. anesthesia machine, mechanical ventilator, bag valve mask, and the like). In some cases, the pressure provided by blower mechanism 800 can be referred to as $\Delta P$. When blower mechanism 800 is in fluid communication with the patient's airway or mouth, which may be accomplished using a mask, tube, or similar device, blower mechanism 800 operates to pull air or gas from the patient's lungs until a set or desired pressure is achieved. When the pressure in the lungs reaches the blower pressure, blower mechanism 800 is in equilibrium and the net flow is zero, and a steady state pressure is achieved. Hence, a patient attached to blower mechanism 800 may inspire, at a pressure in excess of the blower pressure ΔP, and pull in a breath. Subsequently, when exhalation begins, that breath will be exhaled, by virtue of the patient's lung recoil and the pressure of the IPR blower mechanism 800 until, once again, equilibrium is achieved. In some instances, operation of blower mechanism 800 assists exhalation and can be used in patient populations that benefit not only from IPR but also from enhanced exhalation (e.g. asthma, COPD, and the like). In this way, operation of blower mechanism can remove gas from the breathing system until a threshold pressure is achieved, as a results of the pressure regulation activity of blower mechanism 800. As shown here, blower mechanism is connected between a patient 810 and a ventilation source or device 820. Hence, operation of blower mechanism 800 or activity of patient 810 does not unduly disturb the behavior of the ventilator or anesthesia machine 820. Accordingly, blower mechanism 800 can be used in a contiguous way, for example with a spontaneously breathing patient, during an intubation process, or with any ventilation platform. As shown here, patient connection 805 may include a mask, an airway tube, a tracheal tube, or the like. During operation of blower mechanism 800, patient can breathe spontaneously through blower mechanism 800.

As shown in FIG. 8, during operation the blower mechanism 800 operates to pull gas, for example at a controlled pressure, from the patient, as indicated by arrow A. Here, the output of the blower mechanism 800 is directed toward or through the ventilation device connection 815. The blower mechanism can be configured to create a differential pressure ΔP, for example as a result of a spinning centrifugal blower. In some cases, the speed of the blower determines the differential pressure level. In some cases, the differential pressure can be adjustable, for example throughout a range that extends from 0 cm $H_2O$ to −20 cm $H_2O$. As indicated by arrow B, negative pressure is created at the patient's airway. When the pressure of arrow A and the pressure of arrow B are equivalent, the net flow through the blower mechanism 800 is zero. A positive pressure breath provided by the ventilation source 820 need only overcome the blower pressure, in order to deliver a breath to the patient. In this way, blower mechanism 800 operates as both a pressure valve and a negative pressure source.

In operation, it is possible to bi-directionally move gas through blower mechanism 800. For example, a positive pressure from the ventilation source can move gas through blower mechanism 800 toward the patient as indicated by arrow C, and exhalation gas from the patient can move through blower mechanism 800 toward the ventilation system as indicated by arrow D. Blower mechanism 800 may also operate, for example by way of a centrifugal blower, to move gas from the patient side toward the ventilator side, as indicated by arrow E. Hence, the ventilation mechanism 820 can push gas against the expiratory outflow and toward the patient, for example during the exhalation phase. During inhalation, the which may involve a spontaneous patient breath or a positive pressure breath provided by an anesthesia machine, ventilator, or bag valve mask, ventilation mechanism 820 can operate to push gas through the turbine, overcoming the pressure provided by the turbine, resulting in a net flow of gas through blower mechanism 800 and into the patient.

Relatedly, blower mechanism 800 may operate as a pressure generator turbine or pressure source assembly. For example, blower mechanism 800 can create a negative intrathoracic pressure in the patient, and also provide a conduit for the delivery of a positive ventilation from ventilator source 820 to the patient. In some cases, blower mechanism 800 includes a variable torque fan assembly. In some cases, as gas from the ventilator flows through blower mechanism 800 toward the patient, opposite the direction of flow of the blower itself, the blower mechanism continues to operate. For example, a turbine fan of blower mechanism 800 may continue to spin in a direction which would otherwise provide a net flow of gas from the patient to the ventilator, however due to pressure from the ventilator, the net flow across blower mechanism is toward the patient, instead of away from the patient. As such, blower mechanism 800 may be considered to operate as a pressure source, and it is possible to overcome that pressure source, for example by operation of the ventilator, so as to move gas in a contra-flow direction through blower mechanism and toward the patient.

Hence, according to some embodiments, operation of a turbine fan of blower mechanism 800 acts to pull gas out of and away from the patient at a particular ΔP. While blower mechanism 800 is delivering ΔP, however, the intrathoracic pressure can be regulated by other factors, such as with an impedance threshold device (e.g. an ITD such as that disclosed in U.S. Pat. Nos. 5,551,420; 5,692,498; 5,730,122; 6,062,219; 6,155,257; 6,224,562; 6,234,916; 6,526,973; 6,604,523; 6,776,156; 6,986,349; 7,195,012; and 7,204,251; incorporated herein by reference), or by operation of the blower itself in response to positive pressure provided by a ventilator. Typically, the turbine runs at a characteristic speed, and blower pressure ΔP is approximately proportional to the speed. In some instances, blower mechanism 800 provides a continuously variable pressure source, and as the fan speed increases, ΔP increases. If maintained at a constant speed, blower mechanism 800 can provide a constant ΔP.

In some aspects, operation of blower mechanism provides an extra springiness in the patient's exhalation, and can be configured to run continually throughout the administration of a treatment. Blower mechanisms such as those shown in FIG. 8 are transferable, and universal in their applicability. For example, blower mechanisms can be incorporated into anesthesia machines, mechanical ventilators, bag valve masks, and the like.

In some instances, a blower mechanism may include a motor and turbine, where the turbine is independent from the motor. For example, a hermetic seal may be disposed between the motor and turbine, and a magnetic clutch may be used to operationally couple the turbine with the motor. Relatedly, turbines may be provided in a single-patient-use configuration, as a disposable item that is coupled with the motor assembly and used for a particular patient, and discarded afterward. In some configurations, a blower mechanism provides a centrifugal fan that can be coupled between a patient and a breathing system such as a ventilator. In some instances, a limb flow control assembly, such as blower mechanism 800 of FIG. 8, blower mechanism 940 of FIG. 9, blower mechanism 1000 a of FIG. 10A, blower mechanism 1000 b of FIG. 10B, or blower mechanism 1100 of FIG. 11, may include separate motor and turbine mechanisms. For example, a blower mechanism may include a motor mechanism and a turbine mechanism which are hermetically sealed from one another. The motor mechanism can be attached with the turbine mechanism via a magnetic or mechanical clutch mechanism. In some instances, the motor mechanism and the turbine mechanism may not share a common gas path, for example, through a turbine shaft bearing. In some instances, a turbine mechanism may be provided and used as a single patient use device. Relatedly, the motor mechanism may be provided and used as a capital device. Exemplary detachable negative pressure turbine mechanisms are further described herein in association with FIG. 20.

If blower mechanism 800 is connected with a patient, in the absence of a ventilation device, then operation of blower mechanism 800 can provide a steady state by reducing the intrathoracic pressure to the level of $\Delta P$. If the patient takes a spontaneous inhalation breath, for example which acts to draw air through blower mechanism, in a counter-flow direction across the fan, and into the lungs, the patient is effectively working against the $\Delta P$ (e.g. $-10$ cm $H_2O$) provided by the blower. Upon exhalation, the intrathoracic pressure returns to $\Delta P$.

In addition to positive pressure provided by a ventilator, and negative pressure provided by the blower, it is also helpful to consider the pressure generated by the patient, either by compliance or by recoil.

During inhalation, pressure within the lungs and thorax is relatively less than pressure which is present in a mask or tracheal tube. Consequently, gas flows from the mask or tube (higher pressure) into the lungs (lower pressure). The pressure differential can be due to action of the patient's diaphragm, optionally in combination with operation of a ventilator or blower, or both.

Conversely, during exhalation, pressure within the lungs and thorax is relatively greater than pressure which is present in a mask or tracheal tube. Consequently, gas flows from the lungs (higher pressure) into the mask or tube (lower pressure). The pressure differential can be due to elastic recoil or rebound of the patient's lungs, optionally in combination with operation of a ventilator or blower, or both.

As an illustrative example, a turbine fan operating at a given speed may produce 10 cm $H_2O$ of pressure, thus pulling gas out of the patient at a pressure of 10 cm $H_2O$. When providing a positive pressure breath from a ventilator which delivers gas to the patient, during exhalation the expired gas flows out of the patient and out through the blower mechanism. When the pressure in the patient's lungs and the pressure provided by the blower mechanism are equal, the net flow through the blower mechanism is zero.

These techniques can be provided in a variety of situations, including instances where a patient is spontaneously breathing. Optionally, these techniques may be used on conjunction with a bag mask valve treatment, an anesthesia treatment, or a mechanical ventilator treatment.

With continuing reference to FIG. 8, arrow B represents the negative pressure created in the patients lungs, and the blower pressure $\Delta P$ is represented by arrow A. When these pressures become equal (e.g. negative pressure in patients lungs equals the pull from the blower) then net flow through the blower is zero. In this situation, the blower fan, operating as a pressure source, is still spinning, however there is no mass or net flow going one direction or the other.

In some cases, a mechanical ventilator may be considered as a volume device (e.g. administering 500 ml gas volume) which delivers gas in a contra-flow direction through the blower mechanism (e.g. against the blower backpressure). Ventilating against such backpressure can be effected easily, because the ventilator is only pushing back against that 5 or 10 cm of $H_2O$, or whatever $\Delta P$ is produced by the turbine running at the designated IPR setting. In aerodynamic terms, it is possible that when running such flow back through the turbine, the turbine may stall slightly, because it is not as effectively propelling gas forward in the intended direction.

As noted elsewhere herein, the blower mechanism may operate at a continuously variable speed. Relatedly, it may be possible to turn the blower off, so as to provide a $\Delta P$ of zero, and turn the blower on to a selected speed, so as to provide 5 cm of $H_2O$, for example. In this instance, the ventilator will need to produce an opposing 5 cm of $H_2O$ of incremental pressure, in order to drive gas into the patient's lungs. Hence, when opening the exhalation valve, the patient will exhale, with the energy of an additional 5 cm of $H_2O$.

According to some embodiments, it is possible to use a pressure difference between inlet and outlet of the blower as a flow transducer, so as to measure patient flow.

Figure 8A:
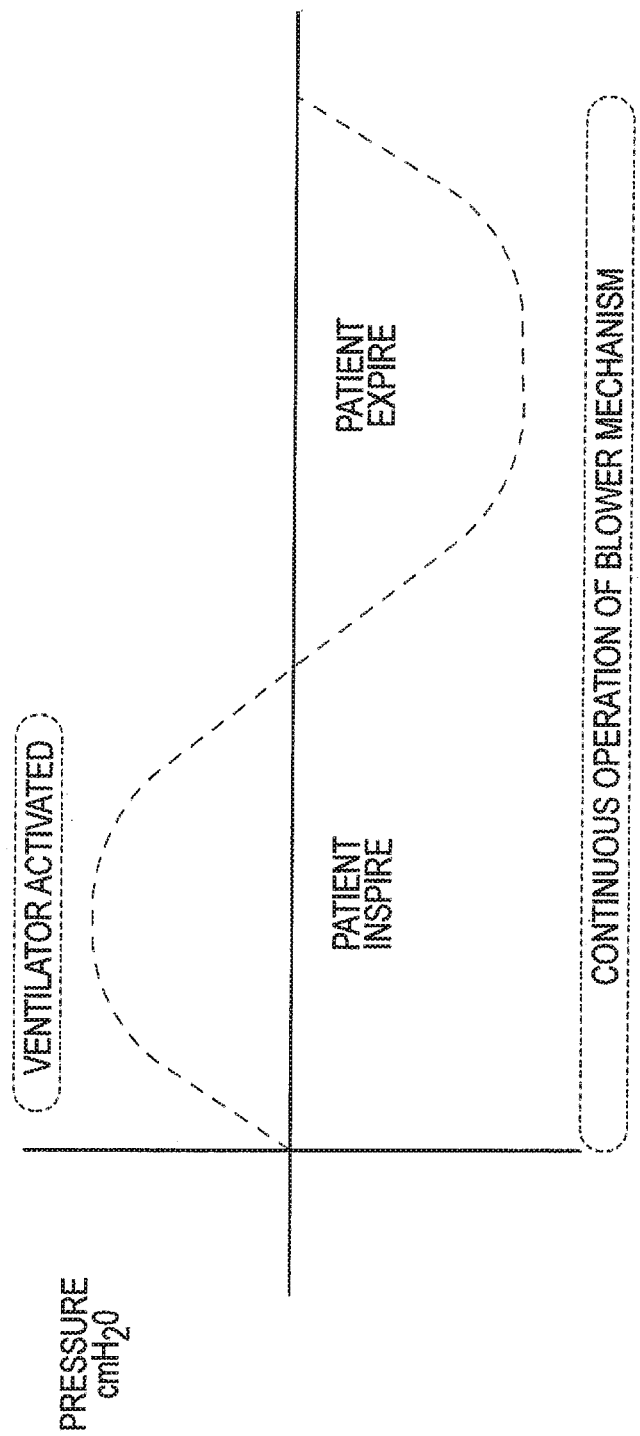
FIG. 8A shows aspects of the operation of a blower mechanism according to embodiments of the present invention.

FIG. 8A shows an exemplary pressure curve provided by a treatment system having a blower mechanism (e.g. as shown in FIG. 8), but not a separate threshold valve (e.g as shown in FIG. 1). As depicted here, a blower mechanism is continually operated. A positive pressure breath provided by a ventilator increases the intrathoracic pressure, and once the positive pressure breath ceases, the activity of the blower mechanism decreases the intrathoracic pressure.

At the lowest airway pressure, the net flow across the turbine is zero. For example, if the blower is spinning sufficiently to produce 10 cm $H_2O$, and the patient airway pressure is at $-10$ cm $H_2O$, then the net flow across turbine is zero. During inspiration, gas flows from the ventilator or bellows, in a counter-flow direction, across the turbine and into the patient's lungs. Upon expiration, gas flows out of the patient's lungs. In large part, each amount of gas volume that enters or exits the patient's airway also travels across the turbine blade, which is in series with the patient's airway. In some instances, the pressure curve will not be a sine wave, but instead will present an exponentially decelerating flow in a downward direction, at exhalation/expiration, which corresponds to a rapid or high speed initial exhalation upon opening of an exhalation valve during a mechanical exhalation phase of a ventilator.

The initial positive pressure curve may also correspond to the compression of a bag valve mask, which produces retrograde flow across the turbine blade. The shape of the inspiration pressure curve or waveform (e.g. sinusoidal) reflects the characteristics of the compression applied. For example, the bag may be compressed rapidly or gradually, and may be released rapidly or gradually. Inspiratory flow, upon release of the bag, will decelerate. As the bag compression is released, the pressure provided by the bag will at some point no longer exceed the pressure countervailing pressure provided by the blower mechanism (e.g. the bag pressure falls below the turbine $\Delta P$). At this point, the blower mechanism operates as a valve that switches open, thus allowing net flow of gas to pass therethrough as exhalation. Hence, after the bag is released, gas flow exits the system thus providing a negative pressure as shown on the pressure curve. When the turbine acting in this way as an exhalation valve does open, the gas may exit the patient at a rapid rate of flow. The exhalation may be due to the combined effect of the patient's normal passive exhalation, in series with the centrifugal blower. Hence, the graph or waveform curve may exhibit an initial downward spike, followed by an exponential decay in an upward direction. Accordingly, the bag initially pushes gas into the patient by operating as an inspiration source, after which gas flows back out of the patient while the bag refills. Upon exhalation, gas exits the patient's lungs, due to the patient's compliance and operation of the turbine.

Hence, with reference to both FIGS. 1A and 8B, it is understood that during the expiration phase, the intrathoracic pressure according to a particular profile or curve, which can be characterized by the magnitude and/or the duration of the pressure. In some embodiments, systems and methods provide a patient with a lower intrathoracic pressure for some duration of time. For example, techniques may involve providing the patient with a lower intrathoracic pressure for a duration that is based on a ventilation rate or a breathing rate (e.g. from 25% up to 100% of the expiratory time period). Hence, the duration of the lowered intrathoracic pressure may depend on the duration of the expiratory phase. A typical inspiratory:expiratory ratio is between about 1:2 and about 1:4, and the average respiratory rate for a healthy adult at rest is between about 10 breaths per minute and about 20 breaths per minute. Breathing rates of infants and children are typically higher (e.g. up to 35 breaths per minute). Hence for an adult, a relatively shorter expiratory phase may be about 2 seconds, and a relatively longer expiratory phase may be about 4.8 seconds. Where the lower intrathoracic pressure is about 25% of the expiratory time period, the duration may be between about 0.5 seconds and about 1.2 seconds. Where the lower intrathoracic pressure is about 100% of the expiratory time period, the duration may be between about 2 seconds and about 4.8 seconds. In some instances, the lowered intrathoracic pressure may have a duration between about 0.5 seconds and about 4.8 seconds. In some instances, the lowered intrathoracic pressure may have a duration between about 0.8 seconds and about 4.5 seconds. In some instances, the lowered intrathoracic pressure may have a duration between about 1.1 seconds and about 4.2 seconds. In some instances, the lowered intrathoracic pressure may have a duration between about 1.4 seconds and about 3.9 seconds. In some instances, the lowered intrathoracic pressure may have a duration between about 1.7 seconds and about 3.6 seconds. In some instances, the lowered intrathoracic pressure may have a duration between about 2.0 seconds and about 3.3 seconds. In some instances, the lowered intrathoracic pressure may have a duration between about 2.3 seconds and about 3.0 seconds. In some instances, the lowered intrathoracic pressure may have a duration between about 1.0 seconds and about 4.0 seconds. In some instances, the lowered intrathoracic pressure may have a duration between about 2.0 seconds and about 3.0 seconds. In some cases, the lowered intrathoracic pressure may have a value between about 0 cm $H_2O$ and about −15 cm $H_2O$. Relatedly, embodiments encompass systems and methods for providing therapy to a patient that involve means for delivering a positive pressure breath to an airway of the patient during an inspiration phase, and means for delivering a negative pressure to the airway of the patient during the inspiration phase and during an expiration phase, wherein the duration of the negative pressure is based on a ventilation rate or a breathing rate (e.g. from 25% up to 100% of the expiratory time period). In some instances, the lowered intrathoracic pressure may have a duration between about 0.5 seconds and about 4.8 seconds. In some instances, the lowered intrathoracic pressure may have a duration between about 0.8 seconds and about 4.5 seconds. In some instances, the lowered intrathoracic pressure may have a duration between about 1.1 seconds and about 4.2 seconds. In some instances, the lowered intrathoracic pressure may have a duration between about 1.4 seconds and about 3.9 seconds. In some instances, the lowered intrathoracic pressure may have a duration between about 1.7 seconds and about 3.6 seconds. In some instances, the lowered intrathoracic pressure may have a duration between about 2.0 seconds and about 3.3 seconds. In some instances, the lowered intrathoracic pressure may have a duration between about 2.3 seconds and about 3.0 seconds. In some instances, the lowered intrathoracic pressure may have a duration between about 1.0 seconds and about 4.0 seconds. In some instances, the lowered intrathoracic pressure may have a duration between about 2.0 seconds and about 3.0 seconds. In some cases, the lowered intrathoracic pressure may have a value between about 0 cm $H_2O$ and about −15 cm $H_2O$.

Figure 9:
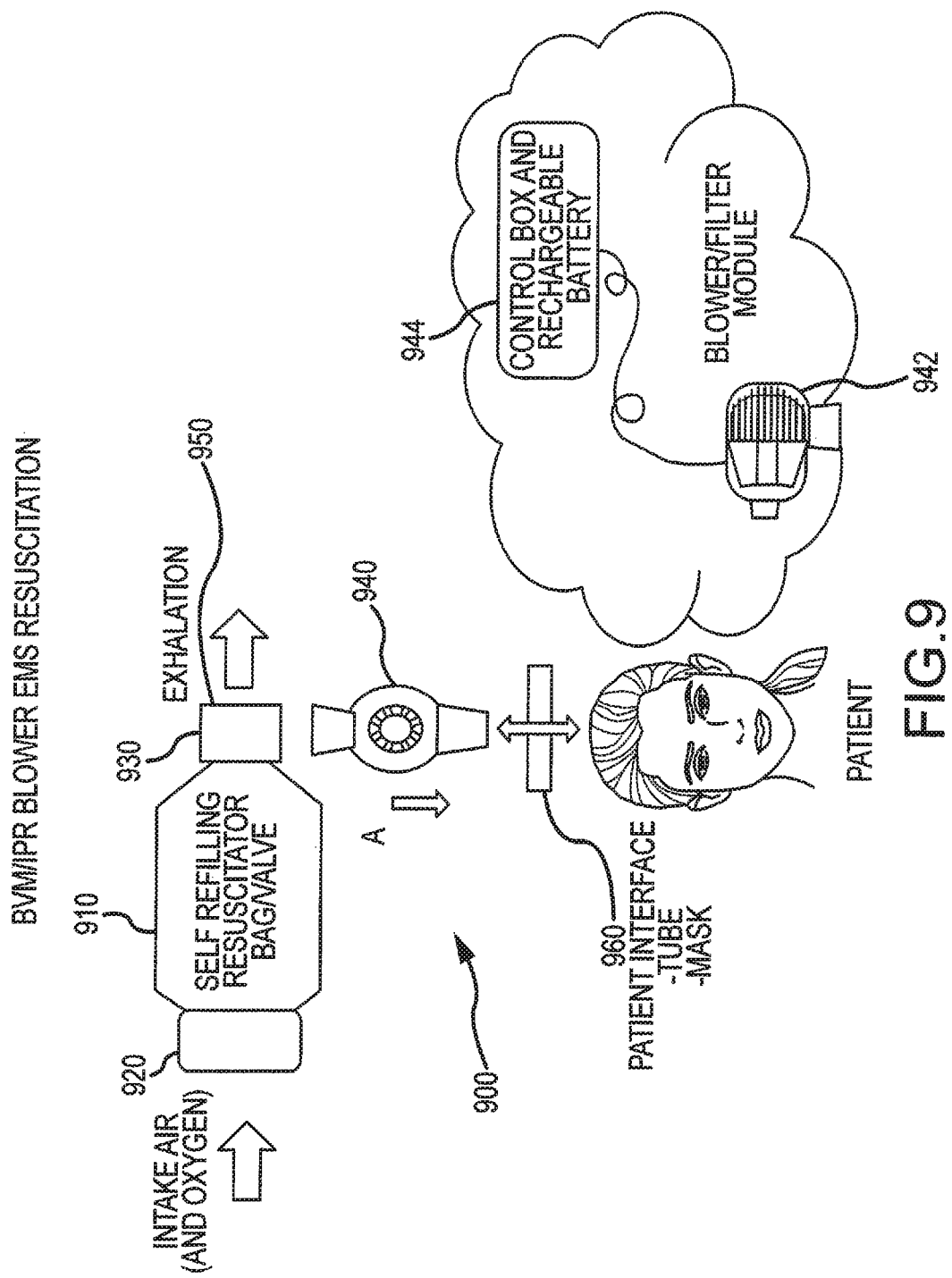
FIG. 9 shows aspects of a treatment system which includes a self-refilling resuscitator bag/valve mechanism according to embodiments of the present invention.

A single mechanism approach can also be used with a resuscitator device. For example, FIG. 9 shows treatment system 900 which includes a self-refilling resuscitator bag/valve mechanism 910 having an intake 920 (e.g. for air and oxygen) and a wye 930. In operation, gas is moved through the bag intake 920, through bag 910, through wye 930, through blower mechanism 940, and into the patient. Gas also moves from the patient, through blower mechanism 940, through wye 930, and through an outlet 950. As depicted here, blower mechanism 940 may include a blower/filter module 942 coupled with a control box and rechargeable battery assembly 944. Such embodiments are well suited for use by emergency medical services (EMS) personnel, or in situations where patients benefit from out-of-hospital acute medical care. Optionally, such embodiments may be used in a hospital setting.

In some embodiments, system 900 includes a patient interface, such as a mask or tube 960. Compression of bag 910 can force air across blower 940 in a direction indicated by arrow A, through mask 960, and into the patient. Upon release of compression from the bag 910, gas flows from the patient's lungs, through mask 960, across blower in a direction indicated by arrow B, through wye 930, and out of exhalation valve 950 which is now an open configuration, until a steady state is reached between the blower and the patient. In some embodiments, blower mechanism 940 is in continual operation, thus providing a ΔP, while bag 910 is repeatedly squeezed and released. At those times when pressure in the patient's lungs is equal to ΔP created by the fan, there is no net flow across the blower. According to some embodiments, when the IPR pressure, created by the turbine, and the negative pressure in the patient's chest are equal, flow will be zero (e.g. no inflow, no outflow). In other words, the turbine will spin, but with no gas-motive effect. A centrifugal blower can be considered as a pressure generating device, as opposed to a constant flow pump. When an equal and opposing pressure is present, the blower will not increase its operating pressure. Therefore, flow stops. Hence, a fan spinning at a nominal speed produces a nominal pressure, and if that pressure is exceeded (e.g. by compression of the bag), it is possible to push gas back through the fan in retrograde flow, across the blower and into the patient. When releasing compression applied to the bag (or otherwise ceasing or reducing delivery of the positive pressure breath), exhalation gas is allowed to flow out in concert with patients recoil breath from chest compliance, which in addition to pressure provided by the fan, produces a total outward drive pressure.

In some embodiments, systems may include a controller 944 which can operate based on monitoring and feedback (e.g. airway pressure or flow levels through the fan), for example to determine desired fan speeds. Hence, controller 944 may provide instructions to reduce the fan speed during inspiration, and increase the fan speed during exhalation. Such techniques can be used to provide any of a variety of pressure profiles, so for example pressure may be reduced or increased to a desired level, for a desired period of time, optionally in coordination with the ventilator operation and/or patient breathing, throughout the course of a treatment or a portion thereof. In some cases, such techniques involve activating, deactivating, or otherwise modulating the potential pressure that is generated by the blower. Operation of the blower can be based on monitoring or feedback information from various places throughout a treatment system. In some cases, a treatment system or blower mechanism may include a pressure sensor, which detects or measures a ΔP across the blower. Such sensors can be used to evaluate flow and other parameters across the blower, or at other locations throughout the treatment system.

Figure 10:
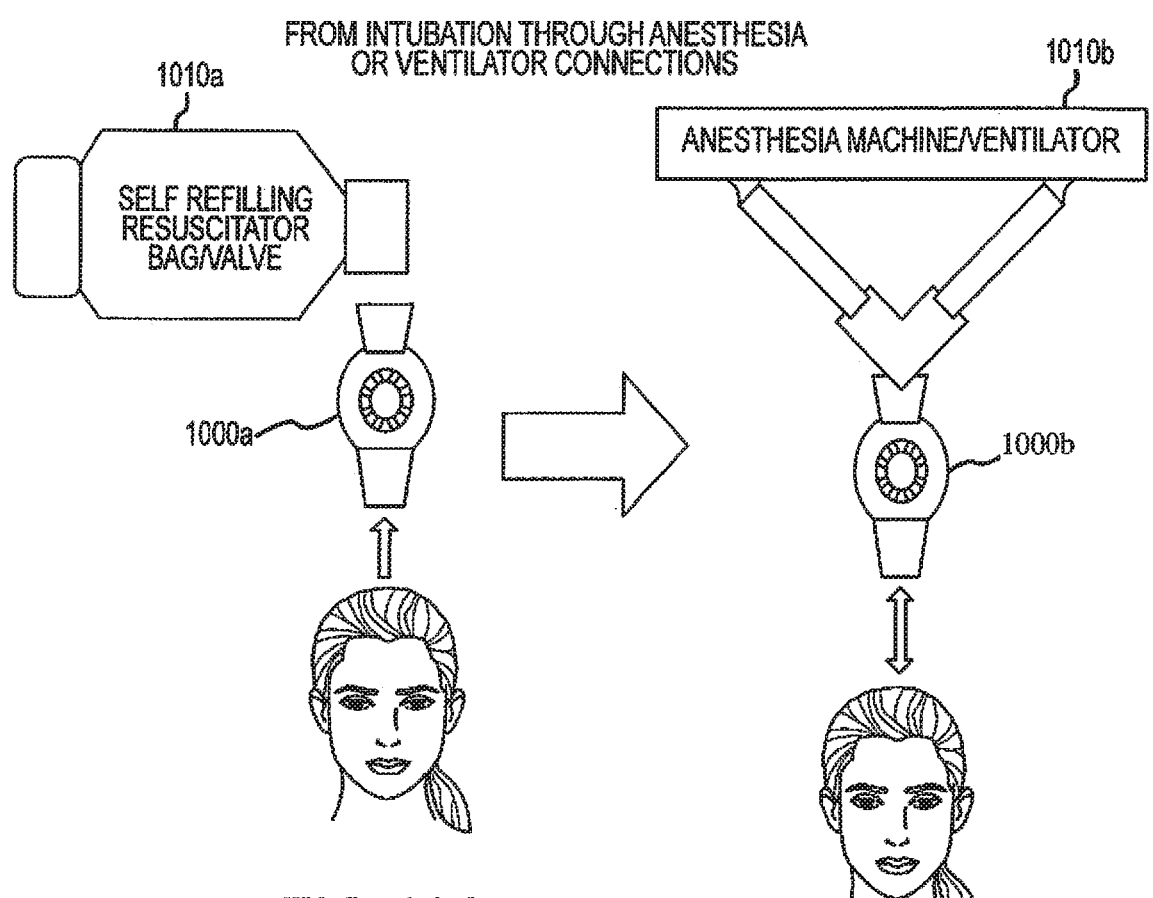
FIGS. 10A and 10B show aspects of blower mechanisms according to embodiments of the present invention.

As depicted in FIGS. 10A and 10B, blower mechanisms can be used from intubation through anesthesia or ventilator connections. FIG. 10A shows a blower mechanism 1000 *a* coupled between a self-refilling resuscitator bag/valve device 1010 *a* and a patient. FIG. 10B shows a blower mechanism 1000 *b* coupled between an anesthesia machine or ventilator 1010 *b* and a patient. Such systems are well suited for use in emergency and hospital settings. For example, a hospital may receive an extremely ill patient in the intensive care unit. The patient may have been without food or nutrition for several days, on the borderline of respiratory failure, optionally presenting a variety of other comorbidities. A doctor or intensivist may wish to intubate the patient. However, in order to intubate the patient it may be necessary to administer drugs to paralyze or sedate the patient, and such pharmaceuticals may cause a drop off in blood pressure and a reduction in circulation, thus further compromising the patient's precarious condition. One example of this clinical scenario is before and after a rapid sequence induction with an anesthetic regimen, where a device as described in FIG. 10B would be of clinical value.

In these and similar instances, it is possible to provide intrathoracic pressure therapy to the patient according to embodiments of the present invention, so as to ventilate the patient (e.g. with a bag valve mask system), for example while the patient is spontaneously breathing, so as to provide the patient with improved or elevated oxygen levels, or otherwise to provide them with a pre-oxygenation treatment, thus improving or enhancing circulation. In this way, the doctor or intensivist can pre-treat the patient with IPR therapy prior to administering the sedation drugs, thus improving the patient's ability to accommodate the drugs and subsequent intubation.

Once the patient has been intubated, embodiments of the present invention may be used to deliver IPR therapy so as to support the patient's circulation. Hence, a single blower mechanism (1000 *a* as shown in FIG. 10A, and 1000 *b* as shown in FIG. 10B), coupled with the patient's airway, can be used with a bag (as shown in FIG. 10A) or with an anesthesia machine or ventilator (as shown in FIG. 10B). Due to the portability and universal applicability of the blower mechanism, the patient can alternately be treated with the bag, ventilator, or anesthesia system, as desired by the intensivist or doctor, simply by disconnecting and connecting the blower mechanism to the desired positive pressure administration device (e.g. by connecting the blower with a wye piece associated with the positive pressure system). Hence, the blower mechanism allows the patient to be freely transferred from one device to another, while retaining the ability to provide IPR to the patient as desired.

When the patient is disconnected from the bag and connected to the ventilator, the ventilator then can operate to push gas back through the blower mechanism during inspiration, thus continuing the IPR therapy previously provided by the bag. During exhalation, the exhalation gas flows out of the patient and through the blower, until the pressure is equivalent to that provided by the blower mechanism, in which case the flow become zero. In this way, the blower mechanism can assist the exhalation action of the patient, regardless of whether the patient is being treated with a bag, an anesthesia machine, or a ventilator.

Figure 11:
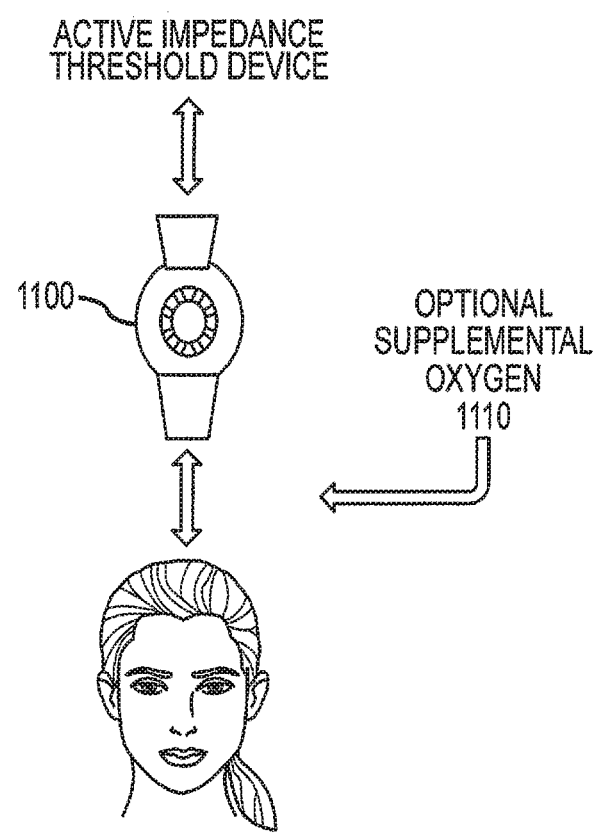
FIG. 11 show aspects of a blower mechanism according to embodiments of the present invention.

FIG. 11 shows a blower mechanism 1100 that can be coupled with a patient, optionally in combination with a supplemental oxygen source 1110. According to this embodiment, it is possible to deliver supplemental oxygen to the patient, by providing supplemental oxygen between the blower and the patient, so that when the patient receives an inspiration or takes an inspiration, or breathes spontaneously, then they can obtain the supplemental oxygen.

In some cases, a mechanical dead space may exist within a turbine. By providing oxygen between the turbine and the patient, it is possible to expeditiously or efficiently deliver oxygen to the patient without the oxygen being diluted by gas present in the dead space (e.g. if oxygen were to enter the blower first, before reaching the patient, during inspiration the patient would receive the gas content of the blower prior to receiving the oxygen enriched air in the patient's lungs). As shown here, oxygen is initially directly administered to the patient's lungs, and is subsequently pulled back out and through the turbine. The supplemental oxygen flow configuration shown in FIG. 11 also provides the effect of flushing out any carbon dioxide that may be present in the turbine. Again, once the desired intrathoracic pressure has been achieved in the patient's lungs, net flow through the blower mechanism become zero. If the net flow is not zero, and there is carbon dioxide in the turbine, a nominal amount of flush flow provided by the supplemental oxygen source may operate to dispel carbon dioxide from the turbine. In some cases, the supplemental oxygen may be provided with a small amount of bias flow, which can clear out dead space which may be present inside the turbine. Such bias flow can also help to push carbon dioxide or exhaled gas out through the blower and away from the patient. Hence, when the next inspiration occurs, fresh gas is delivered to the patient.

Figure 12:
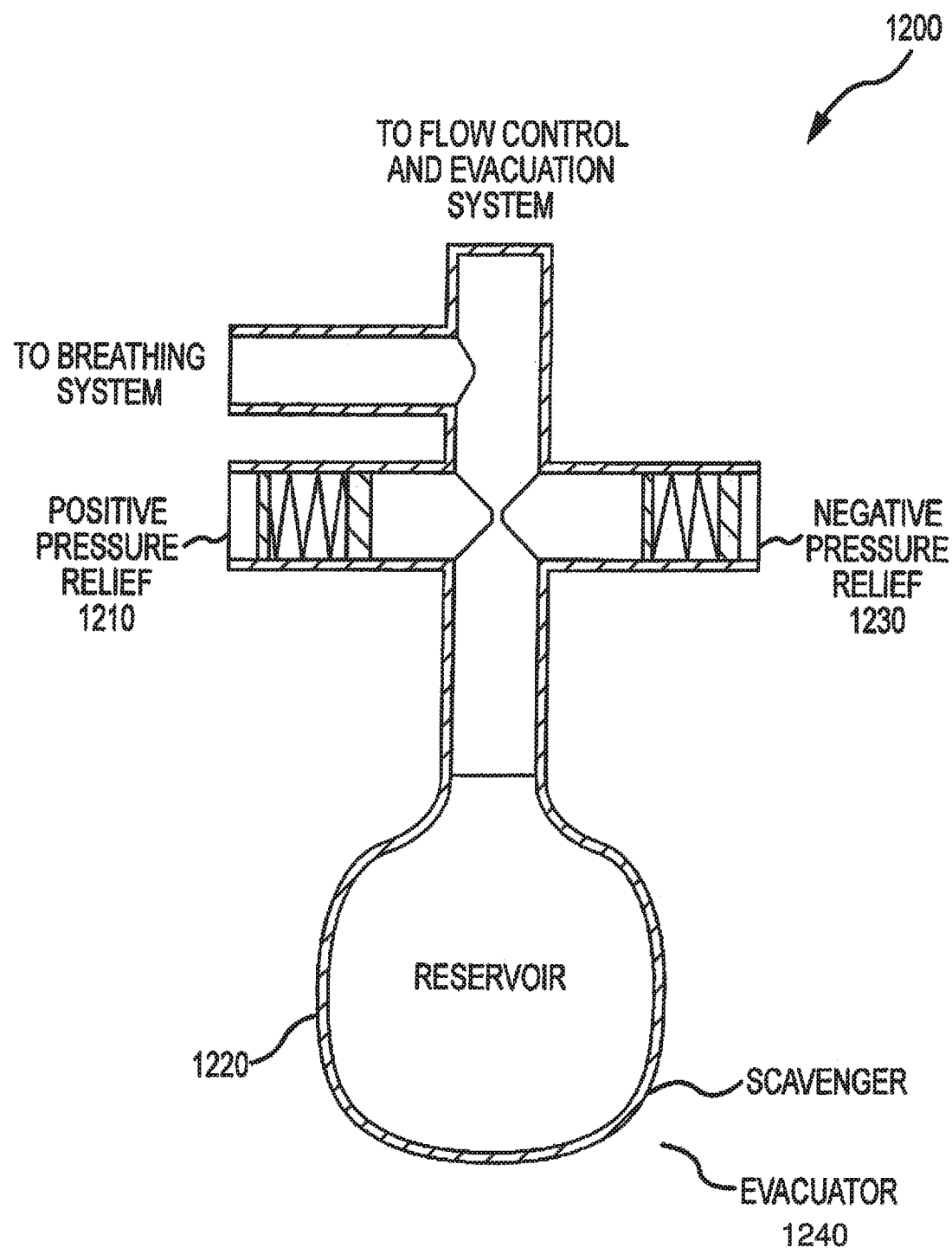
FIG. 12 depicts aspects of a negative pressure relief valve apparatus according to embodiments of the present invention.

FIG. 12 provides a schematic drawing of a negative pressure relief valve apparatus 1200, according to embodiments of the present invention. In some cases, valve apparatus 1200 may be referred to as an anti-asphyxiation valve. Operation of the valve apparatus may involve the use of a negative pressure device positioned at the evacuator connection of an anesthesia machine, which can reduce the pressure within the entire circuit, while exhausting gas within the circuit to a suction or to atmosphere. Hence, by connecting a suction apparatus or source to the outlet of the anesthesia machine, or to the evacuator connection of the anesthesia machine, it is possible to reduce the circuit pressure down to a threshold pressure. This may be done in conjunction with operation of a relief valve.

Valve apparatus 1200 may include a positive pressure relief valve 1210, which operates to prevent the reservoir 1220 from becoming overly full, in which case reservoir 1220 may produce an unwanted back pressure. A negative pressure relief valve 1230 can operate to prevent the accumulation of too much suction within the circuit. According to some embodiments, evacuator 1220 operates to remove overflow from the anesthesia breathing system. Typically, fresh gas is constantly flowing in and, absent the small effects of patient uptake and leakage, eventually leaves the breathing system. Evacuator or scavenger 1220 operates to remove that gas to the hospital suction system. Scavengers are typically equipped with a valve to relieve overpressure and under-pressure in the scavenging system. This prevents either back-flow or suction from being introduced in the circle, as shown in FIG. 12. According to some embodiments, a negative pressure can be introduced at the scavenging port of the anesthesia breathing system, as part of a technique for introducing IPR in an anesthesia breathing system. Such embodiments may involve bypassing the +/− safety relief valves in the evacuator. Relatedly, negative pressure relief can be provided as a safety mechanism.

Figure 13:
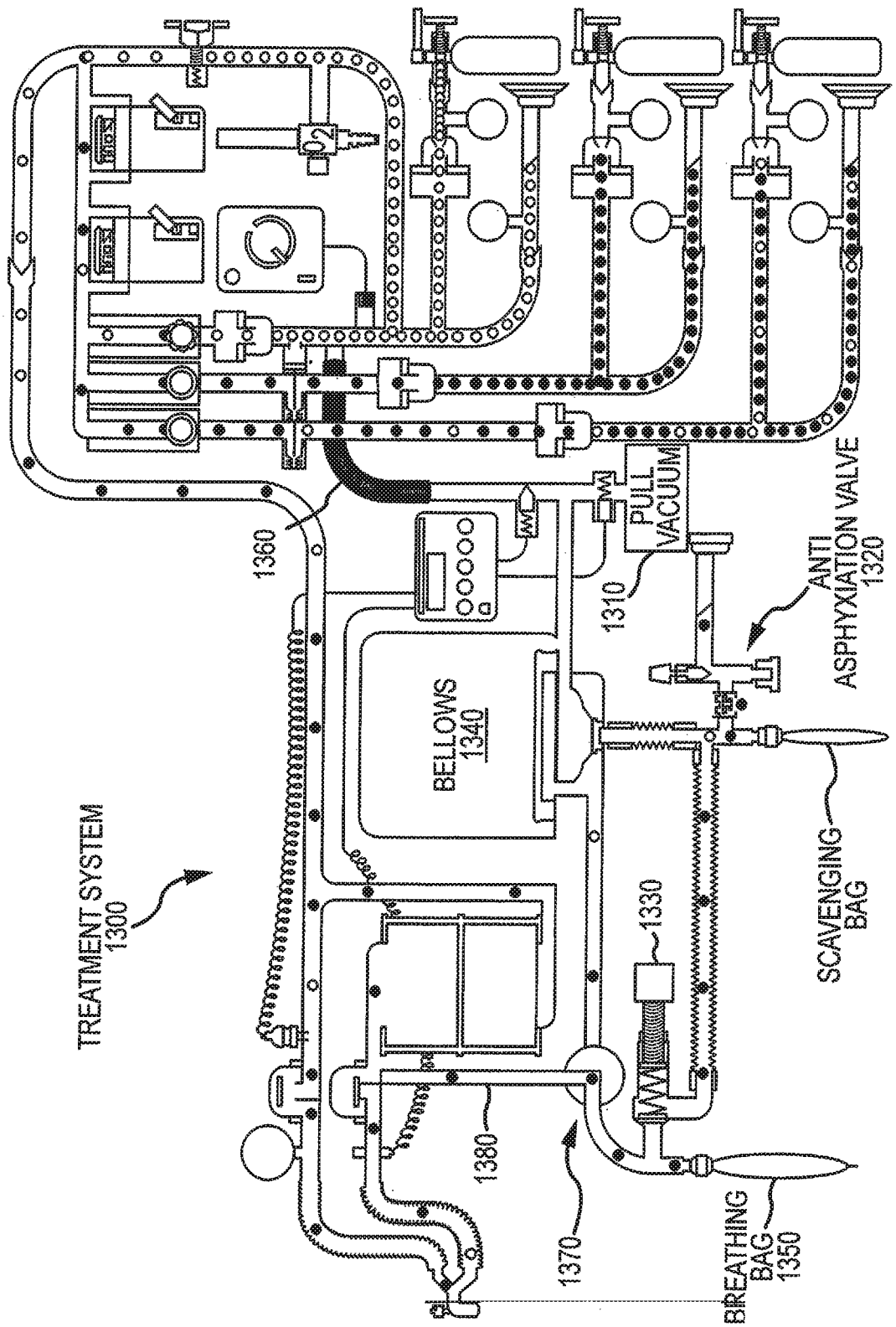
FIG. 13 shows aspects of a treatment or anesthesia system according to embodiments of the present invention.

FIG. 13 shows aspects of a treatment or anesthesia system 1300 according to embodiments of the present invention. This pneumatic schematic illustrates certain structural and functional features of a bellows driven ventilator as well. Anesthesia system 1300 can include a pull vacuum mechanism 1310. In some instances, mechanism 1310 operates in a fashion similar to that of the expiratory limb flow control assembly 40 of FIG. 1. Relatedly, in some instances, mechanism 1310 may include a turbine, a pump, a blower, or the like. Mechanism 1310 may be configured to run at a constant speed, or at a variable speed. In some instances, vacuum mechanism 1310 may provide for a connection to a vacuum source (e.g. wall vacuum source). In a gas driving system, operation of pull vacuum mechanism 1310 can generate a patient vacuum. System 1300 can also include an anti-asphyxiation valve mechanism 1320 or negative pressure relief valve. As shown here, the anesthesia system employs a circle system breathing circuit with a pneumatically driven airway pressure limiting (APL) valve 1330. In some instances, APL valve 1330 operates as an adjustable pop-off valve. APL valve 1330 may be a spring-loaded valve. The ascending bellows 1340 is depicted in the descended position at the end of an inhalation. System 1300 also includes a breathing bag apparatus 1350 which can be used to manually manipulate gas flow provided to the patient. For example, an operator may squeeze or compress breathing bag 1350, thus introducing gas into the circuit or producing a breath for the patient. Upon release of breathing bag 1350, the patient's gas circulates and ultimately fills the bag 1350. In this way, bag 1350 is filled by pressure which is present in the breathing system. According to some embodiments, breathing bag 1350 is always partially inflated and partially flaccid. Fresh gas may be provided by flow meters 1360. System 1300 may also include an automatic/manual valve 1370 (shown here in the manual position) through which exhalation gas may travel. By turning valve 1370 ninety degrees clockwise (e.g. into the automatic position), it is possible to provide a connection between bellows assembly 1340 and the breathing circuit 1380. Thus, when valve 1370 is in the automatic position, breathing bag 1350 is shut off from the breathing circuit 1380.

Figure 14:
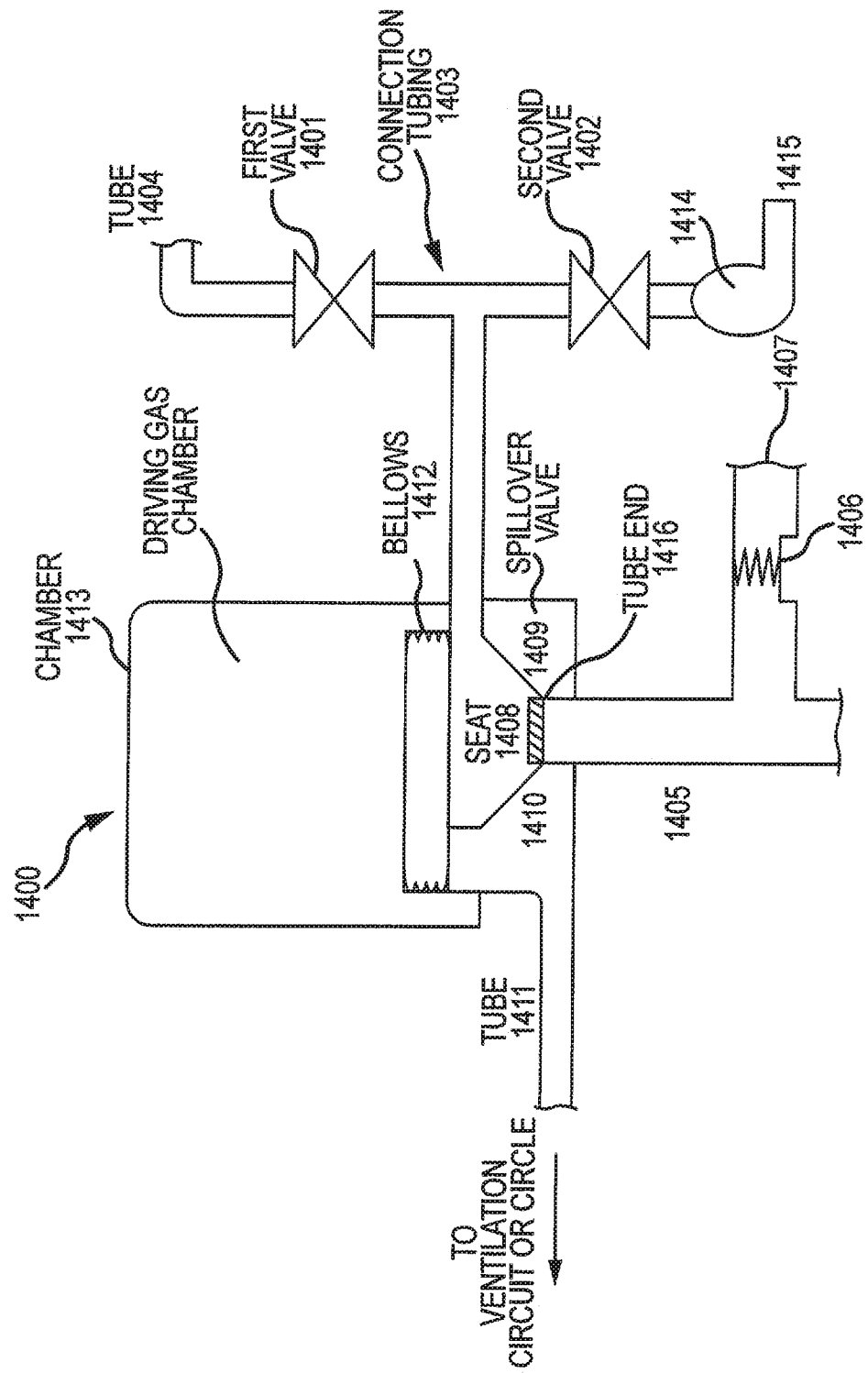
FIG. 14 illustrates aspects of a gas driven ventilator system according to embodiments of the present invention.

FIG. 14 illustrates aspects of a gas driven ventilator system 1400, according to embodiments of the present invention. Treatment system 1400 includes a first valve 1401, a second valve 1402, a connection tubing 1403 that provides fluid communication between the first and second valves, a tube 1404, an outlet from spill over valve 1405, a negative pressure relief valve 1406, a connection to vacuum system 1407, a seat 1408, a spillover valve 1409, a bellows in box body or spill over valve body 1410, a tube 1411, a bellows 1412, a chamber 1413, a vacuum generator 1414, an outlet to atmosphere 1415, and a tube end 1416. In operation, a gas driven ventilator can provide an interface between a driving gas and a respiratory gas. In some cases, the techniques described herein can be used to provide an anesthesia system having an active exhalation control.

In FIG. 14, bellows 1412 is depicted in a bottom position, which occurs at the end of inhalation. To create an inhalation, valve 1401 is opened and valve 1402 is closed. Gas can then flow from a high pressure at tube 1404 through valve 1401 and into chamber 1413 via connection tubing 1403. This driving gas forces bellows 1412 downward and closes spillover valve 1409, thereby causing seat 1408 to seal on tube end 1416, which isolates the circle. The action of bellows 1412 contracting and spillover valve 1409 closing causes ventilation gas to pass through tube 1411 to the circle system.

As part of an exhalation phase, valve 1401 is closed, valve 1402 is opened, and vacuum generator 1414 is activated. In this way, an active exhalation can be achieved. A vacuum generator assembly 1414 may include a piston pump, a centrifugal orientation blower, a regeneration blower, a "roots" type blower, a turbine, a Venturi, and the like. The action of closing valve 1401 and turning on vacuum generator assembly 1414 causes diaphragm 1412 to rise which speeds up the passive flow from the patient's exhalation, causing active exhalation.

Figure 15:
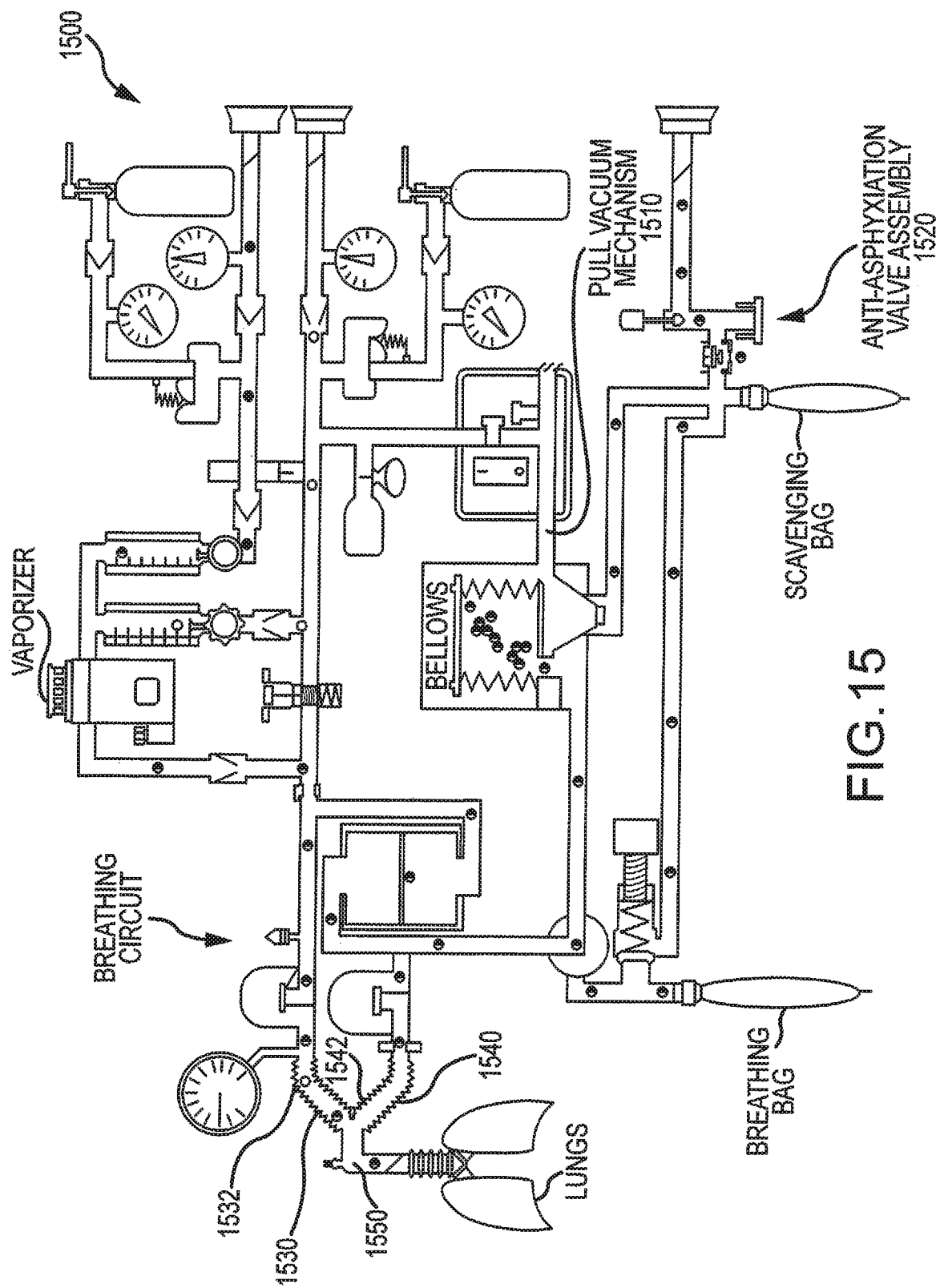
FIG. 15 shows aspects of an anesthesia or treatment system according to embodiments of the present invention.

FIG. 15 shows aspects of an anesthesia or treatment system 1500 according to embodiments of the present invention. Treatment system 1500 can include a pull vacuum mechanism 1510 and an anti-asphyxiation valve mechanism 1520. A patient circuit connects at an inspiratory valve 1530 and an expiratory valve 1540 of the anesthesia machine. A disposable set of two flexible corrugated tubes 1532, 1542 and a wye piece 1550 can provide a connection to the patient, for example via a tracheal tube or a mask.

Figure 16:
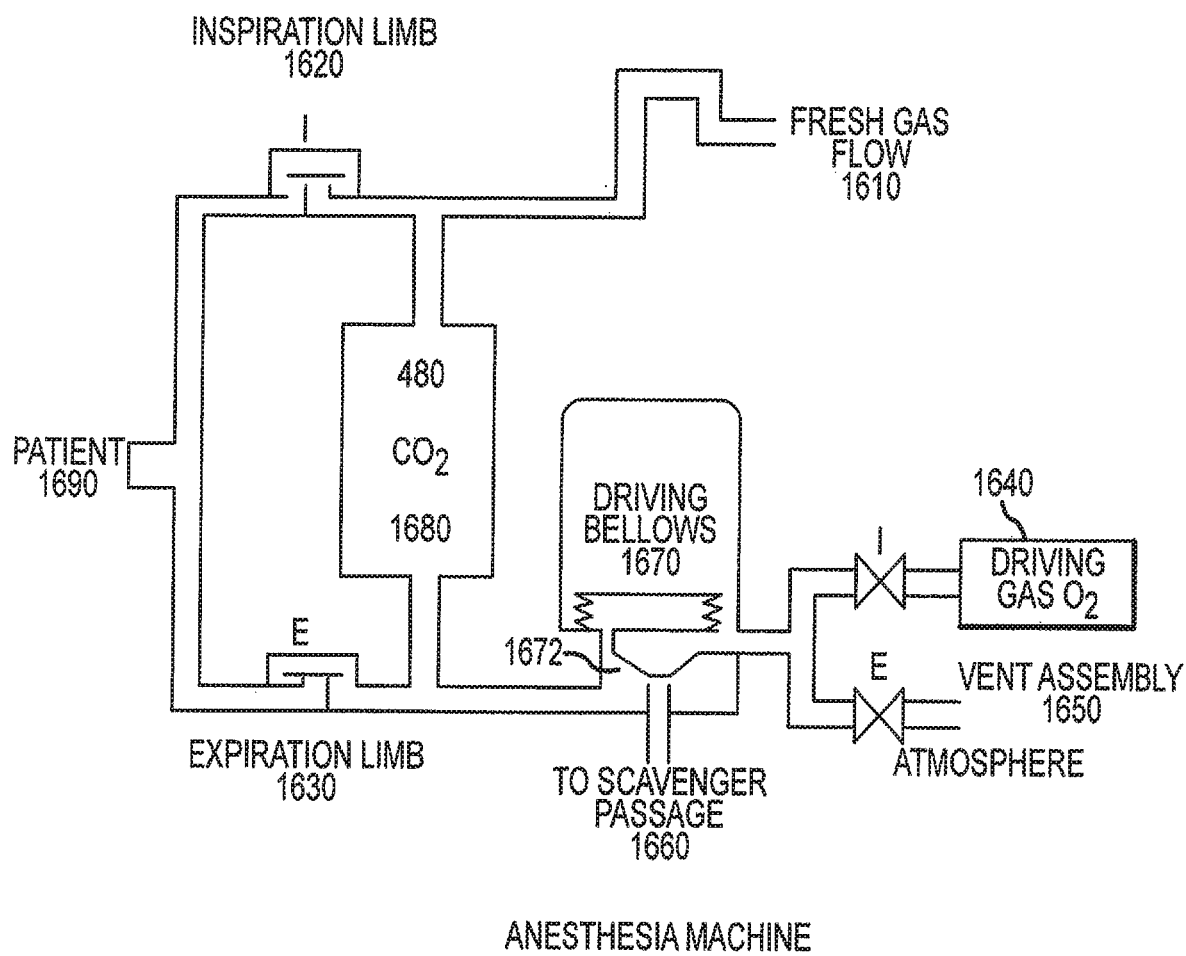
FIG. 16 illustrates aspects of an anesthesia machine according to embodiments of the present invention.

FIG. 16 illustrates aspects of an anesthesia machine 1600. As shown here, anesthesia machine 1600 includes a fresh gas flow 1610, an inspiration limb 1620, an expiration limb 1630, a driving gas 02 assembly 1640, an atmospheric vent assembly 1650, a scavenger passage 1660 which routes expelled air to a hospital vacuum, a driving bellows 1670, and a $CO_2$ mechanism 1680. Anesthesia machine 1600 can be used to treat a patient 1690. The bellows 1670 may include a spillover valve 1672 which closes at atmospheric pressure under normal operation to prevent the scavenger from pulling into negative pressure.

Figure 17:
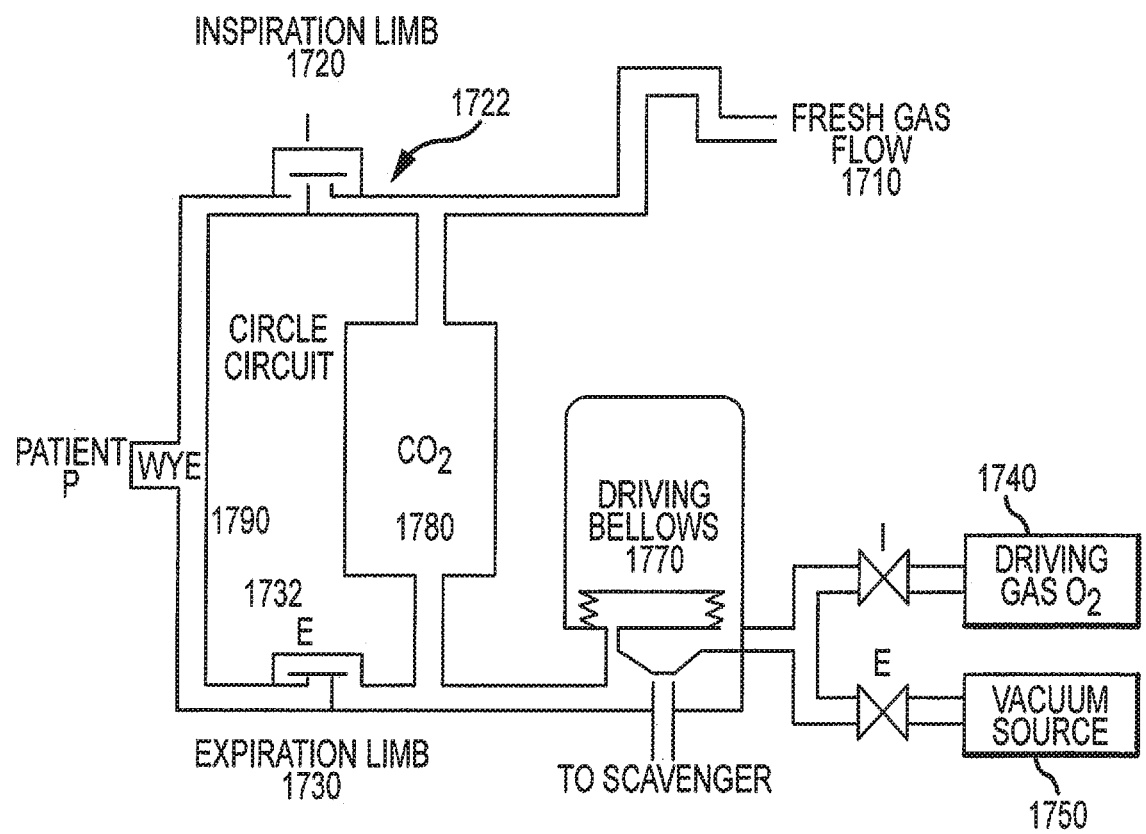
FIG. 17 illustrates aspects of an anesthesia and active exhalation system according to embodiments of the present invention.

FIG. 17 illustrates aspects of an anesthesia and active exhalation system 1700 according to embodiments of the present invention. System 1700 includes a fresh gas flow mechanism 1710, an inspiration limb assembly 1720, an expiration limb assembly 1730, a driving gas 02 assembly 1740, a vacuum source assembly 1750, a scavenger passage assembly 1760 which routes expelled air to a hospital vacuum, a driving bellows assembly 1770, and a $CO_2$ mechanism 1780. Anesthesia machine 1700 can be used to treat a patient P. As shown here, system 1700 provides a circle circuit that includes aspects of inspiration limb assembly 1720, an expiration limb assembly 1730, $CO_2$ mechanism 1780, and a wye or "T" passage 1790 which provides a fluid connection between system 1700 and a patient P. Inspiratory limb assembly 1720 includes an inspiratory check valve 1722, and expiratory limb assembly 1730 includes an expiratory check valve 1732. In use, vacuum source assembly 1750 operates to lower the pressure of the driving gas via bellows assembly 1770, thus holding the spill over valve in an open position. In this way, system 1700 can provide active exhalation for intrathoracic pressure regulation therapy to the patient.

Figure 18:
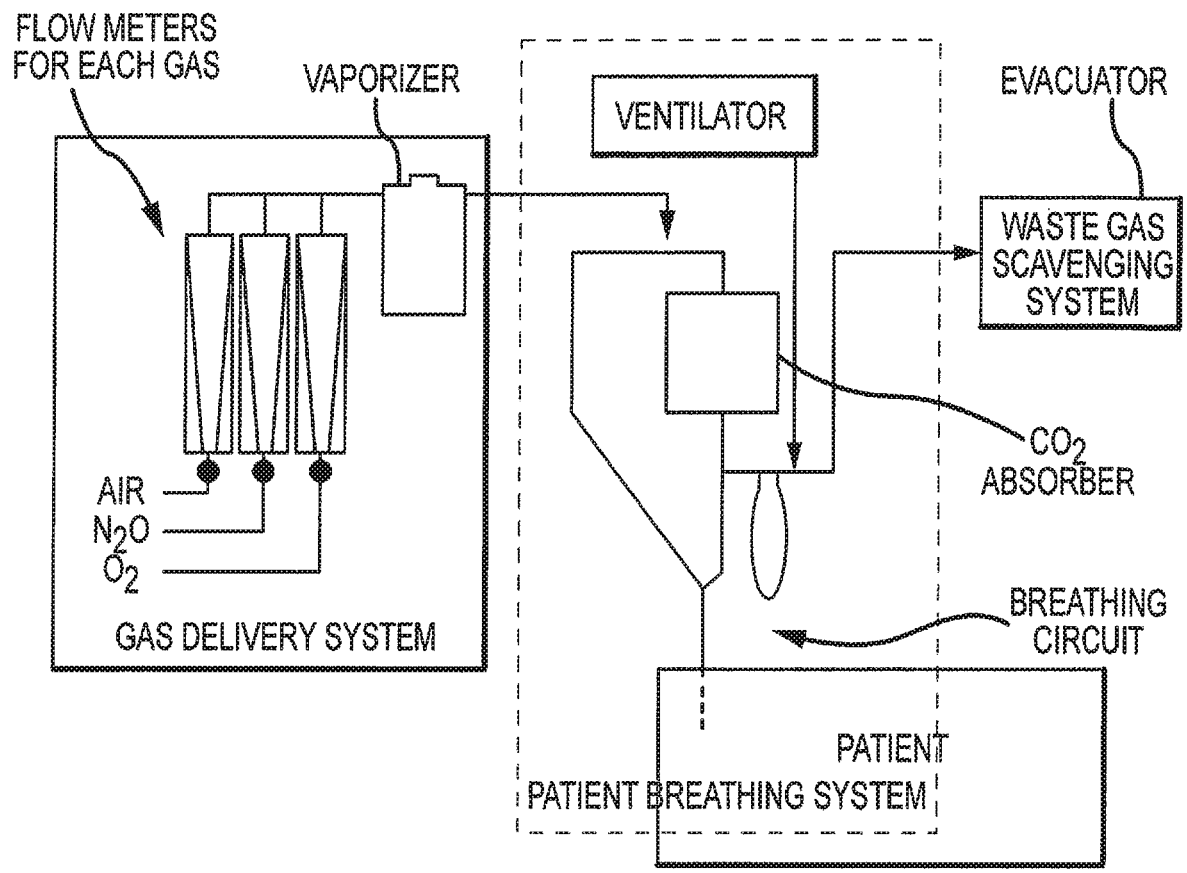
FIG. 18 illustrates aspects of an exemplary anesthesia system according to embodiments of the present invention.
Figure 19:
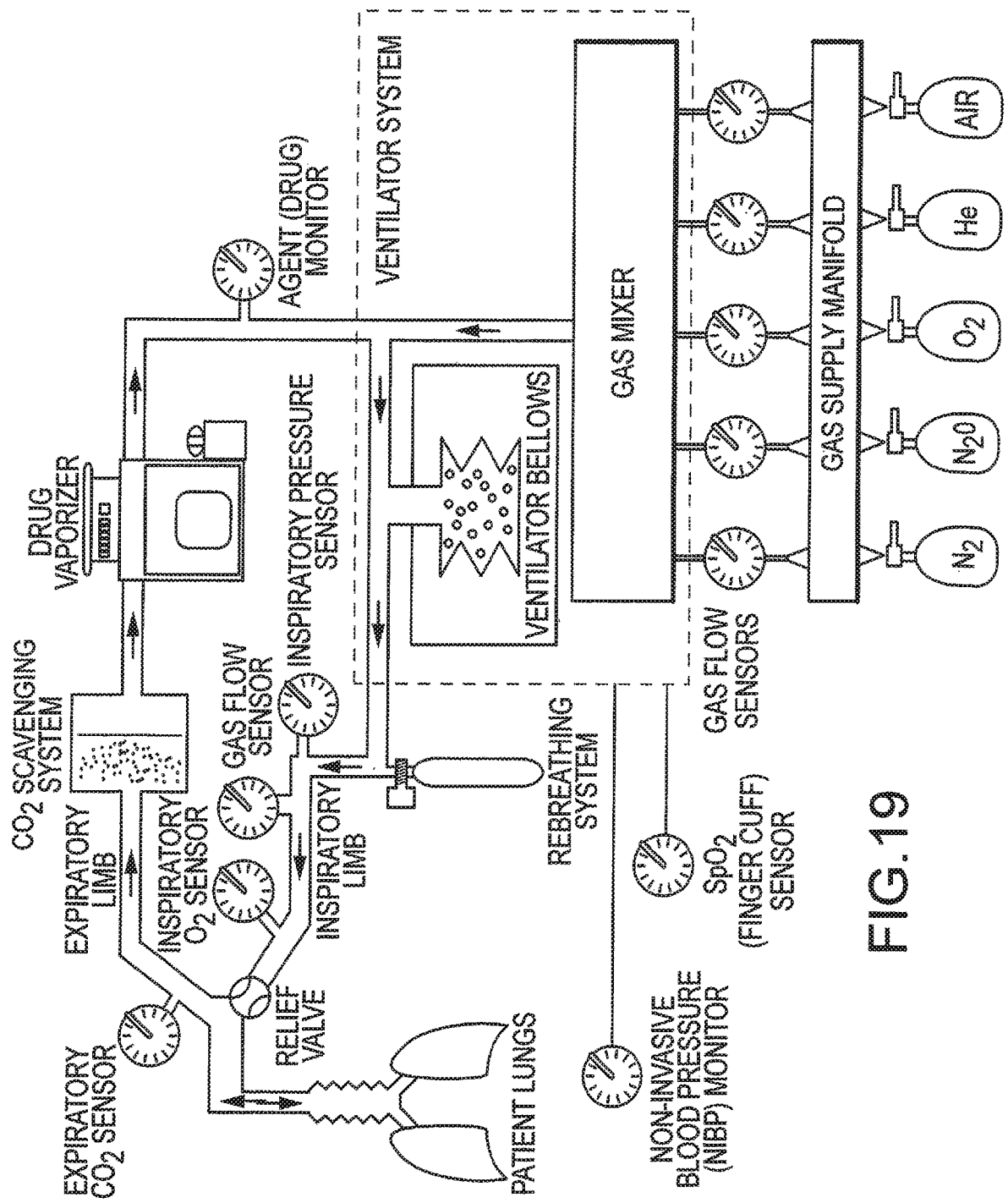
FIG. 19 illustrates aspects of an exemplary anesthesia system according to embodiments of the present invention.

FIGS. 18 and 19 illustrate aspects of exemplary anesthesia systems. As shown in FIG. 18, an anesthesia system may include a manual ventilation or pneumatic valve that allows the operator to switch back and forth between a bag and a ventilator. As shown in FIG. 19, gas may be supplied by wall supplies or by tanks Supplied gases may include medically certified gases such as $O_2$, $N_2$, $N_2O$, He, or Air. A ventilator mechanism may also include a gas mixer, which operates to mix gases together before they are provided to the patient. A ventilator can be configured to provide breaths to a patient according to any of a variety of parameters, including the respiration rate (breaths/minute), tidal volume (volume per breath), I:E ratio (Inspiration time:Expiration time ratio), inspiratory time (seconds), and inspiratory pause (delay between breaths). A vaporizer can operate to vaporize an anesthetic drug, such as Suprane, Halothane, or Enflourane, which is delivered to the breathing circuit for administration to the patient.

Figure 20:
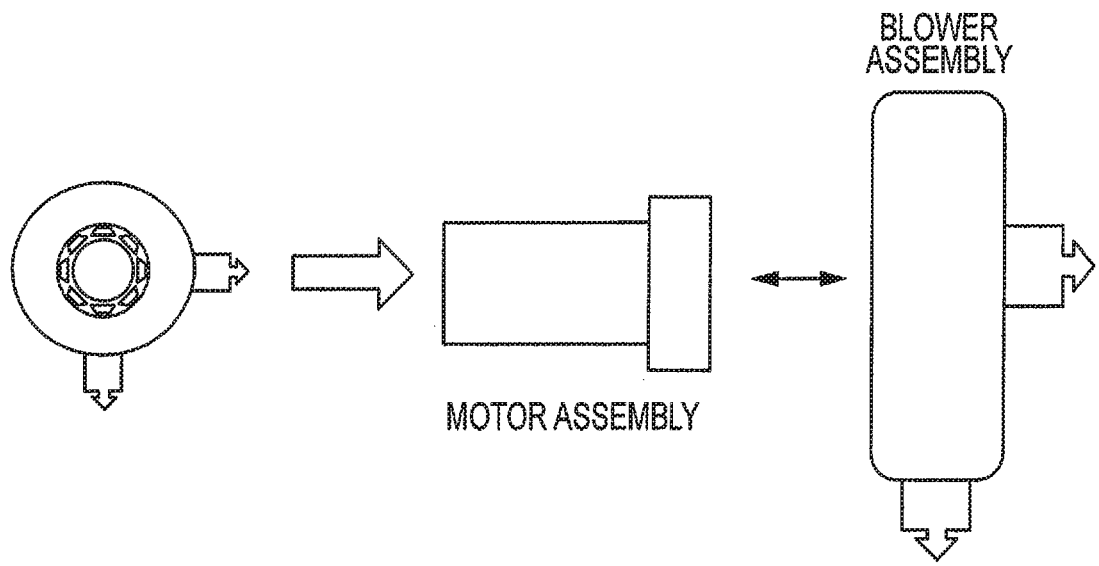
FIG. 20 depicts aspects of a detachable negative pressure turbine mechanism according to embodiments of the present invention.

FIG. 20 depicts aspects of a detachable negative pressure turbine mechanism according to embodiments of the present invention. In some cases, the mechanism may include a magnetic clutch which couples the motor with the turbine. Optionally, such coupling can occur through a barrier, which can effectively isolate the turbine from the motor. Hence, potential problems associated with oxygen, moisture, or other gases getting into the motor assembly can be reduced or avoided. In some instances, the turbine can be a single-patient-use product as opposed to a capital piece of equipment. Hence, such embodiments can lower the overall cost of ownership. When using a motorized device in the patient's airway, it is helpful to ensure that it is oxygen safe. Relatedly, to eliminate pathogens, it is helpful if the motorized device is protected with a filter, is cleanable, or is disposable. Embodiments of the present invention encompass treatment systems with disposable elements. For example, the motor assembly and the turbine assembly can include a clutching mechanism which transfers kinetic energy from the motor to the turbine. In some cases, the clutching mechanism can include a magnetic clutch or a mechanical linkage. In this way, a used blower assembly can be ejected from a motor assembly, and a new blower assembly can be mounted thereon. As shown in FIG. 20, there can be a magnetic or mechanical turbine connection between the turbine and the drive motor assembly, in the patient's gas path. The mechanical interface can be gas tight and oxygen safe. The turbine may be consumable.

Figure 21:
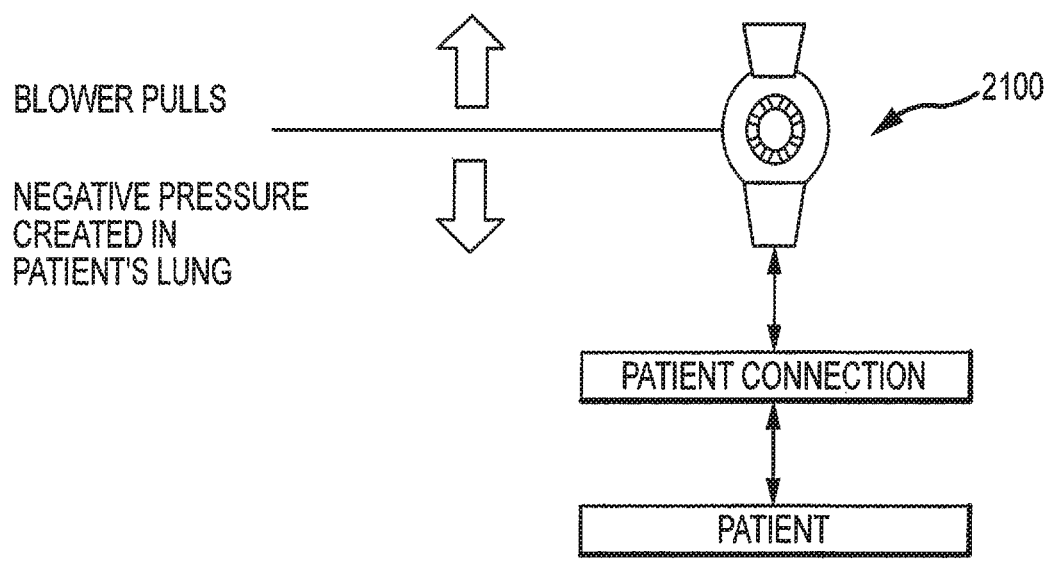
FIG. 21 illustrates aspects of an intrathoracic pressure regulation (IPR) blower mechanism which can be used to modulate flow or regulate negative pressure within the airway of a patient according to embodiments of the present invention.

FIG. 21 shows an example of an intrathoracic pressure regulation (IPR) blower mechanism 2100 which can be used to modulate flow or regulate negative pressure within the airway of a patient. As shown here, the blower or air mover can be placed in fluid communication with the patient airway, for example via a patient connection, and can operate to modulate flow or regulate negative pressure within the airway in the absence of any other valves. In some cases, the patient connection may include a mask, tube, or mouthpiece. The blower mechanism 2100 can be used on a spontaneously breathing person. Gas can flow in both directions through the air mover (e.g. away from the patient, and toward the patient). In some cases, the blower mechanism 2100 is attachable with other systems, so that for example the blower mechanism can be placed between the patient and a wye fitting on an anesthesia or ventilation machine, or between the patient and a BVM for use in mechanical ventilation. According to some embodiments, the blower mechanism 2100 can allow or provide fluid communication between the patient airway and a ventilator (anesthesia) platform while implementing the therapy. In some instances, the blower mechanism 2100 can be used in several of the respiratory platforms disclosed herein, for example anesthesia, ventilation (e.g. open circuit), manual ventilation, and spontaneously breathing patients. Blower mechanism 2100 can function in a manner similar to that described herein with reference to the blower mechanism shown in FIG. 8, may operate as a pressure generator or modulator, and can be used to create a controlled or modulated pressure within a patient airway (e.g. in a spontaneously breathing patient) or between the patient and a ventilation device (e.g. anesthesia machine, mechanical ventilator, bag valve mask, and the like). In some cases, the pressure provided by blower mechanism 2100 can be referred to as ΔP. When blower mechanism 2100 is in fluid communication with the patient's airway or mouth, which may be accomplished using a mask, tube, or similar device, blower mechanism 2100 operates to pull air or gas from the patient's lungs until a set or desired pressure is achieved. When the pressure in the lungs reaches the blower pressure, blower mechanism 2100 is in equilibrium and the net flow is zero, and a steady state pressure is achieved. Hence, a patient attached to blower mechanism 2100 may inspire, at a pressure in excess of the blower pressure ΔP, and pull in a breath. Subsequently, when exhalation begins, that breath will be exhaled, by virtue of the patient's lung recoil and the pressure of the IPR blower mechanism 2100 until, once again, equilibrium is achieved. In some instances, operation of blower mechanism 2100 assists exhalation and can be used in patient populations that benefit not only from IPR but also from enhanced exhalation (e.g. asthma, COPD, and the like). In this way, operation of blower mechanism can remove gas from the breathing system until a threshold pressure is achieved, as a results of the pressure regulation activity of blower mechanism 2100. In some instances, blower mechanism 2100 can be used in a contiguous way, for example with a spontaneously breathing patient, during an intubation process, or with any ventilation platform. During operation of blower mechanism 2100, patient can breathe spontaneously through blower mechanism 2100.

According to some embodiments, a gas mover or blower mechanism can be used in conjunction with an ITD on an anesthesia machine, without changing gas flow in the anesthesia machine or altering the fresh gas flow (FGF). The gas mover or blower mechanism can be used without affecting volume monitors, delivered concentrations, or consumption of fresh gas. In some instances, the gas mover or blower mechanism can affect patient airway pressure monitoring. According to some embodiments, patient airway pressure will be lower, by the gas mover or blower mechanism pressure setting, at all points in the airway pressure curve. In some cases, a gas mover or blower mechanism can create a back pressure during inspiration.

Operation or control of flow control assemblies as discussed herein may be based on information obtained from a variety of sending instruments. For example, the operation of flow control assemblies can be based on information or signals obtained from or sent by one or more flow sensors or pressure sensors located throughout an anesthesia machine or ventilator. FIGS. 3 and 4 illustrate various possible locations for IPR threshold valves and IPR pumps. It is understood that systems and methods as disclosed herein may involve one or more flow sensors or pressure sensors positioned at such locations.

Figure 22:
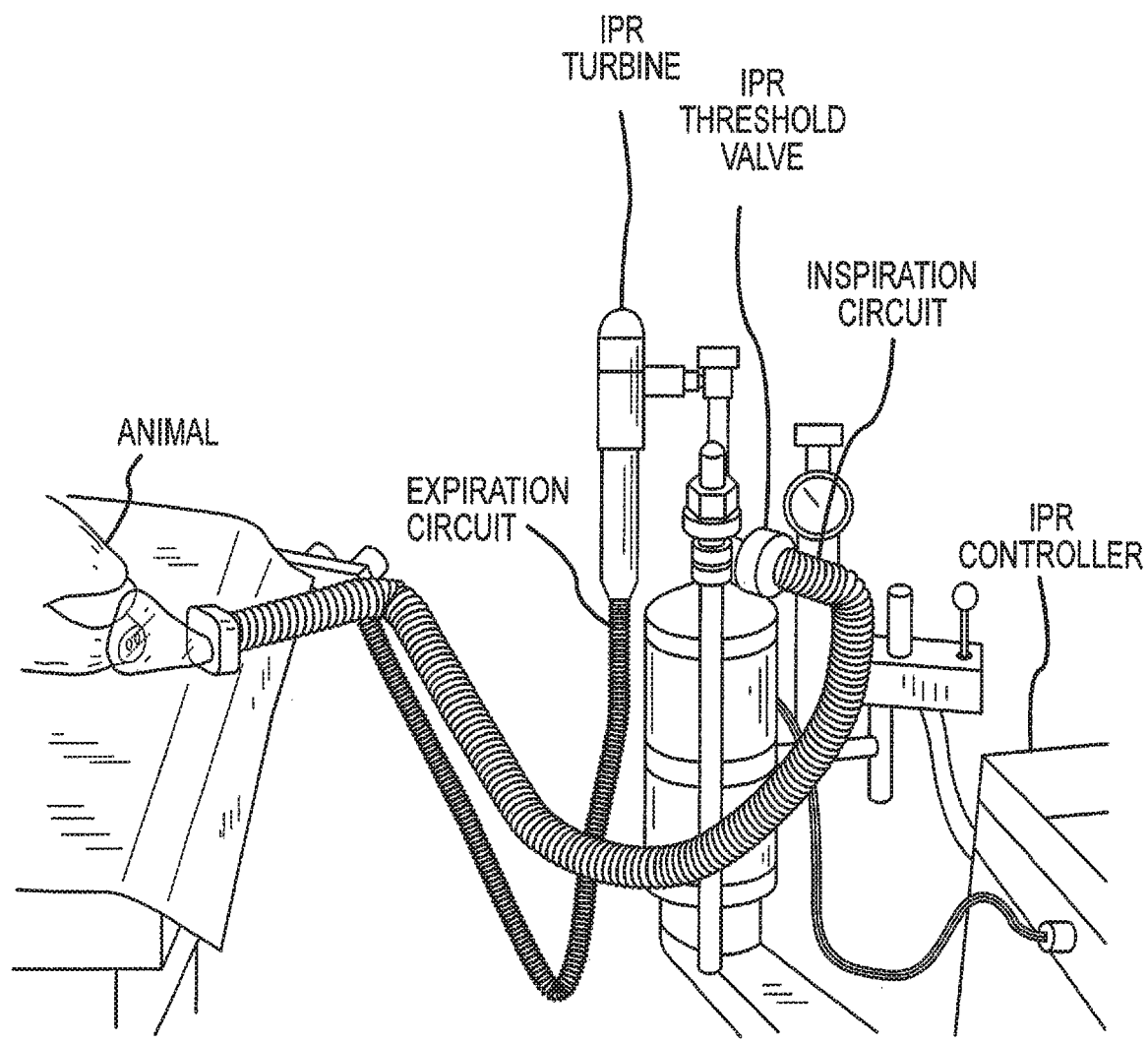
FIG. 22 depicts aspects of a therapeutic system for providing a respiratory treatment to an individual, according to embodiments of the present invention.

FIG. 22 depicts aspects of a therapeutic system for providing a respiratory treatment to an individual, according to embodiments of the present invention. As depicted here, the system includes an expiration circuit and an IPR turbine coupled thereto, an inspiration circuit and an IPR threshold valve coupled thereto, and an IPR controller. Such a system may be attached with, or part of, an anesthesia machine, a ventilator, or the like. In some instances, the system can be used to lower the airway pressure of an individual to a desired amount, for example to a pressure between about 0 cm $H_2O$ and about −15 cm $H_2O$. In some cases, the pressure lowering can be achieved after positive pressure ventilation (PPV). FIG. 22 shows the use of the IPR system in a ventilation circuit. The IPR turbine generates a level of intrathoracic pressure, which may be determined by the operator, for example using both the IPR controller, the IPR impedance threshold valve, or both.

Periodic Pressure Profile or Administration

According to some embodiments, negative pressure may be administered to or provided within the patient airway on a continuous basis, or an intermittent or periodic basis. In some cases, a positive pressure breath is always provided between such episodic negative pressure pulses. Systems and methods may involve the administration of periodic pressure pulses applied to the airway of a patient. Relatedly, systems and methods may involve generating a periodic pressure profile within the airway of a patient. For example, a blower mechanism can be configured to supply a negative pressure protocol to the airway of the individual via the patient connection mechanism. In some cases, the blower mechanism may be operated in conjunction with operation of a manual bag valve mask mechanism, a mechanical ventilator machine, or an anesthesia machine. In some cases, the blower mechanism may be coupled with a manual bag valve mask mechanism, a mechanical ventilator machine, or an anesthesia machine. Optionally, a negative pressure protocol may include a continuous application of a negative pressure. In some cases, a negative pressure protocol may include an intermittent application of negative pressure. Relatedly, in some cases operation of the blower may be activated and deactivated throughout the course of a treatment. In some cases, a manual bag valve mask mechanism, a mechanical ventilator machine, or an anesthesia machine may be configured to provide a positive pressure breath protocol to the airway of the patient. In some cases, a negative pressure protocol may include an intermittent application of individual negative pressure pulses to the airway of the individual, and a manual bag valve mask mechanism, a mechanical ventilator machine, or an anesthesia machine may be configured to provide positive pressure breath pulses to the airway of the patient, such that alternating negative and positive pressure pulses are provided to the airway of the patient.

Dynamic Systems Optimization

In some embodiments, systems and methods may employ Dynamic Systems Optimization to harness resonance frequencies in the patient's thoracic cavity, respiratory, and cardiac systems, and dynamic interactions between these individual patient systems. Dynamic Systems Optimization provides a means for analysis of the patient in a frequency domain by measuring at least one physiologic parameter, for example the patient's airway pressure, in response to a driving signal or input to the body, such as chest compressions or other input signal, or to a natural physiologic parameter such as pulse rate, for example. Based on the interaction between the two signals the system can calculate and respond to time constants in the patient's physiology to optimize the application of the therapy. Adjustment of therapeutic systems based on Dynamic Systems Optimization can be in the form of messaging, delivered to the clinician, or automated control feedback, which adjusts the therapeutic intervention or interventions automatically, or a combination thereof. Dynamic Systems Optimization can be used to optimize or enhance circulation to the heart and/or brain, based upon the measured physiological signal and the augmentation in circulation by the methods and devices herein.

In other embodiments designed primarily for the treatment of cardiac arrest and organ reperfusion after prolonged ischemic periods, maintenance of continuous or periods of intermittent negative intrathoracic pressure, when intentional pauses in chest compression (e.g. stutter CPR) are used in the process of post-conditioning, may be used to pull blood through the capillary beds and/or reduce intracranial pressure. Hence, embodiments of the present invention provide systems and methods for improving reperfusion after cardiac arrest, aspects of which are discussed in Yannopoulos et al., "Controlled pauses at the initiation of sodium nitroprusside-enhanced cardiopulmonary resuscitation facilitate neurological and cardiac recovery after 15 minutes of untreated ventricular fibrillation" Crit. Care Med. 2012 May 40(5):1562-9 (2012), the content of which is incorporated herein by reference for all purposes, and also in U.S. Patent Publication No. 2007/0277826, incorporated herein by reference for all purposes, as well as in U.S. patent application Ser. Nos. 13/554,458 and 13/554,986 both filed Jul. 20, 2012, both incorporated herein by reference for all purposes, and in U.S. Pat. Nos. 5,551,420, 5,692,498, 6,062, 219, 6,526,973, 6,604,523, 6,986,349, 7,195,013, and 7,210, 480, each of which is incorporated herein by reference for all purposes. The presence of a sustained negative intrathoracic pressure during the intentional pause when providing reperfusion injury protection during cardiopulmonary resuscitation provides a means to further reduce reperfusion injury and cell death after prolonged ischemic intervals at the time blood flow in reintroduced into the ischemic organ or body.

Flow Control Systems and Methods

Figure 23:
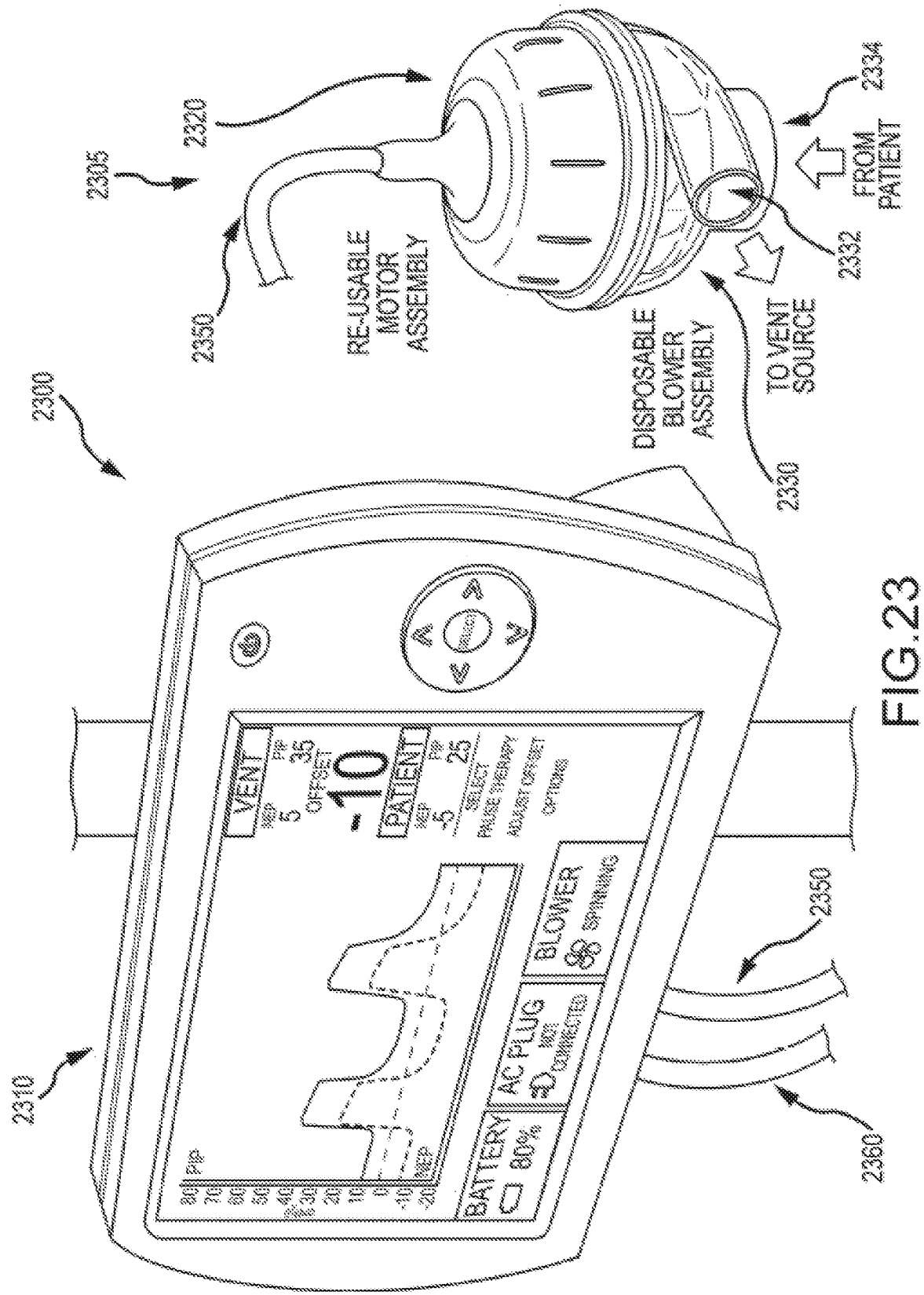
FIG. 23 depicts aspects of a system for providing a respiratory and/or circulatory treatment to an individual, according to embodiments of the present invention.

FIG. 23 depicts aspects of an exemplary system for providing intrathoracic pressure regulation (IPR) to a patient, according to embodiments of the present invention. As depicted here, the system 2300 includes a control and display mechanism 2310, a reusable motor assembly 2320, and a disposable blower apparatus 2330. The blower apparatus includes an aperture or vent 2332, which optionally may be configured to fluidly communication with an external pressure source as described elsewhere herein. The blower apparatus also includes a patient connection port 2334, which is configured to provide fluid communication with an airway of a patient. The systems also includes a cable 2350 for providing connectivity between the controller mechanism 2310 and the blower motor assembly 2320, and a cable 2360 for providing connectivity between the controller mechanism 2310 and patient sensors (not shown).

The display mechanism 2310 is configured to provide a visual indication of peak inspiratory pressure (PIP) and negative expiratory pressure (NEP). The upper waveform corresponds to airway pressures present in a ventilator (or other external positive pressure source) and the lower waveform corresponds to airway pressures present within the patient. The offset shown here between the upper and lower waveforms corresponds to a between what the airway pressure as registered by a ventilator and the actual patient airway pressure. Hence, the flow control system 2305 (e.g. motor 2320 and blower 2330) can operate as a valve-less pressure regulator, and can effectively be invisible to the ventilator. In some embodiments, the offset may be referred to as "IPR therapy level" and may correspond to the number that represents the nadir of the patient airway pressure. As shown here, the system can display patient proximal and ventilator pressure waveforms, along with corresponding numerical values.

Hence, aspects of a flow control assembly 2305 may be in operative association with a controller or control assembly, according to embodiments of the present invention. Information or data from patient sensors (not shown) can be used by the controller 2310 to regulate operation of motor assembly 2350. As discussed elsewhere herein, a blower system such as flow control system 2305 can be placed in fluid communication between a patient and a manual or automatic ventilation source. A blower 2330 can be controlled to create and regulate a targeted pressure differential between the patient and ambient air or a mechanical ventilation connection.

In some instances, a patient may breathe ambient air through vent 2332 and against impedance created by the blower 2330 to reduce pressures in the thorax. The blower 2330 can also reduce the pressure during exhalation by extracting gasses until a targeted negative pressure is achieved by the blower and control mechanisms.

According to some embodiments, a manual ventilation device may be placed in fluid communication with vent 2332. Exemplary devices include manual resuscitators, manual ventilators, and the like. A manual ventilation device may be connected to the blower. In some instances, a manual ventilation device may have a blower integrated into the structure of the manual resuscitator itself.

As described elsewhere herein, the flow control assembly 2305 can operate as a valve-less pressure regulator connected to a patient's airway. Relatedly, the flow control assembly 2305 can provide for to-and-fro gas flow during inspiration and exhalation, without creating a physical barrier or seal which would interrupt or impede such air flow at any point during an inhalation:exhalation respiratory cycle.

During exhalation, the flow control assembly 2305 can be controlled in such a way as to produce a regulated negative pressure in the patient's airways. During exhalation, the flow of gas is away from the patient.

During inspiration, the blower pressure of the flow control assembly 2305 may be overcome by a ventilator or manual resuscitator to allow the slippage of gas, retrograde through the blower, and toward the patient. The added pressure required to overcome the blower or flow control assembly 2305 during inspiration can be offset by the incremental reduction in pressure during the previous exhalation.

According to some embodiments, sub-ambient pressures (e.g. within a patient airway) created by the flow control assembly 2305 can cause a net reduction in the intrathoracic volume of gas. This reduced volume of gas in the thorax creates a potential space for the return of additional venous blood to the heart and thus improves the circulation of blood in the brain and vital organs.

According to some embodiments, the controller system 2310 for the motor apparatus 2320 includes a pressure sensor which monitors the patient's airway pressure between the blower 2330 and the patient. Information from such a pressure sensor can be used to control the blower pressure or the operation of the flow control assembly 2305, such that the targeted negative pressure is achieved independent of small amounts of pressure that may be produced by an attached ventilator or anesthesia machine.

According to some embodiments, pressure sensors may be present at the patient and ventilator connections to the blower, and can be used to monitor the pressure produced by an attached ventilation device and pressure in the patient's airway respectively. As shown in FIG. 23, such pressure information can be displayed as waveform and numeric information on a control box 2310.

As discussed elsewhere herein, the interaction of the flow control assembly 2305 with a patient receiving a series of breaths can result in a reduction in the baseline pressure of the patient. The inspiration breaths, for example as delivered by a ventilator, may result in inspiration pressures that do not exceed zero. Nevertheless, gas is exchanged, continues with inspiration volumes being delivered to the patient and exhaled volumes leaving the patient's airways. The patient's airway pressure baseline is reduced by the blower pressure provided by the flow control assembly 2305.

Figure 24:
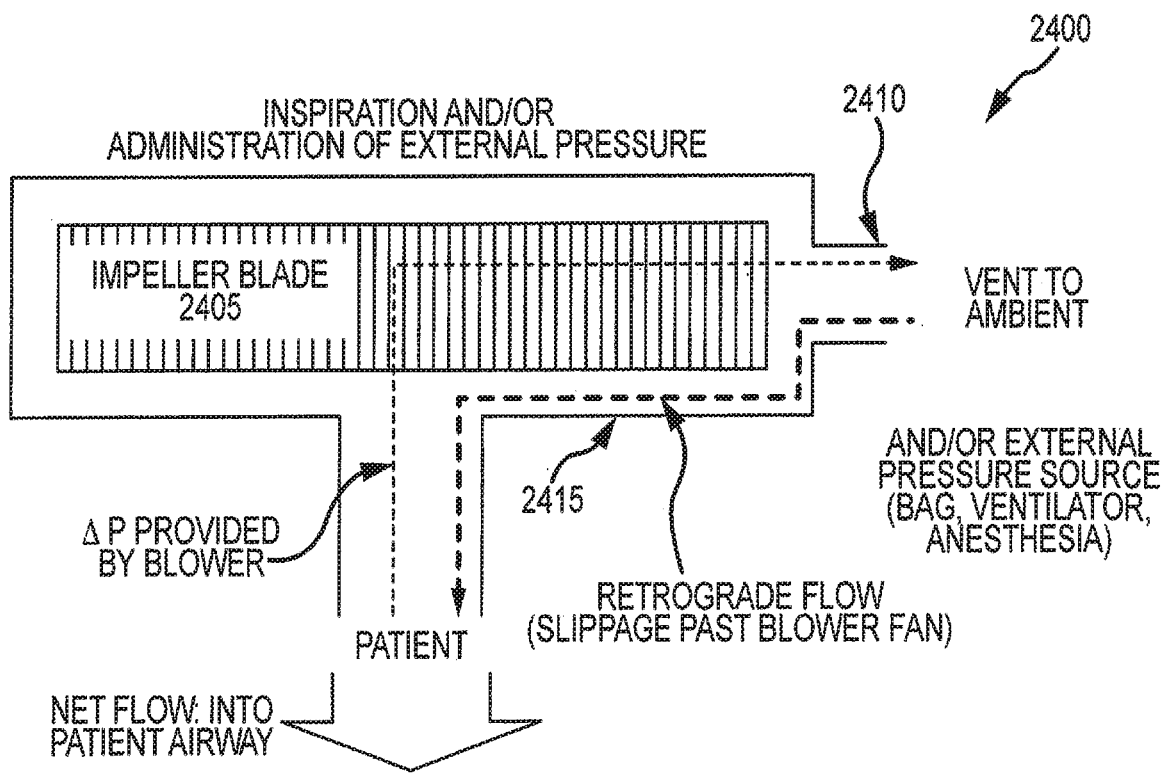
FIG. 24 depicts aspects of a system for providing a respiratory and/or circulatory treatment to an individual, according to embodiments of the present invention.

FIG. 24 depicts operational aspects of a flow control assembly 2400 according to embodiments of the present invention. As depicted here, the impeller blade 2405 provides an air flow force with operates to remove gas from the patient airway, for example by actively extracting gases from the patient airway. Concurrently, the vent 2410 provides a passage for incoming air via inhalation (or via a positive pressure source such as a bag, ventilator, anesthesia machine) to enter the patient lungs, in a retrograde flow fashion (e.g. contra to the pressure differential or flow force provided by the impeller blade), as slippage across the blower (e.g. between the blower fan blade 2405 and the blower housing 2415). Here, the incoming flow force exceeds the exiting flow force, and the net result is that there is air flow into the patient airway. Alternatively, where the incoming flow force is equal to the exiting flow force, there result is that there is no air flow into or out of the patient airway.

Figure 25:
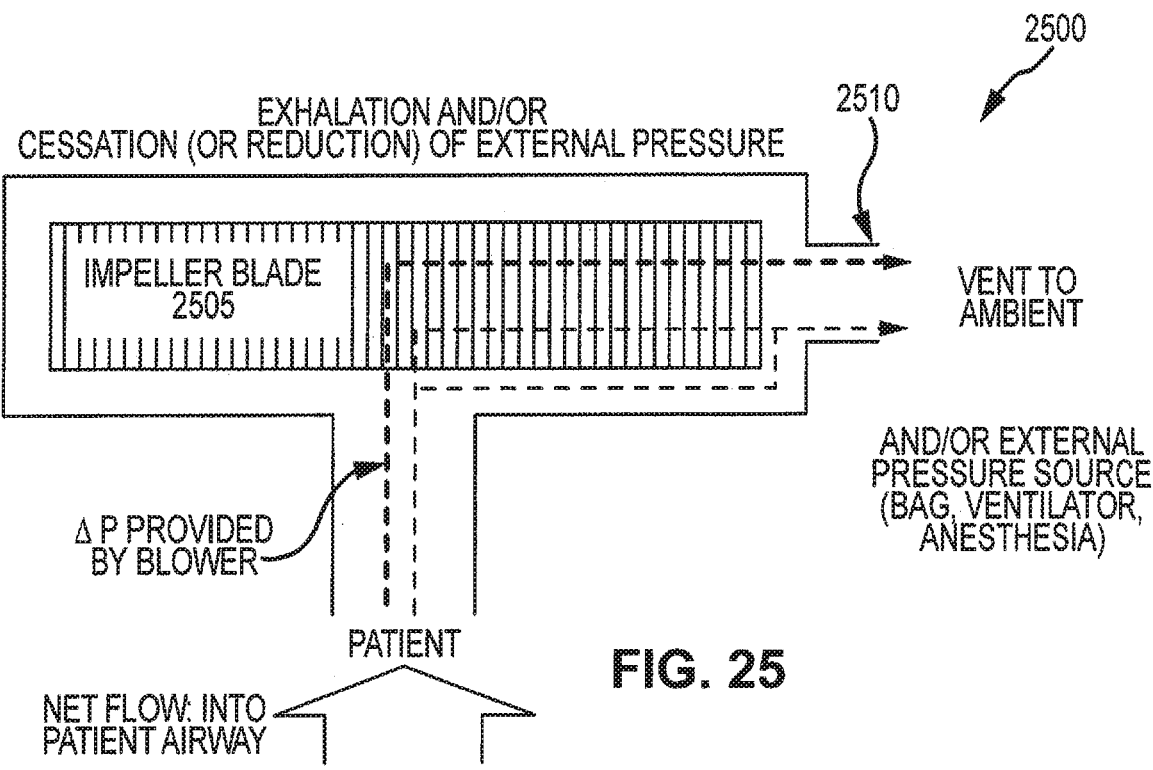
FIG. 25 depicts aspects of a system for providing a respiratory and/or circulatory treatment to an individual, according to embodiments of the present invention.

FIG. 25 depicts operational aspects of a flow control assembly 2500 according to embodiments of the present invention. As depicted here, the impeller blade 2505 provides an air flow force with operates to remove gas from the patient airway, for example by actively extracting gases from the patient airway. Concurrently, the vent 2510 provides a passage for the air exiting the patient airway, in alignment with the pressure differential or flow force provided by the impeller blade. Here, there is little or no incoming flow force, and the net result is that there is air flow out of the patient airway.

Figure 26:
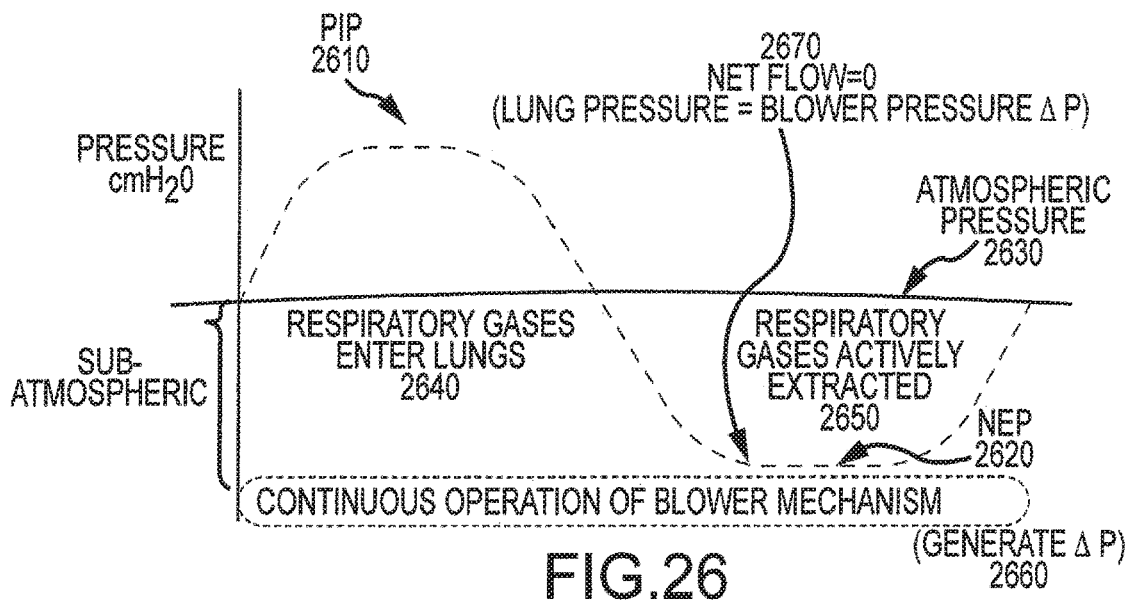
FIG. 26 depicts aspects of a technique for providing a respiratory and/or circulatory treatment to an individual, according to embodiments of the present invention.
Figure 27:
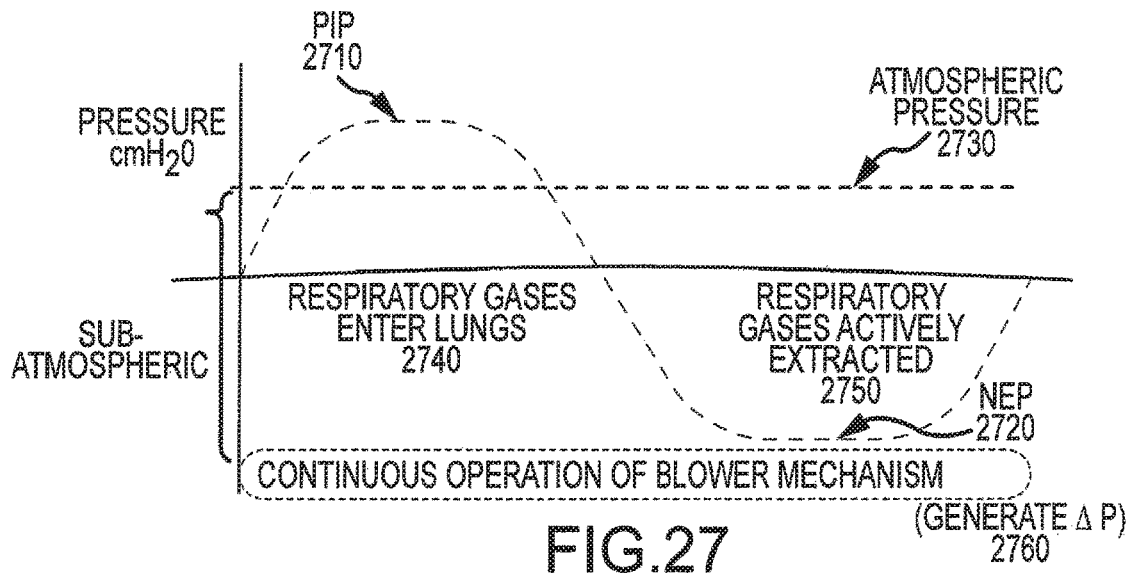
FIG. 27 depicts aspects of a technique for providing a respiratory and/or circulatory treatment to an individual, according to embodiments of the present invention.
Figure 28:
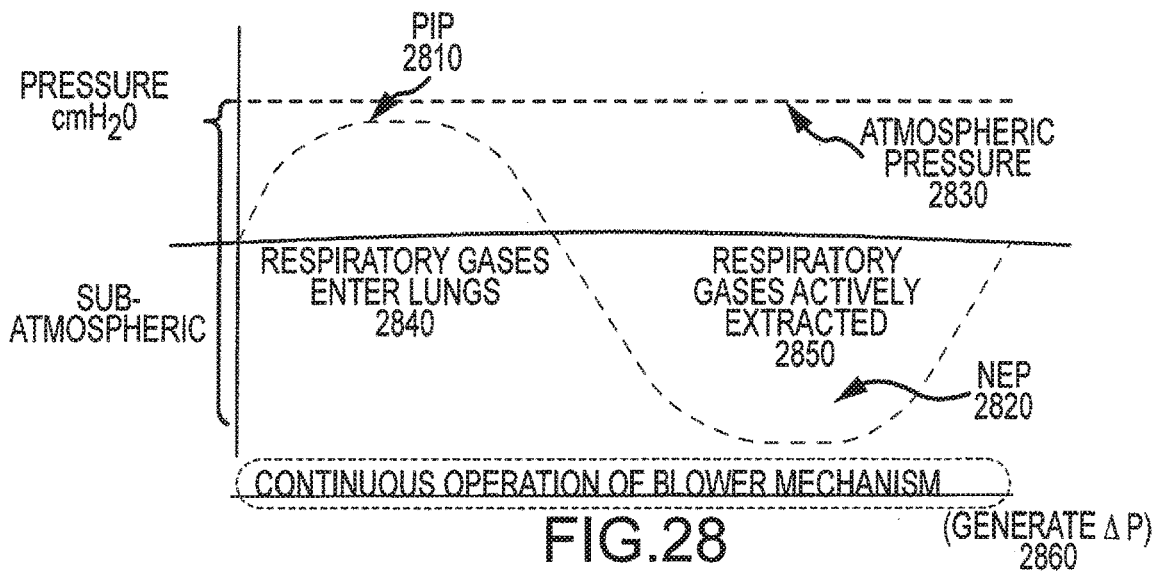
FIG. 28 depicts aspects of a technique for providing a respiratory and/or circulatory treatment to an individual, according to embodiments of the present invention.

FIGS. 26 to 28 depict various pressure waveforms associated with operational aspects of a flow control assembly, according to embodiments of the present invention. Typically, a patient respiration cycle (inspiration:expiration) occurs at a rate of about 12 breaths per minute, or 5 seconds per cycle. The cycle ratios show here are about 1:1, although other ratios are possible.

The peak inspiratory pressure (PIP) 2610 and negative expiratory pressure (NEP) 2620 of FIG. 26 can be 10 cm $H_2O$ and −12 cm $H_2O$, respectively, for example. Other similar pressure values can also be used. The zero line 2630 can represent atmospheric or ambient pressure. In the inspiratory phase 2640, gases enter the patient airway and there is retrograde air flow slippage across the blower fan. The entering air can be a result of an administered amount of tidal volume or pressure. In the expiratory phase 2650, gases are actively extracted. As shown here, the continuous operation of the blower mechanism 2660 generates a ΔP, which at times is overcome by the countervailing inflow forces. Where the lung pressure equals the blower pressure, there is no net flow 2670 into or out of the patient airway.

The peak inspiratory pressure (PIP) 2710 and negative expiratory pressure (NEP) 2720 of FIG. 27 can be 4 cm $H_2O$ and −12 cm $H_2O$, respectively, for example. Other similar pressure values can also be used. The zero line 2730 can represent atmospheric or ambient pressure. In the inspiratory phase 2740, gases enter the patient airway and there is retrograde air flow slippage across the blower fan.

Accordingly, the difference between the highest and lowest airway pressures can be about 16 cm $H_2O$. In some instances, the difference may be about 12 cm $H_2O$. In some instances, the difference may be within a range from about 12 cm $H_2O$ to about 16 cm $H_2O$. It is understood that operation of the system may involve other values or ranges consistent with the therapeutic objectives as discussed herein.

The entering air can be a result of an administered amount of tidal volume or pressure. As compared to FIG. 26, however, the administered tidal volume or pressure of FIG. 27 is lower, and hence a larger duration or proportion of the respiratory cycle occurs at the sub-atmospheric range.

In the expiratory phase 2750, gases are actively extracted. As shown here, the continuous operation of the blower mechanism 2760 generates a ΔP, which at times is overcome by the countervailing inflow forces. Where the lung pressure equals the blower pressure, there is no net flow into or out of the patient airway.

The peak inspiratory pressure (PIP) 2810 and negative expiratory pressure (NEP) 2820 of FIG. 28 can be 0 cm $H_2O$ and −16 cm $H_2O$, respectively, for example. Other similar pressure values can also be used. The zero line 2830 can represent atmospheric or ambient pressure. In the inspiratory phase 2840, gases enter the patient airway and there is retrograde air flow slippage across the blower fan.

The entering air can be a result of an administered amount of tidal volume or pressure. As compared to FIGS. 26 and 27, however, the administered tidal volume or pressure of FIG. 28 is lower, or may be nonexistent. Hence, a larger duration or proportion of the respiratory cycle, or even the entirety of the duration of the respiratory cycle, may occur at the sub-atmospheric range.

In the expiratory phase 2850, gases are actively extracted. As shown here, the continuous operation of the blower mechanism 2860 generates a ΔP, which at times is overcome by the countervailing inflow forces. Where the lung pressure equals the blower pressure, there is no net flow into or out of the patient airway.

Accordingly, exemplary systems and methods according to embodiments of the present invention provide for the delivery of respiratory gas exchange at and below atmospheric pressure. Lowering expiratory pressures to sub-atmospheric levels can cause more venous blood flow back to the thorax into the heart and lungs. Lowering expiratory pressures to sub-atmospheric levels can also lower intracranial pressure. In the three schematics of FIGS. 26 to 28, the lungs are filled with respiratory gases. In FIGS. 27 and 28, however, the lungs are filled but the thoracic pressures overall are reset to less than atmospheric pressure. Yet importantly, the thoracic pressures are equal to or less than the pressure in the rest of the body, which affects the net flow of blood into and out of the thorax.

In the embodiment depicted in FIG. 27, intrathoracic pressures are below atmospheric pressure except when there is the delivery of a positive pressure breath at which point the maximum pressures in the thorax exceed atmospheric pressure. In the embodiment depicted in FIG. 28, intrathoracic pressures are below atmospheric pressure even at the point of maximum pressures used to fill the lungs.

In each of the three situations depicted by FIGS. 26 to 28, when the pressure inside the thorax is less than atmospheric pressure, venous blood and to some extent cerebral spinal fluid in the spinal column is drawn into the thorax. Further, there is the generation of a change in pressure from peak to trough levels which results in the movement of respiratory gases into and out of the lungs which results in a net exchange in volume of respiratory gases in the thorax for a volume of blood in the thorax. As respiratory gases are extracted, a volume of blood is returned to the thorax proportional on a per volume basis.

Hence, the blower mechanism can operate to reduce or remove volume, and thereby improve circulation. Further, the blower mechanism can operate to reduce the baseline pressure. What is more, embodiments of the present invention encompass the operation of an inspiratory pressure transducer to regulate pressure.

Pleural Catheters

As discussed elsewhere herein, a blower mechanism can be used to supply a negative pressure protocol to the airway of the individual. Relatedly, a blower mechanism can be used to transiently reduce lung volume in an individual, which can facilitate the insertion of a pleural catheter or chest tube into the patient. By reducing the lung volume using the blower mechanism, it is possible to reduce the possibility of damaging the lung or otherwise impacting the lung during insertion of a catheter, tube, or central line thereof. Hence, an operator can use a blower mechanism to reduce an individual's lung when inserting a pleural catheter such as a PleurX® pleural drainage catheter or an Aspira* pleural drainage catheter. Similarly, an operator can use a blower mechanism to reduce an individual's lung when inserting a pleural pressure catheter or other pleural manometry devices, such as those described in Villena et al, Am. J. Respir. Crit. Care Med. Oct. 1, 2000 vol. 162 no. 4 1534-1538, the content of which is incorporated herein by reference.

Embodiments of the invention have now been described in detail for the purposes of clarity and understanding. However, it will be appreciated that certain changes and modifications may be practiced within the scope of the appended claims.

What is claimed is:

1. A system for providing intrathoracic pressure regulation (IPR) to an individual comprising:
    a patient connection port for coupling with an airway of the individual;
    a vent configured to be in fluid communication with a pressure source or ambient air;
    a housing comprising a fluid flow passage extending between the patient connection port and the vent;
    a blower disposed within the fluid flow passage of the housing between the patient connection port and the vent; and
    a motor configured to be operatively coupled with the blower for the blower to extract gas from the patient connection port,
    wherein the blower, motor and fluid flow passage in operation are configured to allow retrograde airflow from the vent to the patient connection port and compel airflow from the patient connection port to the vent simultaneously with the retrograde airflow.

2. The system according to claim 1, wherein the motor is configured to operate the blower to provide a reduction in pressure in the airway of the individual.

3. The system according to claim 1, wherein the blower comprises an impeller.

4. The system according to claim 3, wherein the impeller is operatively associated with the motor by way of a magnetic clutch.

5. The system according to claim 1, wherein the blower, motor and fluid flow passage in operation are configured to generate a pressure differential within a range of between about 0 cm $H_2O$ and about 20 cm $H_2O$.

6. The system according to claim 1, wherein the blower, motor and fluid flow passage in operation are configured to generate a pressure differential within a range of between about 3 cm $H_2O$ and about 16 cm $H_2O$.

7. The system according to claim 1, wherein the blower, motor and fluid flow passage in operation are configured to permit airflow between the patient connection port and the vent, without forming a physical barrier that prevents airflow therebetween.

8. The system according to claim 1, wherein the blower, motor and fluid flow passage in operation are configured to maintain sub-atmospheric pressures within the thorax of the individual.

9. The system according to claim 1, further comprising a pressure sensor that monitors the individual's airway pressure, and further comprising a controller configured to receive information from the pressure sensor and control operation of the motor based on the information.

10. The system according to claim 9, further comprising a display configured to provide a visual indication of the individual's airway pressure.

11. The system according to claim 10, wherein the visual indication comprises airway information including at least one of peak inspiratory pressure, expiratory pressure, an indication of intrathoracic pressure regulation therapy administered to the patient, and a pressure waveform of the patient's airway.

12. The system according to claim 1, wherein the external pressure source comprises at least one of a manual ventilation device, a bag-valve mask, and a ventilator.

13. The system according to claim 1, wherein the motor and the blower are configured to be coupled and decoupled from one another.

14. The system according to claim 13, wherein the motor is reusable and the blower is disposable.

15. The system according to claim 1, wherein the blower, motor and fluid flow passage in operation are configured to allow for intermittent airflow between the vent and the individual's lungs.

16. A device for providing intrathoracic pressure regulation (IPR) to an individual, comprising:
   a housing having at least two ports, a first port configured to be in fluid communication with ambient air and a second port configured to be in fluid communication with the individual's airway, and a fluid flow passage extending between the first port and the second port;
   a blower disposed within the housing and configured to provide negative intrathoracic pressure within the individual by moving air from the individual's airway, through the second port, through the fluid flow passage, and through the first port, the blower positioned such that at least one secondary passage exists between the blower and the housing, the secondary passage being in fluid communication with the first port and the second port and allowing retrograde airflow from the first port through the secondary passage, and through the second port to the individual's airway, against the movement of air caused by the blower; and
   a motor in operative association with the blower.

17. The device according to claim 16, further comprising a pressure sensor that monitors the individual's airway pressure between the blower and the individual, and a controller that receives information from the pressure sensor and controls operation of the motor based on the information.

18. The device according to claim 16, wherein the motor is configured to operate the blower to provide a reduction in pressure in the airway of the individual.

19. The device according to claim 16, wherein the blower, motor and fluid flow passage in operation are configured to allow retrograde airflow between the first port and the second port.

20. The device according to claim 16, wherein the blower comprises an impeller.

21. The device according to claim 20, wherein the impeller is operatively associated with the motor by way of a magnetic clutch.

22. The device according to claim 16, wherein the blower, motor and fluid flow passage in operation are configured to generate a pressure differential within a range of between about 0 cm $H_2O$ and about 20 cm $H_2O$.

23. The device according to claim 16, wherein the blower, motor and fluid flow passage in operation are configured to permit airflow between the first port and the second port, without forming a physical barrier that prevents airflow therebetween.

24. The device according to claim 16, wherein the motor and the blower are configured to be coupled and decoupled from one another.

* * * * *